(12) United States Patent
Imamura et al.

(10) Patent No.: US 8,134,045 B2
(45) Date of Patent: Mar. 13, 2012

(54) PROTEIN INVOLVED IN RESTORATION OF CYTOPLASMIC MALE STERILITY TO FERTILITY AND GENE ENCODING THE PROTEIN AND GENE

(75) Inventors: Jun Imamura, Tokyo (JP); Hideya Fujimoto, Tokyo (JP); Ritsuko Yanagidate, Aichi (JP); Nobuya Koizuka, Kanagawa (JP); Takako Sakai, Tokyo (JP); Takahiko Hayakawa, Tokyo (JP)

(73) Assignee: Institut National de la Recherche Agronomique, Paris (FR)

( * ) Notice: Subject to any disclaimer, the term of this patent is extended or adjusted under 35 U.S.C. 154(b) by 109 days.

(21) Appl. No.: 12/251,191

(22) Filed: Oct. 14, 2008

(65) Prior Publication Data

US 2010/0199376 A1   Aug. 5, 2010

Related U.S. Application Data

(63) Continuation of application No. 10/613,053, filed on Jul. 7, 2003, now Pat. No. 7,767,886, which is a continuation-in-part of application No. 10/451,366, filed as application No. PCT/JP02/04092 on Apr. 24, 2002, now abandoned.

(30) Foreign Application Priority Data

| Apr. 25, 2001 | (JP) | 2001-128008 |
| Jul. 3, 2001 | (JP) | 2001-202082 |
| Jan. 29, 2002 | (JP) | 2002-20083 |

(51) Int. Cl.

| C12N 15/82 | (2006.01) |
| C12N 15/29 | (2006.01) |
| C12N 15/62 | (2006.01) |
| C12N 5/04 | (2006.01) |
| C12N 5/10 | (2006.01) |
| A01H 5/00 | (2006.01) |
| A01H 5/10 | (2006.01) |

(52) U.S. Cl. ........ 800/274; 800/287; 800/303; 800/306; 435/69.8; 435/320.1; 435/419; 536/23.6

(58) Field of Classification Search ........................ None
See application file for complete search history.

(56) References Cited

U.S. PATENT DOCUMENTS

| 4,686,191 | A | 8/1987 | Itoh et al. |
| 4,939,094 | A | 7/1990 | Kuga et al. |
| 5,160,735 | A | 11/1992 | Yasumura et al. |
| 5,644,066 | A | 7/1997 | Sakai et al. |
| 5,750,871 | A | 5/1998 | Moloney et al. |
| 5,789,566 | A | 8/1998 | Bonhomme et al. |
| 5,866,782 | A | 2/1999 | Iwabuchi et al. |
| 5,973,233 | A | 10/1999 | Burns et al. |
| 6,229,072 | B1 | 5/2001 | Burns et al. |
| 6,365,798 | B1 | 4/2002 | Brown |
| 6,951,970 | B2 * | 10/2005 | Brown .......................... 800/287 |
| 7,071,375 | B2 * | 7/2006 | Brown et al. ................. 800/274 |
| 7,164,058 | B2 * | 1/2007 | Hanson et al. ................ 800/298 |
| 7,767,886 | B2 | 8/2010 | Imamura et al. |
| 2003/0126646 | A1 | 7/2003 | Brown et al. |
| 2003/0237112 | A1 | 12/2003 | Brown et al. |
| 2004/0117868 | A1 | 6/2004 | Imamura et al. |

FOREIGN PATENT DOCUMENTS

| EP | 0 599 042 | 6/1994 |
| JP | 58-110600 | 7/1983 |
| JP | 63-233798 | 9/1988 |
| JP | 2-227075 | 9/1990 |
| JP | 3-22979 | 1/1991 |
| JP | 2687396 | 8/1997 |
| JP | 2001-145497 | 5/2001 |
| WO | WO 92/05251 | 4/1992 |
| WO | WO 97/49831 | 12/1997 |
| WO | WO 98/54340 | 12/1998 |
| WO | WO 03/006622 | 1/2003 |

OTHER PUBLICATIONS

Akagi et al. (2004) "Positional Cloning of the Rice Rf-1 Gene, a Restorer of BT-Type Cytoplasmic Male Sterility that Encodes a Mitochondria-Targeting PPR Protein," *Theor. Appl. Genet.* 108:1449-1457.
Alting-Mees et al. (1989) "pBluescript II: Gene Mapping Vectors," *Nuc. Acids Res.* 17(22):9494.
Araya et a. (1993) "Of RNA Editing and Cytoplasmic Male Sterility in Plants," In; *Plant Mitochondria*, Brennice et al. eds., VCH: Weinheim, Germany pp. 83-91.
Bonhomme et al. (1992) "Sequence and Transcript Analysis of the Nco2.5 Orgura-Specific Fragment Correlated with Cytoplasmic Make Sterility in *Brassica* cybrids," *Mol. Gen. Genet.* 235(2-3):340-348.
Brown, G. (1999) "Unique Aspects of Cytoplasmic Male Sterility and Fertility Restoration in *Brassica napus*," *J. Heredity* 90(3):351-356. Jefferson R. A. et al. (1987) "GUS fusions; β-glucuronidase as a sensitive and versatile gene fusion marker in higher plants," *EMBO J.* 6(13):3901-3907.
Coffin et al. (1997) "The Neurospora Crassa CYA-5 Nuclear Gene Encodes a Protein with a Region of Homology to the *Saccharomyces cerevisiae* PET309 Protein and is Required in a Post-Transcriptional Step for the Expression of the Mitochondrially Encoded COXI Protein," *Curr. Genet.* 32(4):273-280.
Cui et al. (May 31, 1996) "The rf2 Nuclear Restorer Gene of Male-Sterile T-Cytoplasm Maize," *Science* 272:1334-1336.
Delourme et al. (1998) "Characterisation of the Radish Introgression Carrying the *Rfo* Restorer Gene for the *Ogu*-INRA Cytoplasmic Male Sterility in Rapeseed (*Brassica napus* L.)," *Theor. Appl. Genet.* 97:129-134.
Delourme et al. (1995) "Rapeseed Today and Tomorrow," 9th International Rapeseed Congress, Murphy et al. eds., The Dorset Press, Dorchester, 1:6-8.
Desloire et al. (2003) "Identification of the Fertility Restoration Locus, *Rfo*, in Radish, as a Member of the Pentatricopeptide Repeat Protein Family," *EMBO Rep.* 4(6):588-594.

(Continued)

*Primary Examiner* — David T Fox
(74) *Attorney, Agent, or Firm* — Greenlee Sullivan P.C.

(57) ABSTRACT

The object of the present invention is to isolate Rf gene, particularly Rf1 gene derived from radish, and identify its structure. The present invention provides a protein involved in restoration of a cytoplasmic male sterile individual to fertility which has 14 or more pentatricopeptide repeat (hereafter may be abbreviated to PPR) motifs, wherein a group of the motifs is divided into 3 or more blocks, each of the individual blocks has at least 2 or more PPR motifs, and the block in a carboxyl terminal (C terminal) side has 4 PPR motifs.

36 Claims, 10 Drawing Sheets

OTHER PUBLICATIONS

Dulbecco et al. (1959) "Plaque Production by the Polyoma Virus," *Virology* 8(3):396-397.

Eagle, H. (Sep. 16, 1952) "Nutrition Needs of Mammalian Cells in Tissue Culture," *Science* 122:501-504.

Fisk et al. (May 4, 1999) "Molecular Cloning of the Maize Gene CRP1 Reveals Similarity Between Regulators of Mitochondrial and Chloroplast Gene Expression," *EMBO J.* 18(9):2621-2630.

Gerhus et al. (May 1990) "*Paracoccus denitrificans* Cytochrome $c_1$ Gene Replacement Mutants," *J. Bacteriol.* 172(5):2392-2400.

Grelon et al. (1994) "Ogura Cytoplasmic Male-Sterility (CMS)-Associated *orf138* is Translated into a Mitochondrial Membrane Polypeptide in Male-Sterile *Brassica* Cybrids," *Mol. Gen. Genet.* 243(5):540-547.

Hamilton, C.M. (Oct. 24, 1997) "A Binary-BAC System for Plant Transformation with High-Molecular-Weight DNA," *Gene* 200(1-2):107-116.

Huynh, T.V. et al. (1985) "Constructing and Screening cDNA Libraries in λgt10 and λgt11," in *DNA Cloning, A Practical Approach*, Chapter 2; (Ed., D.M. Glover) IRL Press (1985) pp. 49-78.

Imai et al. (2003) "Delimitation of the Fertility Restorer Locus *Rfk1* to a 43-kb Contig in Kosena Radish (*aphanus sativus* L.)," *Mol. Gen. Genet.* 269:388-394.

Imai, R.T. et al. "Characterization of cytoplasmic male sterility (CMS) and fertility restoration system in Kosena radish," (1997) *Breeding Sci.* 47:186.

Imai, R.T. et al. "Characterization of fertility restoration in cytoplasmic male-sterile Kosena radish," (1998) *Breeding Sci.* 48:197.

Iwabuchi et al. (1999) "Identification and Expression of the Kosena radish (*Raphanus sativus* cv. Kosena) Homologue of the Ogura Radish CMS-Associated Gene, orf138," *Plant Mol. Biol.* 39(1):183-188.

Buzza, G. C (1995) "Plant Breeding," in *Brassica Oilseeds Production and Utilization*, Kimber et al. eds., CAB International, Cambridge, pp. 153-175.

Koizuka et al. (2000) "Genetic Analysis of Fertility Restoration and Accumulation of ORF125 Mitochondrial Protein in the Kosena Radish (*Raphanus sativus* cv. Kosena) and a *Brassica napus* Restorer Line," *Theor. Appl. Genet.* 100:949-955.

Koizuka et al. (May 2003) "Genetic Characterization of a Pentatricopeptide Repeat Protein Gene, *orf687*, that Restores Fertility in the Cytoplasmic Male-Sterile Kosena Radish," *Plant J.* 34(4):407-415.

Koltunow et al. (Dec. 1990) "Different Temporal and Spatial Gene Expression Patterns Occur During Anther Development," *Plant. Cell.* 2(12):1201-1224.

Lahmy et al. (2000) "A Chloroplastic RNA-Binding Protein is a New Member of the PPR Family," *FEBS Lett.* 480(2-3):255-260.

Liu et al. (May 1999) "Complementation of Plant Mutants with Large Genomic DNA Fragments by a Transformation-Competent Artificial Chromosome Vector Accelerates Positional Cloning," *Proc. Nat. Acad. Sci. USA* 96:6535-6540.

Manthey et al. (Aug. 15, 1995) "The Product of the Nuclear Gene PET309 is Required for Translation of Mature mRNA and Stability or Production of Intron-Containing RNAs Derived from the Mitochondrial COX1 Locus of *Saccharomyces cerevisiae*," *EMBO J.* 14(16):4031-4043.

McCreath et al. (Jul. 29, 2000) "Production of Gene-Targeted Sheep by Nuclear Transfer from Cultured Somatic Cells," *Nature* 405:1066-1070.

Miyaji et al. (1989) "Expression of Human Lymphotoxin Derivatives in *Escherichia coli* and Comparison of Their Biological Activity in Vitro ," *Agric. Biol. Chem.* 53(1):277-279.

Miyaji et al. (1990) "Expression of Human Beta-Interferon in Namalwa KJM-1 Which was Adapted to Serum-Free Medium," *Cytotechnology* 3(2):133-140.

Mizukami et al. (1987) "A New SV40-Based Vector Developed for cDNA Expression in Animal Cells," *J. Biochem.* 101(5):1307-1310.

Moore et al. (Feb. 20, 1967) "Culture of Normal Human Leukocytes," *J. Am. Med. Assoc.* 199(8):519-524.

Murashige et al. (Jul. 1962) "A Revised Medium for Rapid Growth and Bio Assays with Tobacco Tissue Cultures," *Physiol. Plant.* 15(3):473-497.

Murayama et al. (1999) "Identification of RAPD and SCAR Markers Linked to a Restorer Gene for Ogura Cytoplasmic Male Sterility in Radish (*Raphanus sativus* L.) by Bulked Segregant Analysis," *Breeding Sci.* 49(2):115-121.

Murray et al. (1980) "Rapid Isolation of High Molecular Weight Plant DNA," *Nuc. Acids. Res.* 8(19):4321-4325.

Nishi et al. (1984) "Construction of Plasmid Expression Vectors Carrying the *Escherichia coli* Tryptophan Promoter," *Agric. Biol. Chem.* 48(3):669-675.

Nishibayashi et al. (1995) "Transformation of Cucumber (*Cucumis sativus* L.) Plants Using *Agrobacterium tumefaciens* and Regeneration from Hypocotyl explants," *Plant Cell. Report* 15(11):809-814.

Okayama H. and Berg, P. "A cDNA Cloning Vector that Permits Expression of cDNA Inserts in Mammalian Cells," (1983) *Mol. Cellular Biol.* 3(2):280-289.

Pelletier et al. (1983) "Intergeneric Cytoplasmic Hybridization in Cruciferae by Protoplast fusion," *Mol. Gen. Genet.* 191:244-250.

Robbelen et al. (1980) "Variation in Rapeseed Glucosinolates and Breeding for Improved Meal Quality," Ch.16, pp. 285-299.

Sakai et al. (1994) "Somatic Hybridization Between Radish (*Raphanus sativus*) and Rapeseed (*Brassica napus*)," In *Biotechnology in Agriculture and Forestry*, vol. 27 *Somatic Hybridization in Crop Improvement I*, Dajaj, Y.P.S. Ed., Springer-Verlag Berlin Heidelberg, pp. 320-333.

Sakamoto et al. (2000) "Mitochondrial Localization of AtOXA1, an *Arabidopsis* Homologue of Yeast Oxa1p Involved in the Insertion and Assembly of Protein Complexes in Mitochondrial Inner Membrane," *Plant Cell Physiol.* 41(10):1157-1163.

Sambrook et al. (1989) Ch. 7 "Extraction, Purification, and Analysis of Messenger RNA from Eukaryotic Cells," pp. 59-83 in *Molecular Cloning*, $2^{nd}$ ed. (Cold Spring Harbor Press).

Sambrook et al. (1989) Ch. 14, "In Vitro Amplification of DNA by Polymerase Chain Reaction," pp. 2-17 in *Molecular Cloning*, $2^{nd}$ ed. (Cold Spring Harbor Press).

Sambrook et al. (1989) Ch. 9 :Analysis and Cloning of Eukaryotic Genomic DNA, pp. 30-37, in *Molecular Cloning*, $2^{nd}$ ed. (Cold Spring Harbor Press).

Schnable et al. (May 1998) "The Molecular Basis of Cytoplasmic Male Sterility and Fertility Restoration," *Trends Plant Sci.* 3(5):175-180.

Seed, B. (1987) "An LFA-3 cDNA Encodes a Phospholipid-Linked Membrane Protein Homologous to its Receptor CD2," *Nature* 329:840-842.

Sekine et al.(Jul. 1985) "Cloning and Expression of cDNA for Salmon Growth Hormone in *Escherichia coli*," *Proc. Nat. Acad. Sci. USA* 82:4306-4310.

Singh et al. (May 1996) "Nuclear Genes Associate with a Single *Brassica* CMS Restorer Locus Influence Transcripts of Three Different Mitochondrial Gene Regions," *Genetics* 143(1):505-516.

Small et al. (Feb. 2000) "The PPR Motif—A TPR-Related Motif Prevalent in Plant Organellar Proteins," *Trends Biochem. Sci.* 25(2):45-47.

Syuuzyunsya (1996) Cell Engineering, Separate Volume: Biotechnology Experiment Illustrated, (2) Fundamentals of Gene Analysis: 161-166.

Terada et al. (1990) "Expression of CaMV35S-GUS Gene in Transgenic Rice Plants," *Mol. Gen. Genet.* 220(3):389-392.

Tsuchiya et al. (1995) "Tapetum-Specific Expression of the Gene for an Endo-β-1,3-Glucanase Causes Male Sterility in Transgenic Tobacco," *Plant Cell Physiol.* 36(3):487-494.

Uematsu et al. (1991) "*Agrobacterium*-Mediated Transformation and Regeneration of Kiwi Fruit," *Plant Cell Rep.* 10(6-7):286-290.

Vos et al. (1995) "AFLP: A New Technique for DNA Fingerprinting," *Nucleic Acids Res.* 23(21):4407-4414.

Yamagishi, H. (1998) "Distribution and Allelism of Restorer Genes for Ogura Cytoplsmic Male Sterility in Wild and Cultivated Radishes," *Gene Genet. Syst.* 73(2):79-83.

Yanisch-Perron et al. (1985) "Improved M13 Phage Cloning Vectors and Host Strains: Nucleotide Sequences of the M13mpl8 and pUC19 Vectors," *Gene* 33(1):103-119.

Kawasaki et al. (1997) "High capacity binary vector for complementation analysis of plant genome functions," (1997) *Biosci. Ind.* 55:37-39 (Japanese).

Morgan J.F., et al. (1950) "Nutrition of Animal cells in Tissue Culture. I. Initial Studies on a Synthetic Medium," *Pro. Soc. Experim. Medicine*, 73:1-8.

Catalogue of Oilseed Rape Cultivars 1995 ed. Compiled by Larry Serynk, Mycogen Plant Sciences 5649 E. Buckeye Road Madison, Wisconsin USA 53716.

Sin Idensi Kougaki Handbook. Zikken Igaku Supplemental, Youdosya 1996.

Procedure of the Western Canada Canola/Rapeseed Recommending Committee Incorporated for the Evaluation and Recommendation for Registration of Canola/Rapeseed Candidate Cultivars in Western Canada; pp. 1-10 and A1-A7 (1996).

* cited by examiner

```
pSTVI25-5'#LA12.nuc    1:GGATCCCAATTTCATTCTGCATCACTCTCCCTGTCGTTATGCGACCTCGCAAGGTTTTG    60
pSTVI25-5'#LA6.nuc     1:GGATCCCAATTTCATTCTGCATCACTCTCCCTGTCGTTATGCGACCTCG-CAAGGTTTTG   59
                         ***********************************************  ******** pSTVI25-5'#LA12.nuc   61:AAACGGCCGAAACGGGAAGTGACAATACCGCTTTTCTTGAGCATATAAATCATGATTAC-  119
pSTVI25-5'#LA6.nuc    60:AAACGGCCGAAACGGGAAGTGACAATACCGCTTTTCTTCAGCATATAAATGCATGATTAC  119
                         ************************************  ****** ******* * pSTVI25-5'#LA12.nuc  120:CTTTTTTCGAAAAATTGTCCACTTTTTGTCATAATCCTCACTTCCTACTGAATGTAAAGT  179
pSTVI25-5'#LA6.nuc   120:CTTTT-TCGAAAAATTGTCCACTTTTTGTCATAATCTCACTCCTACTGAAATTAA-A-GT  176
                         *** **************************   * *******   * * ** pSTVI25-5'#LA12.nuc  180:TAGTGAATTC  189
pSTVI25-5'#LA6.nuc   177:TAGTGAATTC  186
                         **********
```

Figure 6

PROTEIN INVOLVED IN RESTORATION OF CYTOPLASMIC MALE STERILITY TO FERTILITY AND GENE ENCODING THE PROTEIN AND GENE

CROSS-REFERENCE TO RELATED APPLICATIONS

This application is a Continuation of U.S. patent application Ser. No. 10/613,053, filed Jul. 7, 2003, now U.S. Pat. No. 7,767,886, which is a Continuation-in-Part of U.S. patent application Ser. No. 10/451,366, filed Dec. 23, 2003, now abandoned, which was filed as a '371 National Stage of International Application No. PCT/JP02/04092, filed Apr. 24, 2002, which was not filed in English under PCT Article 21(1), and which claims priority of Japanese Application Nos. 2001-128008 filed Apr. 25, 2001, 2001-202082 filed Jul. 3, 2001, and 2002-20083 filed Jan. 29, 2002. The disclosure of each of these applications is incorporated by reference herein in its entirety.

TECHNICAL FIELD

The present invention relates to a gene involved in restoration from cytoplasmic male sterility to fertility. More specifically, the present invention relates to the gene involved in restoration of cytoplasmic male sterility character (hereafter may be abbreviated to cms) used for developing a cultivar of a first filial hybrid (hereafter abbreviated to $F_1$), and a vector and a transformant containing the gene.

BACKGROUND ART

As to crops such as cereal crops and vegetables, $F_1$ cultivars are being actively developed with features such as 1) an agricultural genetic character improved excellently by heterosis, 2) an equal quality of harvests, and 3) protectability of a breeder's right on the basis of segregation of genetic characters in the next generation. Actually, $F_1$ varieties of many major crops have gone into actual use.

A method for seed product ion of an $F_1$ cultivar is exemplified by cms/Rf seed production system comprising a cytoplasmic male sterile (cms) line and a line (hereafter may be abbreviated to Rf) for restoration from male sterility of the cultivar. For example, the method has been developed for cereals such as rice, Sorghum, and corn and an oil crop such as sunflower. These method have been developed by using a technique of breeding or cell fusion.

For Brassicaceae, the system for $F_1$ seed production by applying self-incompatibility is widely applied. For rapeseed showing unstable self-incompatibility, however, the system for $F_1$ seed production requires use of the cms line and the Rf line.

On the contrary, in recent years, a study has been conducted for using cytoplasmic male sterile line (Kosena cms) derived from Kosena radish and cytoplasmic male sterile line (Ogura cms) derived from Ogura radish for rapeseed. Both cms genes are encoded in a genome of mitochondria which is a cytoplasmic organelle, and their nucleotide sequences have been known. However, a molecular biological study using radish has not so developed and therefore, markers necessary for gene isolation have been seldom known. Thus, isolation of the gene from a nucleus is difficult. Therefore, introduction of the Rf gene has been achieved only for rapeseed by applying intergeneric crosses or cell fusion approaches to a radish line, of which fertility has been restored.

Furthermore, for Rf gene, 1 or more restorer genes are present according to each cms line of different plant species. For radish, the presence of Rf1 gene and Rf2 gene is necessary for restoration of fertility. In addition, it has been known that Rf1 gene reduces remarkably the accumulation of ORF 125 protein (M. Iwabuchi et al., Plant Mol. Biol. 39: 183-188. 1999) in mitochondria which is known as a cms-associated protein of radish (Jpn. J. Breeding 47 (separate volume 1): p. 186. 1997 and Jpn. J. Breeding 48 (separate volume 1): p. 197. 1998.)

In rapeseed, it has been also known by gene analysis study that radish Rf1 gene introduced by intrgeneric crosses or cell fusion reduces accumulation of ORF125 or ORF 138 protein (M. Grelon et al., Mol. Gen. Genet. 243: 540-547) which is known as the cms-associated protein, and that reduction of accumulation of these ORF 125 or ORF 138 protein coincides perfectly with fertility restoration phenomenon (N. Koizuka et al, Theor. Appl. Genet. 100: 949-955. 2000). The restoration of fertility of the male sterile line of rapeseed requires reduction of accumulation of the ORF 125 or ORF 138 protein. For this, Rf1 gene is an important gene.

However, concerning a nucleotide sequence of Rf genes, only Rf2 gene, which is a restorer gene for a T-cytoplasm which is one of maize cms, was identified and isolated. But no nucleotide sequence of Rf genes of other plant species has been known.

DISCLOSURE OF THE INVENTION

It has been known that, the rapeseed restorer line in which Rf1 gene derived from Ogura radish has been introduced by intergeneric hybridization or cell fusion, and the $F_1$ cultivar created by using the line as a pollen parent, shows a higher content of glucosinolate (hereafter abbreviated to GSL) than the regulated value, thereby making a practical problem. This may be because the gene derived from radish which is involved in GSL biosynthesis is present around Rf1 gene so as to make a tight genetic linkage and therefore the GSL content of the rapeseed restorer line (Rf line) increases. It has been known that GSL is contained in rapeseed expel and when given to an animal as a feed, it causes thyroid gland. Therefore, the GSL content of the rapeseed should be lower than a standard value. A rapeseed cultivar satisfying this standard is named Canola in Canada. The standard of Canola is that GSL content is 30 micromole/g seed. However, the standard value at registration of the cultivar is stricter. The standard value which is requireed at registration somewhat differs between states. For example, the GSL content at cultivar registration which is designated by Canola Council Canada is 12 micromole/g seed or lower. In France, the GSL content is 18 micromole/g seed or lower (In: Procedure of the Western Canada canola/rapeseed recommending committee incorporated for the evaluation and recommendation for registration of canola/rapeseed candidate cultivars in Western Canada: p 6, 1996).

Moreover, in recent years, a plant to which a function such as herbicide tolerance is added by gene recombination is being actively developed. For creating efficiently these plants, only the presence of the rapeseed restorer line yielded by breeding or cell fusion is insufficient, and isolation of Rf gene, particularly Rf1 gene derived from radish, has been desired.

Thus, a problem to be solved by the present invention is to isolate Rf gene, particularly Rf1 gene derived from radish, and identify its structure. A further problem to be solved by the present invention is to provide a means for establishing the rapeseed restorer line by using the Rf gene isolated.

As the result of the intensive study on solving the above problems, the present inventors successfully achieved the cloning of Rf1 genes derived from rapeseed and radish, thereby solving the problems.

Thus, the present invention provides a protein involved in restoration from sterility of a cytoplasmic male sterile individual to fertility which has 14 or more pentatricopeptide repeat (hereafter may be abbreviated to PPR) motifs, wherein a group of the motifs is divided into 3 or more blocks, each of the individual blocks has at least 2 or more PPR motifs, and the block in a carboxyl terminal (C terminal) side has 4 PPR motifs.

Preferred embodiments of an above protein provide:
the protein wherein the number of PPR motifs is 14 to 16;
the protein wherein the PPR motif group is divided into 3 blocks and each block has 5, 7, and 4 PPR motifs in the order from an amino terminal (N terminal);
the protein wherein the fourth amino acid located in a second PPR motif from the amino terminal (N terminal) is an amino acid other than serine, threonin and cysteine;
the protein wherein the fourth amino acid located in a second PPR motif from the amino terminal (N terminal) is any one of asparagine, glutamine, aspartic acid, glutamic acid or histidine; and
the protein which futher has a signal peptide sequence to translocate to a mitochondrion at the amino terminal or has a sequence of -LysAspGluLeu- at the carboxyl terminal.

Another aspect of the present invention provides a protein involved in restoration of the cytoplasmic male sterile individual to fertility, which causes gel shift of a transcriptional product after contacting to the transcriptional product of a cytoplasmic male sterile gene.

A still another aspect of the present invention provides:
a protein involved in restoration of the cytoplasmic male sterile individual to fertility, which has an amino acid sequence of SEQ ID NO. 26;
a protein involved in restoration of the cytoplasmic male sterile individual to fertility, which has an amino acid sequence of SEQ ID NO. 27;
a protein involved in restoration of the cytoplasmic male sterile individual to fertility, which has an amino acid sequence of SEQ ID NO. 28; and
a protein involved in restoration of the cytoplasmic male sterile individual to fertility, which has an amino acid sequence of SEQ ID NO. 29.

A still another aspect of the present invention provides any of the following proteins:
(1) a protein having a sequence from 80th to 687th amino acids of an amino acid sequence of SEQ ID NO. 3, the sequence from 80th to 687th amino acids of an amino acid sequence of SEQ ID NO. 17, or the sequence from 82nd to 690th amino acids of an amino acid sequence of SEQ ID NO. 19; or
(2) a protein which has an amino acid sequence wherein 1 or a plurality of amino acids are deleted, added, and/or substituted, in the sequence from 80th to 687th amino acids of an amino acid sequence of SEQ ID NO. 3, the sequence from 80th to 687th amino acids of the amino acid sequence of SEQ ID NO. 17, or the sequence from 82nd to 690th amino acids of an amino acid sequence of SEQ ID NO. 19, and is involved in restoration of the cytoplasmic male sterile individual to fertility.

A still another aspect of the present invention provides any of the following proteins:
(1) a protein having an amino acid sequence of SEQ ID NO. 3, SEQ ID. 17, or SEQ ID NO. 19; or
(2) a protein which has an amino acid sequence wherein 1 or a plurality of amino acids are deleted, added, and/or substituted, in the amino acid sequence of SEQ ID NO. 3, SEQ ID NO. 17, or SEQ ID NO. 19, and is involved in restoration of the cytoplasmic male sterile individual to fertility.

Preferably in the present invention, the cytoplasmic male sterile individual has a cytoplasmic male sterile gene of Kosena radish and/or Ogura radish or a homologue thereof.

A still another aspect of the present invention provides a DNA encoding any one of proteins of the present invention described above.

A still another aspect of the present invention provides:
a DNA having a nucleotide sequence of SEQ ID NO. 22;
a DNA having a nucleotide sequence of SEQ ID NO. 23;
a DNA having a nucleotide sequence of SEQ ID NO. 24; and
a DNA having a nucleotide sequence of SEQ ID NO. 25.

A still another aspect of the present invention provides any of the following DNAs:
(1) a DNA having a nucleotide sequence of SEQ ID NO. 2, SEQ ID NO. 16, or SEQ ID NO. 18; or
(2) a DNA which has a nucleotide sequence wherein 1 or a plurality of nucleotides are deleted, added, and/or substituted, in the nucleotide sequence of SEQ ID NO. 2, SEQ ID NO. 16, or SEQ ID NO. 18, and is involved in restoration of the cytoplasmic male sterile individual to fertility; or
(3) a DNA which hybridizes with a DNA having a nucleotide sequence of SEQ ID NO. 2, SEQ ID NO. 16, and SEQ ID NO. 18 under a stringent condition and is involved in restoration of the cytoplasmic male sterile individual to fertility.

A still another aspect of the present invention provides any of the following DNAs:
(1) a DNA having a sequence from 3754th to 8553th nucleotides of the nucleotide sequence of SEQ ID NO. 1 or a sequence from 812th to 3002th nucleotides of the nucleotide sequence of SEQ ID NO. 15; or
(2) a DNA which has a nucleotide sequence wherein 1 or a plurality of nucleotide are deleted, added, and/or substituted, in the sequence from 3754th to 8553th nucleotides of the nucleotide sequence of SEQ ID NO. 1, or a sequence from 812th to 3002th nucleotides of the nucleotide sequence of SEQ ID NO. 15, and is involved in restoration of the cytoplasmic male sterile individual to fertility; or
(3) a DNA which hybridizes with a DNA having a sequence from 3754th to 8553th nucleotides of the nucleotide sequence of SEQ ID NO. 1 or a sequence from 812th to 3002th nucleotides of the nucleotide sequence of SEQ ID NO. 15 under a stringent condition, and is involved in restoration of the cytoplasmic male sterile individual to fertility.

A still another aspect of the present invention provides any of the following DNAs:
(1) a DNA having a nucleotide sequences of SEQ ID NO. 1 or 15; or
(2) a DNA which has a nucleotide sequence wherein 1 or a plurality of nucleotides are deleted, added, and/or substituted in the nucleotide sequence of SEQ ID NO. 1 or SEQ ID NO. 15, and is involved in restoration of the cytoplasmic male sterile individual to fertility; or
(3) a DNA which hybridizes with a DNA having a nucleotide sequence of SEQ ID NO. 1 or SEQ ID NO. 15 under a stringent condition, and is involved in restoration of the cytoplasmic male sterile individual to fertility.

Preferably in the present invention, the cytoplasmic male sterile individual has a cytoplasmic male sterile gene of Kosena radish and/or Ogura radish or a homologue thereof.

A still another aspect of the present invention provides a vector containing DNA of the present invention.

A still another aspect of the present invention provides a transformant having DNA of the present invention or vector of the present invention. The transformant is preferably a transformed plant.

A still another aspect of the present invention provides a method for the restoration of the cytoplasmic male sterile individual to fertility wherein DNA of the present invention is used.

A still another aspect of the present invention provides a transformant having a cytoplasmic male sterile gene wherein a partial or full length of DNA of the present invention is introduced with an induction type promoter to a cell having DNA of the present invention, so that the transformant can regulate an expression of the cytoplasmic male sterile gene.

A still another aspect of the present invention provides a method for maintaining the cytoplasmic male sterile line by using the transformant described above.

A still another aspect of the present invention provides a method for detecting a gene involved in restoration from the cytoplasmic male sterile, wherein 15 to 50mer oligonucleotide primer freely designed from the above DNA of the present invention or probe of at least 15 mer consisting of all or a part of the above DNA of the present invention is used, and the quantity of the nucleotide sequence amplified by the primer or the quantity of the nucleotide sequence detected by the probe in an organism sample of interest is confirmed to be 1 gene or more in 1 genome.

A still another aspect of the present invention provides a promoter DNA having a sequence from 3754th to 5091th nucleotides of a nucleotide sequence of SEQ ID NO. 1 or a sequence from 1st to 811th nucleotides of a nucleotide sequence of SEQ ID NO. 15.

A still another aspect of the present invention provides a plant-transforming vector which comprises a promoter DNA having an ability of transcribing an mRNA at least in an anther and the DNA of the present invention.

Preferably, the promoter DNA having an ability of transcribing an mRNA in an anther is a promoter DNA having 3754th to 5091st nucleotide sequence of the nucleotide sequence of SEQ ID NO. 1 or 1st to 811st nucleotide sequence of the nucleotide sequence of SEQ ID NO. 15.

A still another aspect of the present invention provides a transformed plant having the vector of the present invention.

A still another aspect of the present invention provides the transformant or transformed plant of the present invention which has DNA encoding a protein involving in restoration of a cytoplasmic male sterile plant to fertility as a homozygote.

A still another aspect of the present invention provides the transformant or transformed plant of the present invention, wherein, when the transformant or the transformed plant is regenerated, the regenerated individual can restore the cytoplasmic male sterility to fertile.

A still another aspect of the present invention provides a seed, pollen, protoplast, cell, vegetative portion, hypocotyl, gamete or root, which is obtained from the transformant or transformed plant of the present invention.

A still another aspect of the present invention provides a transformant of a *Brassica* plant, wherein a glucosinolate content in the seed which is obtained from the transformant of the present invention being a transformant of the *Brassica* plant or from the transformed plant of the present invention satisfies the Canola standard.

A still another aspect of the present invention provides a seed which is obtained from the transformant of the *Brassica* plant of the present invention.

A still another aspect of the present invention provides a method for producing a hybrid plant seed having fertility restoration ability, wherein a cytoplasmic male sterile line plant is used as a mother, the transformed plant of the present invention as a fertility restoring line plant is used as a pollen parent, and both of them are crossed.

Preferably in the method for producing a hybrid plant seed, the cytoplasmic male sterile line plant is a cytoplasmic male sterile hybrid line derived from Ogura or Kosena radish.

A still another aspect of the present invention provides a hybrid plant seed which is produced by the method of the present invention.

Preferably, the plant belongs to the genus *Brassica*.

A still another aspect of the present invention provides the seed of the plant belonging to the genus *Brassica* according to the present invention, wherein a glucosinolate content in the seed satisfies the Canola standard.

A still another aspect of the present invention provides a method for producing seed oil, wherein the plant seed of the present invention is inseminated, a seed is collected from the grown plant, and an oil is collected from the collected seed.

A still another aspect of the present invention provides a seed oil which is produced by the method of the present invention.

A still another aspect of the present invention provides a seed, pollen, protoplast, cell, vegetative portion, hypocotyl, gamete or a root, which is obtained by planting and growing the hybrid plant seed of the present invention.

Lane 1: control vector; lane 2: transformed rapeseed; lane 3: cytoplasmic male sterile rapeseed,
  a: 3186 bp to 3753 bp, length: 568 bp,
  b: 4869 bp to 5112 bp, length: 244 bp,
  c: 7766 bp to 8250 bp, length: 485 bp.

Figure 4:
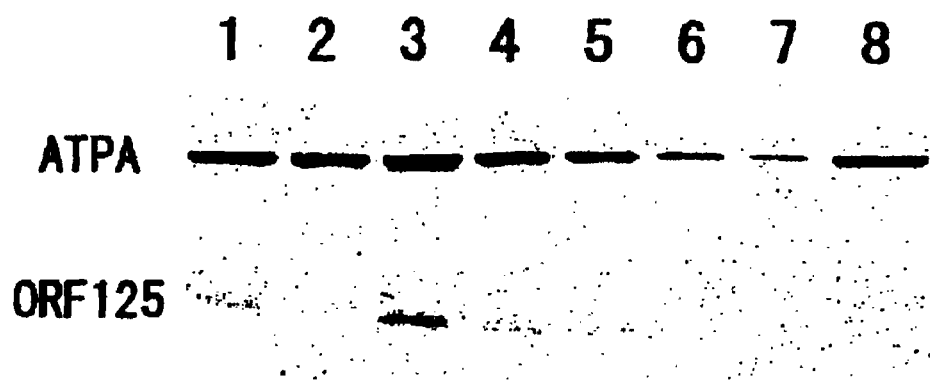
Figure 5:
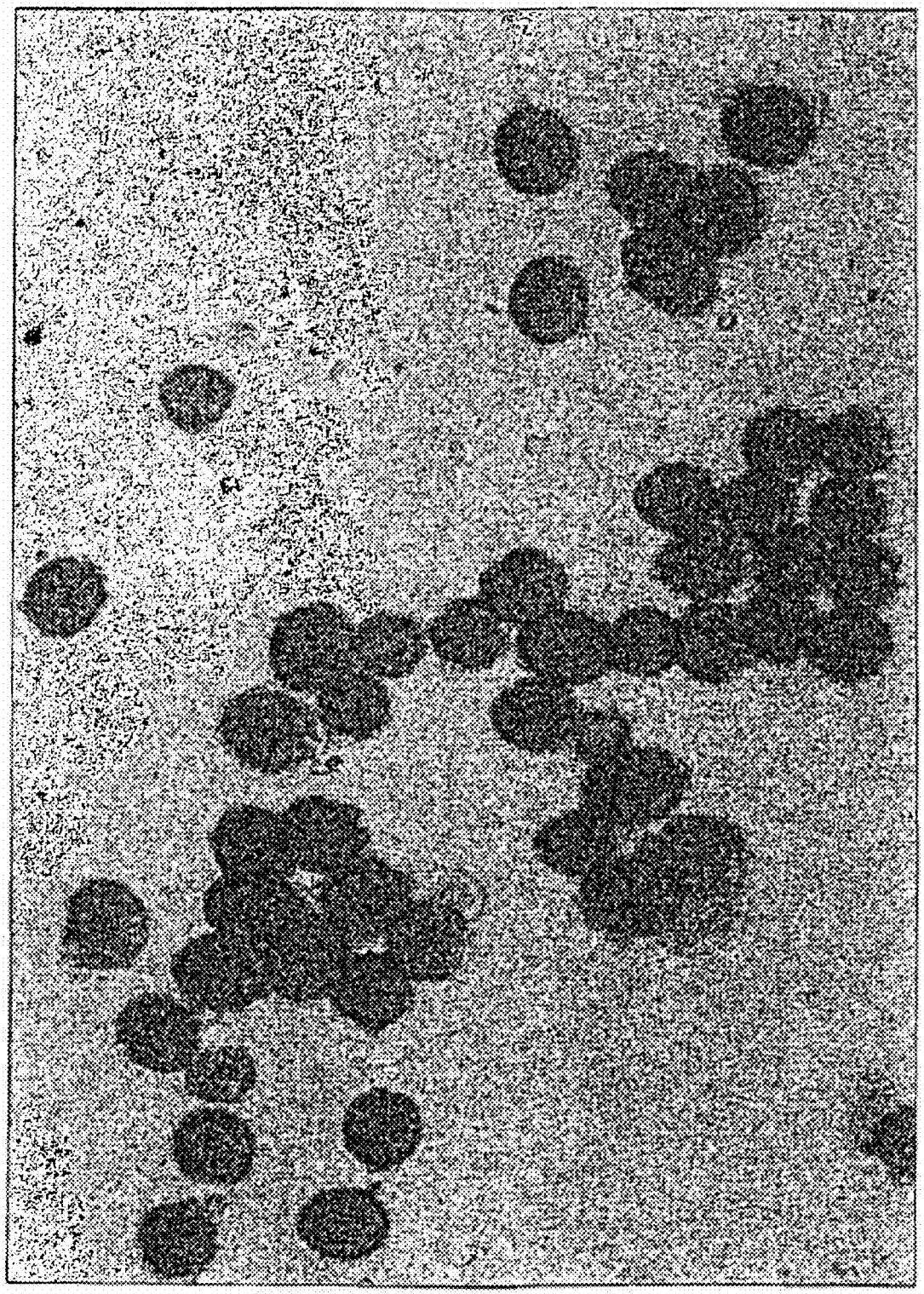

FIG. 4 shows a result of Western Blotting analysis of reduction of accumulation of ORF125 which is a CMS protein in the transformant:

Lane 1: cytoplasmic male sterile rapeseed -1-15 µg;
Lane 2: fertility restored rapeseed 15 µg;
Lane 3: cytoplasmic male sterile rapeseed -2-15 µg;
Lane 4 to 7: cytoplasmic male sterile rapeseed -2-, Dilution series: 15/2 µg, 15/4 µg, 15/8 µg, and 15/16 µg;
Lane 8: transformed rapeseed 15 µg;

FIG. 5 shows a result of microscopic observation of an pollen grains taken from a flowered plant of transformed rapeseed.

FIG. 6 shows the nucleotide sequence of pSTV125-5' #LA6 and pSTV125-5' #LA12.

Figure 7:
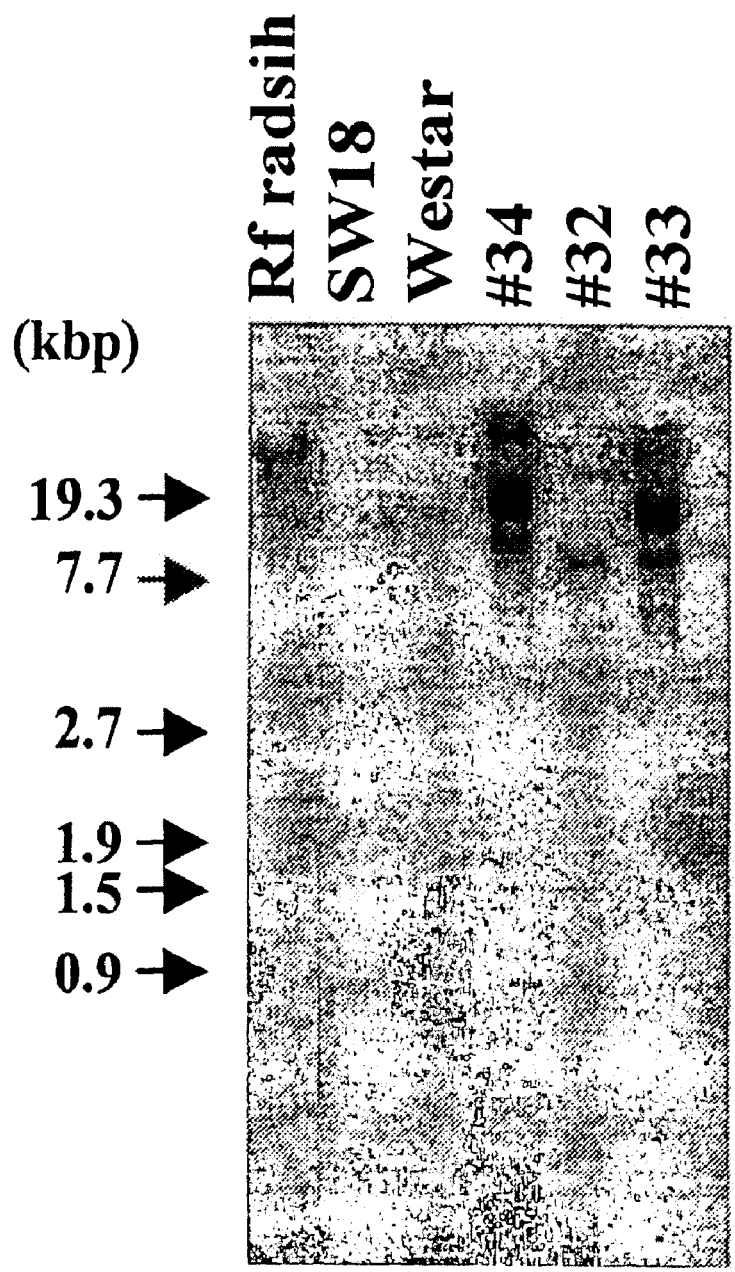

FIG. 7 shows Southern blot analysis of a radish Rf gene in fertility restored transgenic *Brassica napus* plants.

Figure 8:
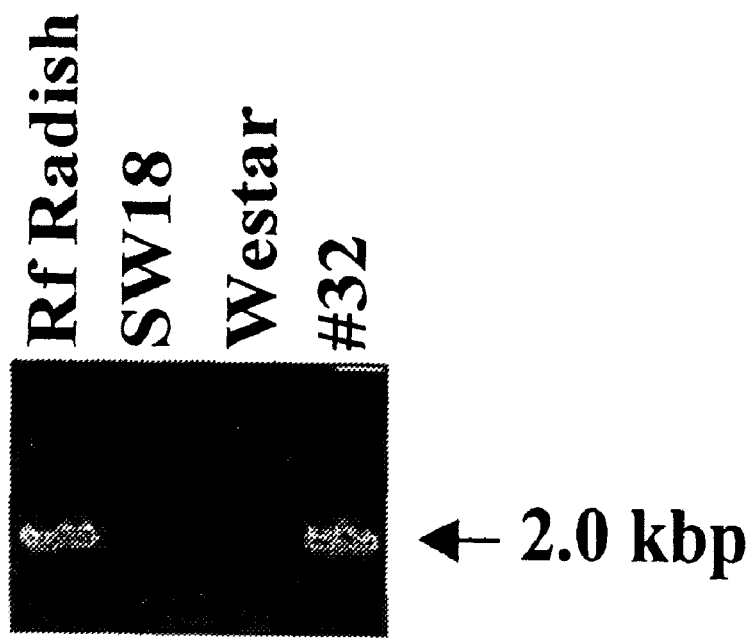

FIG. 8 shows RT-PCR analysis of a radish Rf gene in transgenic *Brassica napus* plant.

Figure 9:
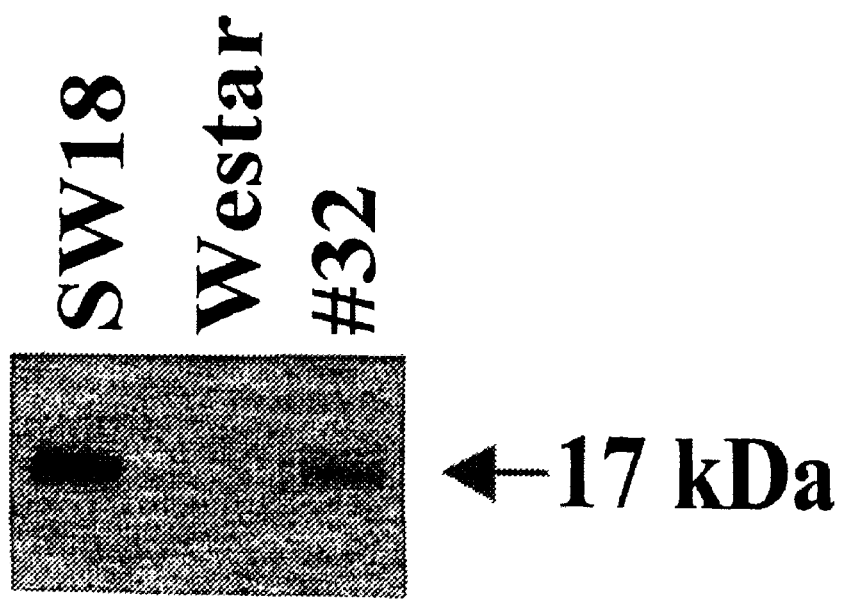

FIG. 9 shows Western blotting of ORF125 protein in transgenic *Brassica napus* plant.

Figure 10:
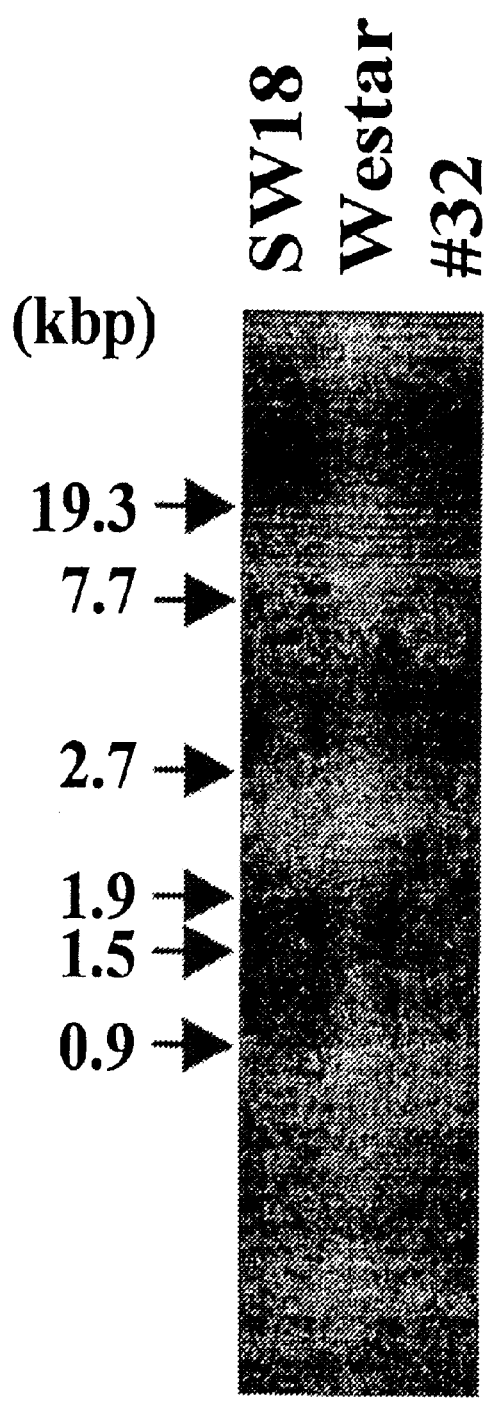

FIG. 10 shows Southern blot analysis of orf125 locus transgenic *Brassica napus* plant.

Figure 11:
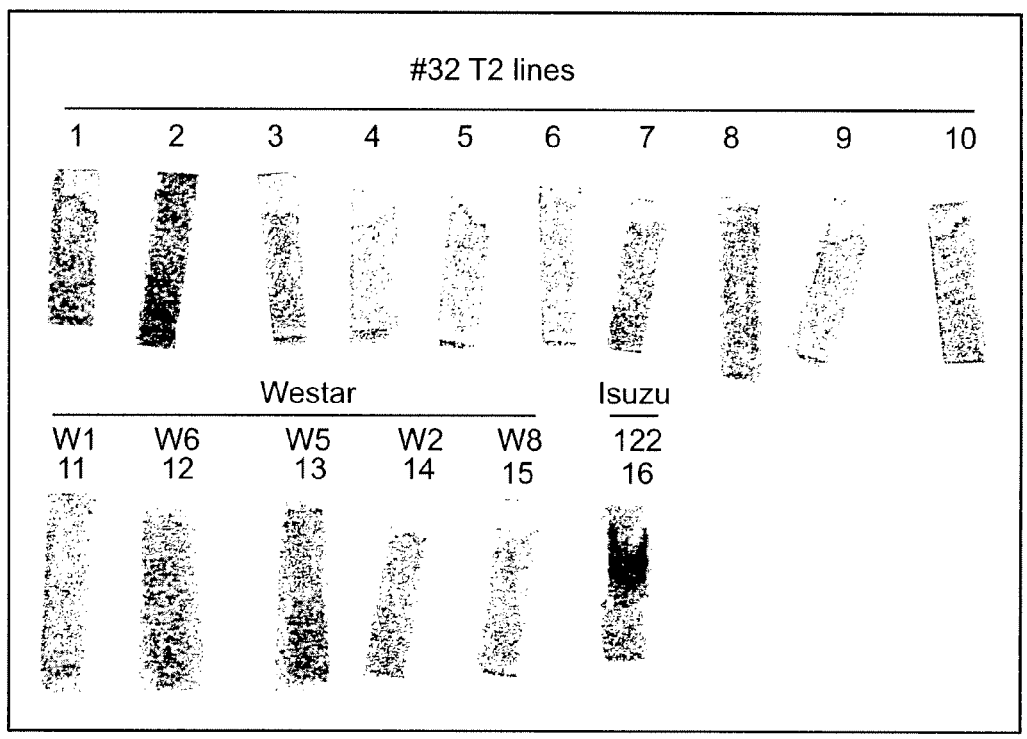

FIG. 11 shows seed glucosinolate analysis with test paper containing glucose oxidase/peroxidase.

THE BEST MODE FOR CARRYING OUT THE INVENTION

Embodiments of the present invention will be described below in detail.

(1) Embodiments of the Protein of the Present Invention

The protein of the present invention relates to any of proteins of (i) to (v) below:
(i) a protein involved in restoration of a cytoplasmic male sterile individual to fertility which has 14 or more pentatricopeptide repeat (hereafter may be abbreviated to PPR) motifs, wherein a group of the motifs is divided into 3 or more blocks, each of the individual blocks has at least 2 or more PPR motifs, and the block in a carboxyl terminal (C terminal) side has 4 PPR motifs.
(ii) a protein involved in restoration of the cytoplasmic male sterile individual to fertility, which causes gel shift of a transcription product after contacting to the transcription product of a cytoplasmic male sterile gene.
(iii) a protein involved in restoration of the cytoplasmic male sterile individual to fertility, which has an amino acid sequence of any of SEQ ID NOS. 26 to 29;
(iv) a protein of any of the followings:
(1) a protein having a sequence from 80th to 687th amino acids of an amino acid sequence of SEQ ID NO. 3, the sequence from 80th to 687th amino acids of an amino acid sequence of SEQ ID NO. 17, or the sequence from 82nd to 690th amino acids of an amino acid sequence of SEQ ID NO. 19; or
(2) a protein which has an amino acid sequence wherein 1 or a plurality of amino acids are deleted, added, and/or substituted, in the sequence from 80th to 687th amino acids of an amino acid sequence of SEQ ID NO. 3, the sequence from 80th to 687th amino acids of the amino acid sequence of SEQ ID NO. 17, or the sequence from 82nd to 690th amino acids of an amino acid sequence of SEQ ID NO. 19, and is involved in restoration of the cytoplasmic male sterile individual to fertility; and
(v) a protein of any of the followings:
(1) a protein having an amino acid sequence of SEQ ID NO. 3, SEQ ID. 17, or SEQ ID NO. 19; or
(2) a protein which has an amino acid sequence wherein 1 or a plurality of amino acids are deleted, added, and/or substituted, in the amino acid sequence of SEQ ID NO. 3, SEQ ID NO. 17, or SEQ ID NO. 19, and is involved in restoration of the cytoplasmic male sterile individual to fertility.

In the present specification, the PPR motif is the "pentatricopeptide repeat" motif. This PPR motif is a motif structure of a novel protein found in the course of an Arabidopsis genome project. The base motif thereof is that a sequence of 35 degenerated amino acids is repeated in tandem on a primary structure of the protein. The PPR motif has the sequence represented by amino terminal (N terminal)-"VTYNTLISGYCKNGKLEEALELFEEMKEKGIKPDV"-carboxyl terminal (C terminal) as a consensus amino acid sequence. This motif is the proposed by Small and Peeters (reference: Trends Biochem. Sci. 2000, 25 46-47). In the year of the publication of the reference, about 200 genes capable of having this motif in the Arabidopsis genome were registered to a gene bank such as GenBank (http://www.ncbi.nlm.nih.gov/GenBank/index.html.) At present, possibility of presence of this motif structure in a certain protein can be easily determined by a program stored in Protein Families Database of Alignments and HMNs (hereafter abbreviated to Pfam; http://www.sanger.ac.uk/Software/Pfam/search.shtml) located in Sanger Institute, U.K.

Up to now, there are following examples of proteins having the PPR motif of which function has been known: 1) Yeast PET309 and *Neurospora crassa* CYA-5 which are proteins translocating to mitochondria, interacts with coxI mRNA which is a mitochondrial gene to regulate coxI expression at a level of post-transcriptional processing or translation (Manthey and McEwen EMBO J 1995 14 4031, Coffin et al. Curr Genet 1997 32 273-280); and 2) Maize CRP1 which is a PPR motif protein translocating to mitochondrion, is essential for translation of petA and petD gene which is a chloroplast gene and also essential for a processing step of petD mRNA (Fisk et al. EMBO J 1999 18 2621-2630) Hence, the proteins having the PPR motif may highly probably contribute to translation regulation in some manner.

At this time, the inventors have isolated a gene involved in restoration of a cytoplasmic male sterile individual of Kosena radish to fertility, and have found that the protein encoded thereby has 14 or more pentatricopeptide repeat (hereafter abbreviated to PPR) motifs, the PPR motif group is divided into 3 or more blocks, each of the individual blocks has at least 2 or more PPR motifs, and the block located in a position nearest to the carboxyl terminal (C terminal) has 4 PPR motifs.

The above mentioned protein involved in restoration of a cytoplasmic male sterile individual to fertility is preferably one wherein the number of PPR motifs is 14 to 16, and more preferably one wherein the PPR motif group is divided into 3 blocks and each block has 5, 7, and 4 PPR motifs in the order from an amino terminal (N terminal).

Specifically, the protein comprises:
(1) PPR cluster #1: the PPR cluster in which the first to fifth PPR motifs from the N terminal comprises consecutive 175 residues;
(2) PPR cluster #2: the PPR cluster in which the sixth to 12th PPR motifs from the N terminal comprises consecutive 245 residues;
(3) PPR cluster #3: the PPR cluster in which the 13th to 16th PPR motifs from the N terminal comprises consecutive 140 residues.

More preferably, the fourth amino acid, which is present in the second PPR motif from the amino terminal (N terminal) side, is an amino acid other than serine, threonine, or cysteine. More preferably, the fourth amino acid, which is present in the second PPR motif from the amino terminal (N terminal) side, is any of asparagine, glutamine, aspartic acid, glutamic acid, or histidine. Particularly preferably, the fourth amino acid, which is present in the second PPR motif from the amino terminal (N terminal) side, is asparagine.

It has been known that normally, fertility restorer gene is present in a nuclear genome and the cytoplasmic male sterile gene is present in the mitochondria. Therefore, the above protein involved in restoration of the cytoplasmic male sterile individual to fertility preferably further has a signal peptide sequence for the translocation to the mitochondrion in the amino terminal or has a sequence of Lys-Asp-Glu-Leu in the carboxyl terminal.

The signal peptide sequence at the N terminal for the translocation to the mitochondra is exemplified by those confirmed by a prediction program "TargetP" (http://www.cbs.dtu.dk/services/TargetP/) or the predicion program "Psort" (http://psort.nibb.ac.jp/) based on an algorithm of O. Emanuelsson (J. Mol. Biol. 300, 1005-1016. 2000). Example of the signal peptide include the signal peptide (MetAlaPheArgGlnThr-LeuSerIleArgSerArgLeuPheA-laArgArgAsnGlnProVal- TyrHisIleIleProArgGluSerAspHisGluArgAsp) of AtOXA1 gene of *Arabidopsis thaliana* (W. Sakamoto et al.: Plant Cell Physiol. 41: 1157-1163.) Among these peptides, a preferable amino acid sequence is exemplified by the sequence of 1st to 79th amino acids in the amino acid sequence of SEQ ID NO. 3, and particularly preferably, the sequence of 1st to 34th amino acids in the amino acid sequence of SEQ ID NO. 3.

The protein according to the present invention which is involved in restoration of the cytoplasmic male sterile individual to fertility is bound to the transcription product of the cytoplasmic male sterile gene so as to cause an inhibition of translation of the cytoplasmic male sterile gene, thereby achieving restoration of the cytoplasmic male sterile individual to fertility.

Examples of the transcriptional product of the cytoplasmic male sterile gene include the transcriptional product (mRNA) of each gene of ORF125 which is a causal protein causing Kosena cytoplasmic male sterility or ORF138 which is the causal protein causing Ogura cytoplasmic male sterility. Preferred examples include 5'-UTR (Bonhomme et al.; Mol. Gen. Genet. 235: 340-348. 1992) region of the gene.

Examples of the methods for confirming the binding to the transcriptional product of the cytoplasmic male sterile gene include a method in which the protein according to the present invention is added to mRNA of orf125 or orf138 which was artificially transcribed in vitro, followed by electrophoresis, so-called gel shift method. Practical operation may be carried out under a condition commonly applied as the gel shift method.

Another method is that a fused gene of ORF125 or ORF138 gene and a detectable reporter gene such as β-galactosidase or luciferase is expressed in *Escherichia coli* or the like, the protein of the present invention is added thereto, and the presence or absence of expression inhibition is observed.

Specifically, the fertility restorer gene of the nucleotide sequence of the SEQ ID NO. 2 is integrated in a vector for expression in a *Escherichia coli*, and a vector wherein 5'-UTR region and a coding region of 25 amino acids of orf125 are fused to lacZ gene is integrated in the *Escherichia coli*. These vectors are subjected to induction expression, expression of lacZ gene is suppressed only in the case where the expression vector in which the fertility restorer gene has been integrated is present, and thereby blue colonies of *Escherichia coli* becomes white in the presence of X-Gal. As described above, it can be confirmed that, by using a gene encoding the protein of the present application and performing the above-mentioned confirmation, the protein of the present invention has a function to restore the cytoplasmic male sterile individual from sterility to fertility by causing translation inhibition of the cytoplasmic male sterile gene.

The most preferable examples of the proteins of the present invention which are involved in restoration of the cytoplasmic male sterile individual to fertility, include proteins having an amino acid sequences having homology of 70% or higher, preferably 80% or higher, more preferably 90% or higher, and further preferably 92% or higher, still further preferably 95% or higher, particularly 97% or higher to the amino acid sequence of SEQ ID NOS. 26 to 29 which is the consensus sequence. The consensus sequence is exemplified by the amino acid sequence of SEQ ID NO. 26, preferably exemplified by the amino acid sequence of SEQ ID NO. 27 or 28, and particularly preferably exemplified by the amino acid sequence of SEQ ID NO. 29.

Preferable examples of the above mentioned proteins include:
(1) a protein having a sequence from 80th to 687th amino acids of an amino acid sequence of SEQ ID NO. 3, the sequence from 80th to 687th amino acids of an amino acid sequence of SEQ ID NO. 17, or the sequence from 82nd to 690th amino acids of an amino acid sequence of SEQ ID NO. 19; or
(2) a protein which has an amino acid sequence wherein 1 or a plurality of amino acids are deleted, added, and/or substituted, in the sequence from 80th to 687th amino acids of an amino acid sequence of SEQ ID NO. 3, the sequence from 80th to 687th amino acids of the amino acid sequence of SEQ ID NO. 17, or the sequence from 82nd to 690th amino acids of an amino acid sequence of SEQ ID NO. 19, and is involved in restoration of the cytoplasmic male sterile individual to fertility.

The examples of the proteins having a sequence for the translocation to mitochondria includes:
(1) a protein having an amino acid sequence of SEQ ID NO. 3, SEQ ID. 17, or SEQ ID NO. 19; or
(2) a protein which has an amino acid sequence wherein 1 or a plurality of amino acids are deleted, added, and/or substituted, in the amino acid sequence of SEQ ID NO. 3, SEQ ID NO. 17, or SEQ ID NO. 19, and is involved in restoration of the cytoplasmic male sterile individual to fertility.

The protein according to the present invention is the protein which can be involved in restoration of the cytoplasmic male sterile individual to fertility. More specifically, when the transformant plant (Rf line) to which DNA encoding the protein of the present invention has been introduced is crossed with an individual of the cytoplasmic male sterile line (cms line), $F_1$ seeds of which fertility have been restored can be obtained. Preferable examples of the above cms line individual include the plant to which the cytoplasmic male sterile gene of Kosena radish and/or Ogura radish has been introduced.

Preferred examples of the Rf line described above include a plant having the introduced Rf gene as a homozygote. By using this homozygous Rf line as a pollen parent of commercial seed production and cross this Rf line with a cms line, an $F_1$ cultivar can be obtained with 100% fertility restoration ability without segregation of the introduced gene in a posterity generation.

Japanese Patent Laid-open Publication No. 1-218530, and Sakai and Imamura, Somatic hybridization between Radish (*Raphanus sativus*) and rapeseed (*Brassica napus*), In: Biotechnology in Agriculture and Forestry, Vol. 27 Somatic hybridization in crop improvement. I (ed. by Y. P. S. Bajaj) Springer-Verlag Berlin Heidelberg, 1994, are referred to as to Kosena radish. Pelletier G. et al. Intergeneric cytoplasmic hybridization in cruciferae by protoplast fusion, Mol Gen Gent 191:244-250, 1983 is referred to as to Ogura radish.

The protein of the present invention can be isolated by screening by using the gel shift method as described above, and can be isolated or synthesized by using DNA of the present invention described later. Method for obtaining the protein of the present invention is described bellow.

(2) Embodiments of DNA of the Present Invention

The DNA of the present invention relates to DNA of any of the following (I) to (iv).
(i) DNA encoding the protein of the present invention described above;
(ii) DNA having a nucleotide sequence of any of SEQ ID NO. 22 to SEQ ID NO. 25;
(iii) DNA of any of the followings;
(1) DNA having a nucleotide sequence of SEQ ID NO. 2, SEQ ID NO. 16, or SEQ ID NO. 18; or (2) DNA which has a nucleotide sequence wherein 1 or a plurality of nucleotides are deleted, added, and/or substituted, in the nucleotide sequence of SEQ ID NO. 2, SEQ ID NO. 16, or SEQ ID NO. 18, and is involved in restoration of the cytoplasmic male sterile individual to fertility; or (3) a DNA which hybridizes with a DNA having a nucleotide sequence of SEQ ID NO. 2, SEQ ID NO. 16, and SEQ ID NO. 18 under a stringent condition and is involved in restoration of the cytoplasmic male sterile individual to fertility.

(iv) DNA of any of the followings:

(1) DNA having a sequence from 3754th to 8553th nucleotides of the nucleotide sequence of SEQ ID NO. 1 or a sequence from 812th to 3002th nucleotides of the nucleotide sequence of SEQ ID NO. 15; or (2) DNA which has a nucleotide sequence wherein 1 or a plurality of nucleotide are deleted, added, and/or substituted, in the sequence from 3754th to 8553th nucleotides of the nucleotide sequence of SEQ ID NO. 1, or a sequence from 812th to 3002th nucleotides of the nucleotide sequence of SEQ ID NO. 15, and is involved in restoration of the cytoplasmic male sterile individual to fertility; or (3) DNA which hybridizes with a DNA having a sequence from 3754th to 8553th nucleotides of the nucleotide sequence of SEQ ID NO. 1 or a sequence from 812th to 3002th nucleotides of the nucleotide sequence of SEQ ID NO. 15 under a stringent condition, and is involved in restoration of the cytoplasmic male sterile individual to fertility.

(v) DNA of any of the followings:

(1) DNA having a nucleotide sequences of SEQ ID NO. 1 or 15; or (2) DNA which has a nucleotide sequence wherein 1 or a plurality of nucleotides are deleted, added, and/or substituted in the nucleotide sequence of SEQ ID NO. 1 or SEQ ID NO. 15, and is involved in restoration of the cytoplasmic male sterile individual to fertility; or (3) DNA which hybridizes with a DNA having a nucleotide sequence of SEQ ID NO. 1 or SEQ ID NO. 15 under a stringent condition, and is involved in restoration of the cytoplasmic male sterile individual to fertility.

In this specification, the DNA of the present invention may also be referred to as the gene of the present invention.

The nucleotide sequence of SEQ ID NO. 1 is a genomic DNA nucleotide sequence of 8553 nucleotides, the nucleotide sequence of SEQ ID NO. 2 is a coding sequence obtained from SEQ ID NO. 1, and the nucleotide sequence of SEQ ID NO. 3 is an amino acid sequence which is encoded by the nucleotide sequence of SEQ ID NO. 2.

The nucleotide sequence of SEQ ID NO. 15 is a genomic DNA nucleotide sequence of 3306 bases, the nucleotide sequence of SEQ ID NO. 16 is a coding sequence obtained from SEQ ID NO. 15, and the nucleotide sequence of SEQ ID NO. 17 is an amino acid sequence which is encoded by the nucleotide sequence of SEQ ID NO. 16.

The expression "the nucleotide sequence in which 1 or a plurality of nucleotides are deleted, added, and/or substituted" in this specification means the nucleotide sequence in which any number, fow example from 1 to 20, preferably from 1 to 15, more preferably from 1 to 10, and further preferably from 1 to 5 of nucleotides are deleted, added, and/or substituted.

The expression "the amino acid sequence in which 1 or a plurality of amino acids are deleted, added, and/or substituted" in this specification means the amino acid sequence in which any number, for example from 1 to 20, preferably from 1 to 15, more preferably from 1 to 10, and further preferably from 1 to 5 of amino acids are deleted, added, and/or substituted.

The expression "DNA which hybridizes under a stringent condition" means the nucleotide sequence of DNA which is obtained using the DNA as a probe by colony hybridization method, plaque hybridization method, or Southern blot hybridization method. Example of such DNA is one which can be identified by using a filter prepared by fixing DNA or DNA fragment derived from a colony or a plaque, and performing hybridization at 65° C. in the presence of 0.7 to 1.0 M NaCl followed by washing the filter using 0.1 to 2×SSC solution (1×SSC is composed of 150 mM sodium chloride and 15 mM sodium citrate) at 65° C.

Hybridization can be carried out according to the method described in Molecular Cloning: A Laboratory Manual, 2nd Ed., Cold Spring Harbor Laboratory, Cold Spring Harbor, N.Y., 1989 (hereafter abbreviated to "Molecular Cloning 2nd Ed").

The DNA which hybridizes under a stringent condition is exemplified by the DNA having a certain or higher degree of homology to the nucleotide sequence of the DNA used as the probe. The term "a certain or higher degree of the homology" used herein is, for example, 70% or higher, preferably 80% or higher, more preferably 90% or higher, further preferably 93% or higher, particularly preferably 95% or higher, and most preferably 97% or higher. The DNA having a certain or higher degree of the homology used herein includes both of a polynucleotide showing homology as described above and the polynucleotide of a complementary strand thereof.

The DNA of present invention is DNA which can be involved in restoration of the cytoplasmic male sterile individual to fertility. More specifically, when the transformant plant (Rf line) to which DNA of the present invention has been introduced is crossed with the individual of the cytoplasmic male sterile line (cms line), F1 seed of which fertility has been restored can be obtained. Preferred examples of the aforementioned cms line individual include an individual to which the cytoplasmic male sterile gene of Kosena radish and/or Ogura radish has been introduced.

(3) Method for Obtaining DNA of the Present Invention

A method for obtaining DNA of the present invention is not particularly limited. On the basis of information of the nucleotide sequence of SEQ ID NO. 1 or SEQ ID NO. 2 disclosed in the present specification, and the amino acid sequence of SEQ ID NO. 3 or the PPR motif obtained based on the information of the amino acid sequence of SEQ ID NO. 3, and the amino acid sequence obtained by combining a mitochondrial transit sequence, DNA of the present invention can be isolated or synthesized by applying a common breeding technique and a common genetic engineering technique which are known to those skilled in the art.

Specifically, DNA of the present invention can be obtained from an appropriate plant origin in which the gene of the present invention is expressed, specifically a *Raphanus* plant including a cultivar and a relative species of radish, or other plants to which the genomic DNA containing the restorer gene is introduced from these plants by crossing or cell fusion techniques, more specifically *Raphanus* plants such as Kosena radish, Ogura radish, Yuanhong radish or cultivars derived from those radishes and relative species of these radish cultivars or *Brassica* plants to which the genomic DNA containing the cytoplasmic male sterility restorer gene of these plant species and cultivars is introduced from these plants by crossing or cell fusion techniques. The gene of the present invention can be isolated and obtained, for example, by isolating DNA markers locating around an Rf gene, preparing a genome map indicating a relationship between genetic distances of these DNA markers and the Rf gene, and applying positional cloning method (also called chromosome walking) of an Rf region while starting from the genome map.

This technique is started from finding an appropriate DNA marker on a genomic DNA and preparing the genome map by measuring the genetic distance of the Rf gene and the DNA markers. For the DNA markers which generally has some 100 bp length, the genome derived from a father should be distinguished from the genome derived from a mother. The DNA marker should localize a same chromosome as that of the gene, and markers of which a mode of inheritance is almost same as that of the gene due to a small distance from the gene, that is, a marker having a genetically tight linkage, is more desirable.

As method for isolating the DNA marker, RFLP method has been frequently used so far, however, simple and convenient methods such as RAPD method and AFLP (Amplified Fragment Length Polymorphism) method which use PCR, are recently used (Nucleic Acids Research, 1995, Vol. 23, NO. 21: 4407-4414). Particularly, AFLP method is effective means for obtaining the marker having the genetically tight linkage. As a material for measuring the genetic distance from the marker, there is normally used an $F_2$ population obtained by self pollination of an $F_1$ generation produced by crossing a recessive homozygous individual lacking the Rf1 gene with a dominant homozygous individual having homozygous Rf1 genes, and $BC_1$ population obtained by crossing the $F_1$ generation with the recessive homozygous plant, which is the parent thereof, lacking a gene of interest.

As the recessive homozygous individual as described above, the *Raphanus* plants including the cultivar and the relative species of radish of the cytoplasmic male sterile line, more specifically Kosena radish and Ogura radish of the cytoplasmic male sterile line, or *Brassica* plants to which the cytoplasmic male sterility derived from Kosena radish (Kosena cms) and the cytoplasmic male sterility derived from Ogura radish (Ogura cms) have been introduced, more specifically cms rapeseed can be used.

As the dominant homozygous plant described above, the *Raphanus* plants including the cultivar and the relative species of radish of the Rf line, more specifically *Brassica* plants, to which the genomic DNA containing the cytoplasmic male fertility restoration gene of Raphanus plants including Kosena radish, Ogura radish, Yuanhong radish or cultivars and relative species of these radish cultivars, which are the cytoplasmic male sterile line, has been introduced by crossing or cell fusion techniques, more specifically Rf rapeseed can be used.

For analysis of the $F_2$ population obtained by self pollination of the $F_1$ generation obtained by crossing of these parents and the $BC_1$ population obtained by crossing the $F_1$ generation with the recessive homozygous plant, normally 100 individuals or more and more preferably 1000 individuals or more are desirably used. The number of the individuals used as many as possible make accuracy of the genome map higher and a physical distance from the DNA marker to a gene of interest becomes short. Similarly in case of the Rf gene, the DNA marker having a shorter physical distance can be obtained.

Figure 1:
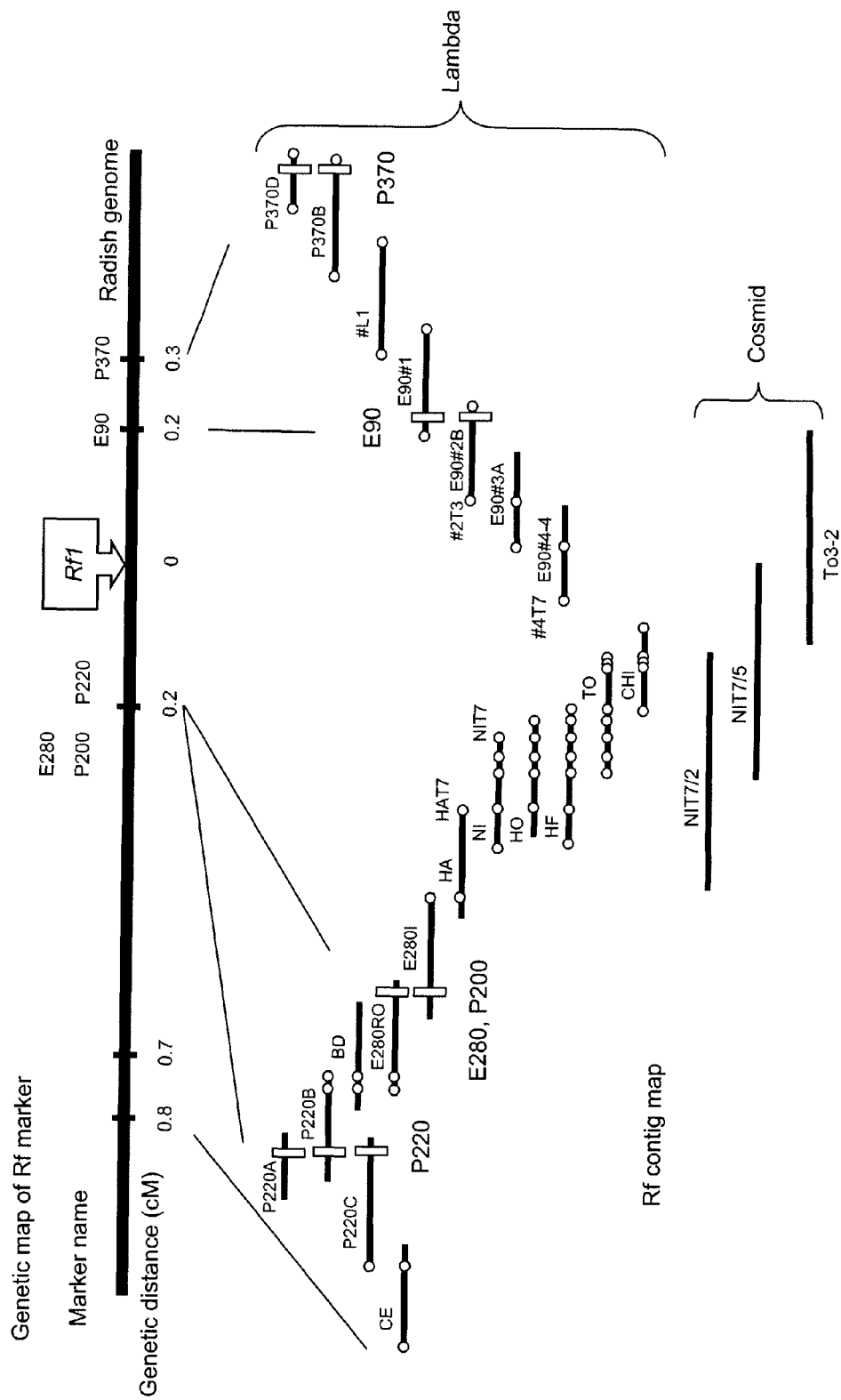
FIG. 1 shows a genetic map of Rf marker.

As the material for the measurement of the genetic distance of the DNA marker from the Rf gene, for example, there can be used $F_2$ population of some thousand individuals which is obtained by self pollination of the radish $F_1$ generation produced by crossing of Kosena radish (*Raphanus sativus* cv. Kosena) of the cms line with Yuanhong radish (*Raphanus sativus* cv. Yuanhong) of the Rf line according to the method described in N. Koizuka et al. (Teor. Appl. Genet. 100: 949-955, 2000). Analysis of these populations allows isolation of the DNA markers with a linkage in a form sandwiching the Rf gene and located in a position with a distance of about 0.2 cM from both sides thereof. By this step, the genome map as shown in FIG. 1, which shows the genetic distance of the marker from the Rf gene can be prepared.

Subsequent to preparation of the genome map, the genomic DNA which corresponds to its position should be cloned to combine between DNA markers sandwiching the objective gene. Normally, the physical distance between DNA markers and the objective gene is large and hence, combination of a plurality of clones having genomic DNA fragments allows covering a region from the DNA marker to the objective gene. A step to combine these DNA markers by using the clone having genomic DNA fragments is preparation of contig. For the Rf gene, contig can be similarly prepared by combining these DNA markers which is located in the position nearer the Rf gene by using a plurality of clones having genomic DNA fragments, so as to cover the Rf gene region.

A collection of clones having genomic DNA fragments can be obtained by preparing a genomic library. Normally, some kinds of vectors are used according to the length of the genomic DNA which can be cloned. Examples include those constructed by using a lambda phage vector which can clone a fragment having the length up to about 20 kb, a cosmid vector which can clone a fragment having a relatively long (up to 40 kb) length, a BAC (Bacterial Artificial Chromosome) vector which can clone a fragment having a longer (100 or more kb) length.

In any of libraries, it is important that a value produced by multiplying a number of populations of the library to an average length of the fragment cloned becomes the value 4 to 5 times a full length (genome size) of the genome supplied to the library. The genome size of radish may be about 500 Mbp and therefore, in case of the lambda phage vector having the average length of 20 kb, the number of population becomes $1.0 \times 10^5$ to $1.25 \times 10^5$ and in case of the cosmid library having the average length of 40 kb, the number of population becomes $5.0 \times 10^4$ to $6.25 \times 10^4$. The genome size of rapeseed is thought to be about 1000 Mbp and therefore, in case of the lambda phage vector having the average length of 20 kb, the number of population becomes $2.0 \times 10^5$ to $2.5 \times 10^5$, and in case of the cosmid library having the average length of 40 kb, the number of population becomes $1.0 \times 10^5$ to $1.25 \times 10^5$.

For the genomic DNA supplied to the library, the genomic DNA may be extracted from a living organism containing the objective gene by an ordinary method. In case of the Rf gene, there can be used the *Raphanus* plant including the cultivar and the relative species of radish of the Rf line, more specifically *Brassica* plants, to which the genomic DNA containing the cytoplasmic male fertility restorer gene of *Raphanus* plants including Kosena radish, Ogura radish, Yuanhong radish or varieties and relative species of these radish varieties, which are the cytoplasmic male sterile line, has been introduced by crossing or cell fusion techniques, more specifically Rf rapeseed. Generally, it may be most preferable to extract the genomic DNA from the same Rf line plant as the parent plant used for preparation of the $F_2$ population and the $BC_1$ population so as to prepare the genomic library. The genomic DNA can be prepared according to such ordinary method as CTAB method (Murray, M. G. and Thompson, W. F. (1980) Nucleic Acids Res. 8: 4321)

For the preparation of contig, the clone having DNA marker which is located in both sides of the Rf gene is first isolated. Isolation is carried out from the genomic library by the ordinary method using plaque hybridization method in case of a lambda phage library and by using colony hybridization method in case of cosmid library and BAC library. Next, using a terminal region of the clone isolated as an index, contig is prepared by isolating the clone located in an adjacent position of the clone. After preparation, the nucleotide sequence of the contig is determined by the ordinary method.

From the development of a genome project in recent years, a technique for presuming a functional gene on the basis of the nucleotide sequence of the genomic DNA has been advanced. A gene discovery program represented by "Genscan" can presume the gene in a considerable probability. In addition, a homology search program represented by "BLAST" can presume similarity to other genes and proteins. Using these analytical programs, presumption and isolation of the objective gene are carried out. In the case of Rf gene, similarly, the genomic DNA sequence of the contig can be isolated and identified by using a similar analytical software. Such analysis reveals a promoter region on a genomic DNA nucleotide sequence, a structural gene region containing an intron, and a terminator region. Also, concerning the structural gene containing the intron, the gene in a form which is translated into a protein from which the intron has been excluded and the amino acid sequence corresponding to the gene are clearly indicated. In such manner, the Rf gene on the contig can be presumed in a considerable probability.

Moreover, on the basis of the gene sequence presumed by using the analytical programs as described above, the actual form of in vivo expression of the objective genome can be confirmed by purifying an mRNA and isolating complementary DNA (cDNA) corresponding thereto. A starting site of transcription is conveniently confirmed by analysis applying easy 5'-RACE method employing PCR and more reliably, primer extension method and SI mapping method.

The methods mentioned above have been described in Molecular Cloning: A Laboratory Manual, 2nd Ed., Cold Spring Harbor Laboratory, Cold Spring Harbor, N.Y. 1989 and the like.

The genes of the present invention which was isolated on the basis of the nucleotide sequence presumed by the techniques as described above are exemplified by DNA of SEQ ID NO. 2, SEQ ID NO. 16, and SEQ ID NO. 18. Thus, on the basis of the DNA sequence, cDNA can be easily isolated from other plant origin by common genetic engineering technique.

Specifically, the cDNA corresponding to the gene of the present invention can be obtained from the appropriate plant origin in which the gene of the present invention is expressed, specifically the *Raphanus* plant including the cultivar and the relative species of radish or other plants, to which the genomic DNA containing the cytoplasmic male sterile restorer gene is introduced from these plants by crossing or cell fusion techniques, and more specifically *Raphanus* plants such as Kosena radish, Ogura radish, and Yuanhong radish or cultivars and relative species of these radish cultivars or *Brassica* plants, to which the genomic DNA containing the cytoplasmic male fertility restorer gene of these plant species and cultivars is introduced by crossing or cell fusion techniques, by preparing a cDNA library according to the ordinary method and selecting a desired clone from the library by using the appropriate DNA fragment specific to the gene of the present invention as the probe or by using an antibody against a translation product of the gene of the present invention.

In the above described procedure, an origin of the cDNA is exemplified by various cells and tissues which express the gene of the present invention and a cultured cell derived therefrom. Separation of total RNA, separation and purification of mRNA, and obtaining and cloning of cDNA from these cells and tissues can be carried out according to the ordinary method.

The method for screening the gene of the present invention from the cDNA library is not particularly limited, and can follow the ordinary method.

As the probe used herein, the DNA chemically synthesized on the basis of information concerning the nucleotide sequence of the gene of the present invention can be generally used, and the gene of the present invention and the fragment thereof already obtained can be preferably used. Moreover, a sense primer and an antisense primer, which have been designed on the basis of information of the nucleotide sequence of the gene of the present invention, can be also used as the probe for screening.

A nucleotide sequence of the sense primer and the antisense primer used as the above probe is a partial nucleotide sequence corresponding to the DNA which encodes the amino acid sequence of SEQ ID NO. 3, SEQ ID NO. 17, or SEQ ID NO. 19, which has at least 15 to 50 consecutive nucleotides and preferably 20 to 30 consecutive nucleotides. Alternatively, a positive clone itself having the sequence as described above can be used as the probe.

Obtaining the gene of the present invention may be carried out in combination of techniques ordinary used for isolation of the gene, such as DNA and RNA amplification technique by PCR method and the RACE method represented by 5'-RACE method.

The primer used for application of PCR method can be appropriately designed on the basis of information of the nucleotide sequence of the gene of the present invention which was revealed by the present invention, and can be synthesized by the ordinary method. Isolation and purification of the amplified DNA and RNA fragments can be carried out by the ordinary method as described above. For example, gel electrophoresis can be employed.

As for the gene or various DNA fragments of the present invention obtained by the above described procedures, the nucleotide sequence thereof can be determined according to the ordinary method.

By using partial or all nucleotide sequence of the gene of the present invention obtained by such procedure, the presence of the gene of the present invention and the occurrence of expression thereof in an individual or various tissues can be characteristically detected.

As described above, the gene of the present invention is exemplified by DNA encoding an amino acid sequence of SEQ ID NO. 3, SEQ ID NO. 17, or SEQ ID NO. 19, but is not limited thereto. Homologues of the gene are included in the present invention.

The homologues of the gene means a series of related genes which have a sequence homology with the gene (or a gene product thereof) of the present invention and are recognized as a gene family on the basis of a similarity of a structural feature as described above and a biological function thereof as described above. An allele of these gene is included.

For example, the gene of the present invention is not limited to the gene having a specific nucleotide sequence of SEQ ID NO. 1 or SEQ ID NO. 2, but can have the nucleotide sequence selected by combining optionally a codon corresponding to an individual amino acid residue shown by SEQ ID NO. 3. Similarly, the gene can have not only a specific nucleotide sequence of SEQ ID NO. 15 or SEQ ID NO. 16, but also can have the nucleotide sequence selected by combining with an optional codon corresponding to individual amino acid residues shown by SEQ ID NO. 17. The gene can have not only a specific nucleotide sequence of SEQ ID NO. 18, but also can have the nucleotide sequence selected by combining with an optional codon corresponding to individual amino acid residues shown by SEQ ID NO. 19. Selection of the codon can be carried out according to the ordinary method and for example, a frequency of codon use in a host used can be taken into account.

Further, as described above, the gene of the present invention includes DNA which hybridizes with DNA having a nucleotide sequence of SEQ ID NO. 1, SEQ ID NO. 2, SEQ ID NO. 15, SEQ ID NO. 16, SEQ ID NO. 18, or a part thereof under a stringent condition. Such DNA are DNA having a certain or higher degree of homology with DNA having the nucleotide sequence of SEQ ID NO. 1, SEQ ID NO. 2, SEQ ID NO. 15, SEQ ID NO. 16, SEQ ID NO. 18, or a part thereof.

The above described DNAs having a certain or higher degree of homology mean polynucleotides and polynucleotides of the complementary strand thereof having at least 70% degree of homology, preferably at least 90% degree of homology, more preferably at least 95% degree of homology, and most preferably at least 97% degree of homology with the nucleotide sequence of SEQ ID NO. 1, SEQ ID NO. 2, SEQ ID NO. 15, SEQ ID NO. 16, SEQ ID NO. 18, or a part thereof or the nucleotide sequence encoding amino acid sequences of SEQ ID NO. 3, SEQ ID NO. 17, or SEQ ID NO. 19, or a part thereof.

More specifically, the DNA having the nucleotide sequence which hybridizes with the DNA having a nucleotide sequence of SEQ ID NO. 1, SEQ ID NO. 2, SEQ ID NO. 15, SEQ ID NO. 16 or SEQ ID NO. 18 or a part thereof under the stringent condition of 0.2×SSC containing 0.1% SDS at 50° C. or 1×SSC containing 0.1% SDS at 60° C. can be exemplified.

Among the DNA of the present invention, particularly the followings can be prepared by any method known to those skilled in the art such as chemical synthesis, genetic engineering technique and mutagenesis:

DNA which has a nucleotide sequence wherein 1 or a plurality of nucleotides are deleted, added, and/or substituted in the nucleotide sequence or a part thereof of SEQ ID NO. 1 or SEQ ID NO. 15, and is involved in restoration of the cytoplasmic male sterile individual to fertility;

DNA which has a nucleotide sequence wherein 1 or a plurality of nucleotides are deleted, added, and/or substituted in the nucleotide sequence or a part thereof of SEQ ID NO. 2, SEQ ID NO. 16, or SEQ ID NO. 18, and is involved in restoration of the cytoplasmic male sterile individual to fertility; and DNA encoding a protein which has an amino acid sequence wherein 1 or a plurality of amino acids are deleted, added, and/or substituted in the amino acid sequence or a part thereof of SEQ ID NO. 3, SEQ ID NO. 17, or SEQ ID NO. 19, and is involved in restoration of the cytoplasmic male sterile individual to fertility. For example, by using DNA having a nucleotide sequence or a part thereof of SEQ ID NO. 1, SEQ ID NO. 2, SEQ ID NO. 15, SEQ ID NO. 16, or SEQ ID NO. 18, a mutated gene can be obtained by introducing mutation to these DNA.

As the method for obtaining a mutant gene, known methods such as random mutant, mutant with target, a method using a synthetic gene (Sin Idensi Kougaku Handbook. Zikken Igaku Sppl., Youdosya. 1996) can be employed.

Specifically, there can be used a method of contacting the DNA having the nucleotide sequence or a part thereof of SEQ ID NO. 1 or 2 with a drug which is a mutagen, a method for irradiating ultraviolet rays to the DNA, genetic engineering technique, and the like. Site-directed mutagenesis method which is one of genetic engineering technique is a useful technique since it can introduce a specific mutation to a specific site, and it can be carried out according to the method described in Molecular Cloning, 2nd edition.

(4) Vector Containing DNA of the Present Invention

DNA of the present invention can be used as a recombinant vector by introducing it in an appropriate vector. The type of the vector may be an expression vector or a non-expression vector and can be selected in accordance with the purpose.

A preferable cloning vector is that capable of autonomous replication in a K12 strain of *Escherichia coli*, and either a phage vector or plasmid vector can be used. The vector for expression in *Escherichia coli* may be used as the cloning vector. Specifically, the examples include ZAP Express (Strata Gene, Strategies, 5, 58 (1992),) pBluescrlpt II SK (+) (Nucleic Acids Research, 17, 9494 (1989)), Lambda ZAP II (Strata Gene), λ gt10, λgt11 (DNA Cloning, A Practical APPRoach, 1, 49 (1985)), λ TriplEx (Clonetec), λ ExCell (Pharmacia), pT7T318U (Pharmacia), pcD2 (Mol. Gen. Biol., 3, 280 (1983)), pMW218 (Wako Pure Chemicals), pUC118 (Takara), pEG400 (J. Bac., 172, 2392 (1990)), and pQE-30 (QIAGEN).

The expression vector can be selected in consideration of combination with the host, and preferably, a vector which is capable of autonomous replication in the host cell or integration into a chromosome and contains a promoter in a position which enable transcription of the gene of the present invention, is used.

In the case where a bacteria is used as the host cell, it is preferable that the expression vector for expression of DNA is capable of autonomous replication in the bacterial cell and also that it is a recombinant vector composed of the promoter, a ribosome binding sequence, the above DNA, and a transcription termination sequence. A gene for regulating the promoter may be contained.

As the expression vector for bacteria is exemplified by pBTrP2, pBTac1, pBTac2 (all commercialized by Boeringer Manheim), pKK233-2 (Pharmacia), pSE280 (Invitrogen), pGEMEX-1 (Promega), pQE-8 (QIAGEN), pQE-30 (QIAGEN), pKYP10 (Japanese Patent Laid-open Publication No. 58-110600), pKYP200 (Agrc. Biol. Chem., 48, 669 (1984)), PLSA1 (Agrc. Blol. Chem., 53, 277 (1989)), pGEL1 (Proc. Natl. Acad. Sci. USA, 82, 4306 (1985)), pBluescrlptII SK+, pBluescriptII SK(−) (Stratagene), pTrS30 (FERMBP-5407), pTrS32 (FERM BP-5408), pGEX (Pharmacia), pET-3 (Novagen), pTerm2 (U.S. Pat. No. 4,686,191, U.S. Pat. No. 4,939,094, U.S. Pat. No. 5,160,735), pSupex, pUB110, pTP5, pC194, pUC18 (Gene, 33, 103 (1985)), pUC19 (Gene, 33, 103 (1985)), pSTV28 (Takara), pSTV29 (Takara), pUC118 (Takara), pPA1 (Japanese Patent Laid-open Publication No. 63-233798), pEG400 (J. Bacteriol., 172, 2392 (1990)), and pQE-30 (QIAGEN). As the promoter for bacteria is exemplified by promoter derived from *Escherichia coli* and phage such as trp promoter (P trp), lacpromoter (P lac), PL promoter, PR promoter and PSEpromoter, as well as SP01promoter, SP02promoter, and penPpromoter.

As the expression vector for yeast is exemplified by YEp13 (ATCC37115), YEp24 (ATCC37051), Ycp5O (ATCC37419), pHS19 and pHS15. As the promoter for yeast is exemplified by PHO5promoter, PGKpromoter, GAPpromoter, ADHpromoter, gal1promoter, gal10promoter, heat shock protein promoter, and also promoters such as MF α1promoter and CUP1promoter.

As the expression vector for an animal cell is exemplified by pcDNAI, pcDM8 (commercialized by Funakoshi), pAGE107 (Japanese Patent Laid-open Publication No. 3-22979; Cytotechnology, 3, 133, (1990)), pAS3-3 (Japanese Patent Laid-open Publication NO. 2-227075), pCDM8 (Nature, 329, 840, (1987)), pcDNAI/AmP (Invitrogen), pREP4 (Invitrogen), pAGE103 (J. Biochem., 101, 1307 (1987)), and pAGE210. As the promoter for animal cell is exemplified by the promoter of IE (immediate early) gene of cytomegarovirus (human CMV), an early promoter of SV40, a retrovirus promoter, metallothionein promoter, heat shock promoter and SRα promoter.

As the expression vector for plant cell is exemplified by pIG121-Hm (Plant Cell Report, 15, 809-814 (1995)), pBT121 (EMBO J. 6, 3901-3907 (1987)), pLAN411 and pLAN421 (Plant Cell Reports 10 (1991) 286-290). When a long DNA fragment of 10 kb or longer is introduced to a plant, it is desired to use a vector which was improved so as to allow a stable hold and introduction of long strand DNA. For example, pBIBAC2 (Gene 200 (1997) 107-116), pYLTAC7 (PNAS 96 (1999) 6535-6540) and pBIGRZ2 (Bioscience and Industry 55 (1997) 37-39) are exemplified.

The promoter for plant cell is exemplified by cauliflower mosaic virus 35S promoter (Mol. Gen. Genet (1990) 220, 389-392). A detail of transformation of plant will be described later.

(5) Transformant Having DNA of the Present Invention

The transformant having DNA of the present invention can be prepared by introducing the above mentioned recombinant vector (preferably the expression vector) into a host.

Specific examples of the host cell of bacteria include microorganisms belonging to *Escherichia, Corynebacterium, Brevibacterium, Bacillus, Microbacterium, Serratia, Pseudomonas, Agrobacterium, Alicyclobacillus, Anabaena, Anacystis, Arthrobacter, Azobacter, Chromatium, Erwinia, Methylobacterium, Phormidium, Rhodobacter, Rhodopseudomonas, Rhodospirillum, Scenedesmun, Streptomyces, Synnecoccus* and *Zymomonas*. The method for introducing the recombinant vector to bacterial host is exemplified by a method using a calcium ion and a protoplast method.

Specific examples of a yeast host include *Saccharomyces cerevisae, Schizosaccharomyces pombe, Kluyveromyces lactis, Trichosporon pullulans*, and *Schwanniomyces alluvius*.

The method for introducing the recombinant vector into yeast host may be any method for introducing the DNA to the yeast, and examples thereof include electroporation method, spheroplast method, and lithium acetate method.

The host for the animal cell is exemplified by Namalva cell, COS1 cell, COS7 cells, and CHO cell.

As the method for introducing the recombinant vector to the animal cell, any method capable of introducing DNA to animal cell can be used. For example, electroporation method, calcium phosphate method and lipofection method can be used.

Transformant using the plant cell will be described later.

(6) Method for Obtaining the Protein of the Present Invention

The method for obtaining the protein of the present invention is not particularly limited. On the basis of information obtained by combining the amino acid sequence of SEQ ID NO. 3, SEQ ID NO. 17 or SEQ ID NO. 19 disclosed in the present specification or the PPR motif or the mitochondria transit sequence obtained on the basis of information of the amino acid sequence of SEQ ID NO. 3, SEQ ID NO. 17 or SEQ ID NO. 19, the protein of the present invention can be isolated, expressed or synthesized by applying the general genetic engineering technique known to those skilled in the art.

For example, the protein of the present invention can be expressed by isolating or synthesizing DNA encoding a protein of the present invention and introducing it into cell.

The protein of the present invention can be obtained by, for example, culturing a transformant having a gene of the present invention, producing and accumulating the protein of the present invention in the culture, and collecting the protein from the culture.

The method for culturing a transformant having a gene of the present invention can be carried out according to an ordinary method used for culturing the host.

In the case where the transformant of the present invention is a procaryote such as *Escherichia coli* or an eucaryote such as yeast, a culture medium for culturing these microorganisms may be either of natural medium or synthetic medium, so long as these culture media contains a carbon source, nitrogen source, inorganic salts which can be used by these microorganisms, and can realizes an efficient culturing of the transformant. Culturing is preferably carried out under an aerobic condition such as a shaking culture or an aerated and agitated submerged culture, a culture temperature ranges normally from 15 to 40° C., and culture duration time ranges normally from 16 hours to 7 days. The pH during the culture is kept ranging from 3.0 to 9.0. pH adjustment is carried out by using an inorganic or organic acid, an alkali solution, urea, calcium carbonate, ammonium or the like. Further, if necessary during culturing, an antibiotic such as Ampicillin or tetracycline may be added to the culture medium.

As the culture medium for culturing the transformant obtained by using the animal cell as the host cell, there is used RPM11640 medium which is commonly used (The Journal of the American Medical Association, 199, 519 (1967), Eagle's MEM medium (Science, 122, 501 (1952)), DMEM medium (Virology, 8, 396 (1959)), 199 medium (Proceeding of the Society for the Biological Medicine, 73, 1 (1950)), or the medium prepared by adding bovine fetus serum to any one of these media. Culturing is normally conducted under the condition of pH ranging from 6 to 8, a temperature ranging from 30 to 40° C., 5% $CO_2$ for 1 to 7 days. Moreover, if necessary during culture, an antibiotic such as kanamycin or Penicillin may de added to the culture medium.

As the culture medium for transformant obtained by using the plant cell as the host cell, there is used any medium such as MS medium, R2P medium and others, which are commonly used in accordance with plant species. Culturing is carried out for 1 to 21 days under the condition of pH 6 to 8 and 15 to 35° C. If necessary during culture, an antibiotic such as kanamycin or hygromycin may be added to the culture medium.

In order to isolate and purify the protein of the present invention which is involved in restoration of cytoplasmic male sterile individual to fertility from a cultured product of the transformant, ordinary isolation and purification methods may be used.

For example, when the protein of the present invention is expressed intracellularly in a dissolving state, after completion of culturing, the cells are collected by centrifugation and suspended in an aqueous buffer solution and then, the cells are broken by using an ultrasonic breaking machine, a French press, Manton Gaulin homogenizer, Dynomill to obtain a cell free extract solution. From a supernatant obtained by centrifugation of the cell free extract solution, a purified sample product can be obtained by using an ordinary protein isolation and purification method, such as solvent extraction method, salting-out method using ammonium sulfate and the like, desalination method, precipitation method using an organic solvent, anion exchange chromatography method using such resin as diethylaminoethyl (DEAE) Sepharose or DIAION HPA-75 (Mitsubishi Chemical Corp), cation exchange chromatography method using S-Sepharose FF (Pharmacia), hydrophobic chromatography method using such resin as butyl Sepharose or phenyl Sepharose, gel filtration method using a molecular sieve, affinity chromatography method, chromatofocusing method, and electrophoretic method such as isoelectric focusing, independently or in combination.

In the case where the protein is intracellularly expressed with forming an insoluble matter, the protein is collected from a fraction of precipitation which is obtained by collecting, destroyiong and centrifuging cells similarly, by an ordinary method. Then, the insoluble matter of the protein is solubilized by a protein-denaturing agent. A solution of the solubilized protein is diluted or dialyzed by a solution which lacks the protein-denaturing agent or contains the protein-denaturing agent at such a low concentration that the protein denaturation does not occur, so as to construct a normal stereoscopic structure of the protein. Then, a purified sample product can be obtained by the same isolation and purification method as those described above.

In the case where the protein of the present invention or its derivative such as sugar-modified molecule is extracellularly secreted, the protein or derivative such as the sugar chain-added molecule can be collected in the supernatant of the culture. The solubilized fraction is obtained by treating the culture product by techniques such as centrifugation as described above, and the purified sample product can be obtained from the solubilized fraction by using the isolation and purification method as described above.

The protein of the present invention can also be produced by such chemical synthesis method as Fmoc (fluorenyl methyl oxycarbonyl) method or tBoc (t-butyl oxycarbonyl) method. Further, synthesis can be performed by using a peptide synthesizer commercially available from Souwa Boueki (Advanced Chem tech, USA), Perkin Elmer Japan (Perkin Elmer, USA), Amerciam Pharmacia Biotech (Amerciam Pharmacia Biotech), Aroca (Protein. Technology Instrument, USA), Kurabou (Synthecell-Vega, USA), Japan PerSeptive Ltd. (PerSeptive, USA), and Shimadzu Corporation.

(7) Transformant of the Plant Having DNA of the Present Invention

The nucleotide sequence of SEQ ID NO. 1 and SEQ ID NO. 15 are the nucleotide sequence in a form in which the nucleotide sequence of the original genome of the plant has been extracted. This nucleotide sequence contains a promoter and a terminator necessary for gene expression in an operable form. Concerning the vector to be introduced, cloning of the gene can be performed in an ordinary cloning vector such as cosmid pWE15 (STRATAGANE) in a direct introduction method. In case of using Agrobacterium, cloning can be performed in an ordinary plant transformation vector such as pB1121 (Clontech).

The DNA of the nucleotide sequence from which a part of introns have been extracted from this (genomic) sequence, DNA of the nucleotide sequence from which almost all introns have been extracted, DNA of SEQ ID NO. 2 or 238th to 2064th nucleotides thereof, DNA of SEQ ID NO. 16 or 238th to 2064th nucleotides thereof, DNA of SEQ ID NO. 18 or 244th to 2073th nucleotides thereof, or DNA encoding a protein of SEQ ID NO. 3 or a region of 80th to 687th residues thereof, SEQ ID NO. 17 or a region of 80th to 687th residues thereof, or SEQ ID NO. 19 or a region of 82th to 690th residues thereof, may be introduced to the plant cell.

DNA having a sequence from 3754th to 5091th nucleoties of the nucleotide sequence of SEQ ID NO. 1 or DNA having a sequence from 1st to 811th nucleotides of the nucleotide sequence of SEQ ID NO. 15 is the promoter having an ability of transcribing an mRNA in an anther, and is preferably used for restoration from male sterility.

In addition, the promoter and terminator regions may be replaced with a promoter and a terminator which work in a known plant cell. The known plant promoters include promoter TA29 derived from tobacco (Plant Cell, 2 (12):1201-1224, 1990), Osg6B derived from rice (Plant Cell Physiol. 36 (3): 487-494, 1995), and A9 promoter derived from *B. napus* and *Arabidopsis* (Plant Mol. Biol. 19 (4): 611-622, 1992), which is expressed specifically in a plant anther.

In the case where the above DNA of SEQ ID NO. 2 or 238th to 2064th nucleotides thereof, DNA of SEQ ID NO. 16 or 238th to 2064th nucleotides thereof, DNA of SEQ ID NO. 18 or 244th to 2073th nucleotides thereof, or DNA encoding a protein of SEQ ID NO. 3 or a region of 80th to 687th residues thereof, SEQ ID NO. 17 or a region of 80th to 687th residues thereof, or SEQ ID NO. 19 or a region of 82th to 690th residues thereof, is introduced into the plant cell, the promoter and the terminator are necessary in addition to this DNA. Commonly used ordinary expression vector is exemplified by pB1121 (Clonetech). In this vector, 35S promoter of cauliflower mosaic virus is used as the promoter, and the terminator of nopaline synthesis enzyme, which is present in Ti plasmid of *A. tumefacience*, is used as the terminator. As the promoter necessary for expression, not only the above described 35S promoter of cauliflower mosaic virus, but also rbcS promoter widely present in plants may be used. More preferably, a promoter which is expressed in a developing period of pollens, for example, generally known TA29, Osg6B and A9 promoters which are expressed specifically in a tapetal tissue of the anther, are used. Further preferably, authentic promoters located in the upstream of the genes, are used. As the terminator, not only the above described terminator of nopaline synthesis enzyme, but also 35S terminator of cauliflower mosaic virus can be used. More preferably, an authentic terminator located in the downstream of the gene is used.

In the case where the above DNA of SEQ ID NO. 2 or 238th to 2064th nucleotides thereof, DNA of SEQ ID NO. 16 or 238th to 2064th nucleotides thereof, DNA of SEQ ID NO. 18 or 244th to 2073th nucleotides thereof, or DNA encoding a protein of SEQ ID NO. 3 or a region of 80th to 687th residues thereof, SEQ ID NO. 17 or a region of 80th to 687th residues thereof, or SEQ ID NO. 19 or a region of 82th to 690th residues thereof is used for the purpose of restoration of cytoplasmic male sterile individual to fertility, a mitochondrial transit sequence is necessary in addition to these sequences.

As the mitochondrial transit sequence, there is used DNA of 1st to 237th nucleotides of SEQ ID NO. 2 or DNA encoding 1st to 79th amino acids sequence of SEQ ID NO. 3; DNA of 1st to 237th nucleotides of SEQ ID NO. 16 or DNA encoding 1st to 79th amino acids sequence of SEQ ID NO. 17; DNA of 1st to 243th nucleotides of SEQ ID NO. 18 or DNA encoding 1st to 81th amino acids sequence of SEQ ID NO. 19; or the other known transit sequence mentioned above.

In the following examples, the present inventors have prepared the vectors for plant transformation in order to introduce the DNA (SEQ ID NO. 1) of the Rf gene which contains introns contained in regions from the authentic promoter present in the genome to the terminator, to the plant in an authentic form. After cleavage of the nucleotide sequence of SEQ ID NO. 1 from the clone composing a part of the contig by a restriction enzyme, the sequence was subcloned into an appropriate cloning vector. Then, the subcloned fragment was introduced into the vector pKM424 and pBIGRZ2 for plant transformation to obtain the vector which can introduce the fragment into the plant. This vector was introduced into *Agrobacterium* for plant transformation. By infecting *Agrobacterium* holding this vector to the plant, the DNA fragment is integrated into a plant genome.

The plant to which the gene of the present invention can be applied is exemplified by oil crop such as rapeseed, sunflower, soybean and palm, cereals such as rice, maize and wheat, flowering plants such as tobacco and petunia, and various vegetables such as tomato, broccoli, cabbage, Chinese cabbage and carrot.

Among these, *Brassica* plants such as rapeseed, cabbage, Chinese cabbage and broccoli, and tomato are preferable. Rapeseed, cabbage, Chinese cabbage and broccoli are particularly preferable, and rapeseed is most preferable.

In the present specification, the plant source for transformation is exemplified by a seed, a hypocotyl, a shoot, a callus, a cultured cell, and a plant body. For example, the hypocotyl or a protoplast in case of rapeseed; the hypocotyl, the callus or the cultured cell in case of soybean; the hypocotyl in case of sunflower; the callus or the cultured cell in case of palm; the hypocotyl, the callus, the cultured cell or the protoplast in case of rice; the hypocotyl, the shoot, the callus, the cultured cell or the protoplast in case of maize; the hypocotyl, the callus or the cultured cell in case of wheat; the hypocotyl, the callus, the cultured cell or the protoplast in case of cabbage and broccoli; the hypocotyl, the callus, the cultured cell or the protoplast in case of carrot. Preferred portions are appropriately selected depending on the subject plant, as those skilled in the art ordinarily perform.

Transformation of plant can be conducted by ordinary ways. For example, there are the method in that the vector is introduced into the plant by infecting a plant cell with *Agrobacterium* after the vector is once introduced to an *Agrobacterium* cell, and the method in that the vector is directly introduced into the cell by using, for example, electroporation method, DEAE dextran method, calcium phosphate method, polyethylene glycol method, and particle gun method.

For example, the preferred method for introducing a gene in the case of rapeseed is exemplified by the method described below.

A hypocotyl of a form of rapeseed aseptically germinated in the MS medium containing a sugar such as sucrose as the carbon source is precultured on the MS medium containing 2,4-dichlorophenoxy acetic acid and sucrose. *Agrobacterium* grown on YEB medium is collected by centrifugation and is suspended again on the MS medium containing sucrose. The above described hypocotyl of rapeseed is added in this suspension followed by shaking. Then, the hypocotyl taken out is returned to the original preculture medium for co-culture for 3 days followed by transfer to a selection medium containing plant hormones such as Zeatin and benzylaminopurine, and carbenicillin and kanamycin for selection. A regenerated individual is obtained by culturing the obtained regenerated green buds in a growth culture medium optionally containing a plant hormone such as benzylaminopurine and then in a rooting culture medium optionally containing plant hormones such as naphthalene acetic acid and benzylaminopurine. By crossing this individual with the individual of the cms line, $F_1$ hybrid of which fertility has been restored can be obtained.

The introduction of DNA of the present invention into the plant can enable restoration of cytoplasmic male sterile individual to fertility.

The transformed plant into which the DNA of the invention was introduced is used as a parent line for commercial production of $F_1$ hybrid seed in an ordinary breeding technique. As breeding methods for a parent line, an ordinary breeding technique is employed. The ordinary breeding technique is, as described in Buzza, G. C. (Plant Breeding In: "*Brassica* Oilseeds Production and Utilization" Kimber, D. S. and D. I. McGregor (eds.) CAB International, Cambridge 153-175, 1995) comprises crossing excellent parents with each other and repeating selecton of excellent lines for various agricultural traits. Selection may be carried out using various parts of a plant such as flower, hypocotyl, leaf, stem or root.

The line having an agriculturally excellent trait and having the introduced Rf gene is used as the pollen parent line in commercial seed production of the $F_1$ cultivar by preparing a double haploid using pollens or selecting a line having homozygotes through repeating self pollination.

In addition, in the case where $F_1$ seed production and production is carried out by using this transformant, a cytoplasmic male sterile line can be used as a mother line. The cytoplasmic male sterile plant in this procedure is, more specifically, a cybrid which is prepared by using Ogura or Kosena radish and which has orf125 or orf 138 which is a cytoplasmic male sterile gene of these cultivars in a mitochondrion.

For the regenerated plant as described above, expression can be confirmed by crossing it with rapeseed of the cms line and examining fertility of offspring thereof. In the case where transformation is conducted using a rapeseed plant having the cms character as a material, pollen fertility can be examined by transferring the transformant (regenerated individual), which has produced a root by the way described above, to soil containing an ordinary fertilizer to flower. This procedure is preferable in view of temporal and operational convenience.

In the above transformant, in the case where transformation is conducted as described above using the cell or the tissue, preferably the hypocotyle, a cotyledon, a leaf, a pollen, the cultured cell, the callus, and the protoplast of rapeseed plant which has cms cytoplasm as the cell source, the plant of which pollen fertility has been restored can be obtained by transferring the plant (regenerated individual) which has produced by the above method to soil containing the ordinary fertilizer to flower.

The plant cell in which the DNA has been integrated in the nucleus can be obtained by introducing the DNA of the present invention into the cms cell by the gene introducing method as described above using the cms cell, selecting the cell in which the DNA is integrated in the nucleus using a selection marker of tolerance against an antibiotic such as kanamycin or tolerance to herbicide as an index, and then culturing the cell in the growth culture medium or the rooting culture medium as described above. In this plant, fertility is restored from the male sterile character.

In an agricultural crop into which only the DNA is incorporated as a foreign gene in such a way, the introduced gene is present in a more preferable form as compared with the line prepared by a conventional technique such as crossing between species/genera or cell fusion. For example, as mentioned in Disclosure of the Invention, it is known that the Rf gene of radish to which this gene belongs, has a tight linkage with the gene involving in glucosinolate synthesis of seeds and, as known from the description of Delourme et al. (1995), the breakage of this tight linkage was difficult in rapeseed Rf line which was prepared by intergeneric crossing (Delourme R., Eber F. and Renard M. In: Rapeseed today and tomorrow, 9th International Rapeseed Congress" Murphy, D. et al. (eds.) The Dorset Press, Dorchester Vol. 1:6-8). However, in the transformant plant prepared by using the DNA according to the invention, only the DNA region involving in fertility restoration is introduced and a trait which is not preferable for breeding can be excluded. More specifically, introduction of a fragment of the DNA of the invention into rapeseed (*B. napus, B. rapa* and *B. juncea*) allows preparation of the Rf line which satisfies the Canola standard. In addition, by using this Rf line as a pollen parent, $F_1$ cultivar which satisfies the Canola standard can be commercially produced.

For detecting the gene involved in restoration to fertility, the applicable method is that 15 to 50mer oligonucleotide primer freely designed from the DNA of any of claims 1 to 4 or probe of at least 15 mer consisting of all or a part of the DNA of any of claims 1 to 4 is used, and the quantity of the nucleotide sequence amplified by the primer or the quantity of the nucleotide sequence detected by the probe in an organism sample of interest is confirmed to be 1 gene or more in 1 genome.

Specific technique for confirmation is exemplified by PCR method and Southern hybridization method, and among them, PCR method is preferable. These techniques can be conducted according to the method described in Molecular Cloning: A Laboratory Manual, 2nd Ed., Cold Spring Harbor Laboratory, Cold Spring Harbor, N.Y. 1989 (hereafter abbreviated to Molecular Cloning 2nd Ed.)

For confirming that there is 1 gene or more in 1 genome, by applying PCR method, it is necessary that as a simplified technique, a same degree of amplification can be observed by using a same number of copy of the DNA as a template. More accurately, in the same biological sample of a same amount, the quantity of this amplified known gene is compared with the quantity of the nucleotide sequence amplified by using the primer by applying quantitative PCR method using an optional primer for amplifying a known gene as an internal standard in which 1 gene presents in 1 genome. By examining the difference in the amplified amount, the transgenic homozygote can be selected in an early stage of growing and the purity of the Rf gene of the parent line can be confirmed at commercial seed collection of the F1 cultivar. In Southern hybridization method, the DNA of the plant of the fertility-restorer line in which 1 gene present in 1 genome is compared with the DNA of the objective plant sample at an equal amount, and then it is tested that the quantities of the DNAs detected are same or larger.

The primer used in PCR method is exemplified by the 15 to 50mer oligonucleotide identical or having complementation to the DNA sequence of SEQ ID NO. 1 or SEQ ID NO. 2.

The probe used in Southern hybridization method is exemplified by a total region of a double strand DNA identical to the DNA sequence of SEQ ID NO. 1 or SEQ ID NO. 2, or a part of at least 15mer or more thereof, or the total region of a single strand DNA or a complementary strand thereof, or a part of at least 15mer or more thereof. Moreover, DNA having a certain or higher degree of homology to the nucleotide sequence of the DNA which is used as the probe as mentioned above may be used. The certain or higher degree of homology used hereby is, for example 70% or higher, preferably 80% or higher, more preferably 90% or higher, further preferably 93% or higher, particularly preferably 95% or higher, and most preferably 97% or higher. The DNA having the certain or higher degree of homology includes both of the polynucleotide having homology described above and the polynucleotide of the complementary strand thereof.

The method for detection of the gene as described above can be applied as means of not only confirmation of integration of the DNA into the transformant, but also confirmation of presence of the Rf gene in the individual to which introduction of the Rf gene is attempted by crossing. By using this method, the presence of the Rf gene can be confirmed before flowering, in the case where the Rf gene is introduced into the cytoplasmic male sterile individual. In the case where the Rf gene is introduced to the plant having an ordinary cytoplasm, fertility of the individual of the next generation obtained by crossing the pollen in a flowering stage with the cytoplasmic male sterile individual should be confirmed, but the presence of the Rf gene can be confirmed before this step by using the present method. Such method of use is generally called use of a marker DNA or marker DNA breeding. The Rf gene may be used as the marker DNA of the Rf gene (Rf marker). The Rf marker is, as described above, important for breeding a commercial plant variety by using a recombinant to which the DNA has been introduced, and a non-recombinant plant to which the Rf gene has been introduced by crossing, as a mother plant.

Whether or not the introduced DNA works as Rf gene can be confirmed by confirming restoration of fertility of the transformant as mentioned above, and also by the method presented below.

As described above, the Rf gene restores fertility of the plant body by reducing an amount of ORF 125 or ORF 138 protein being the cms-associated protein, which is accumulated in the mitochondria. Therefore, by confirming the reduction of the amount of ORF 125 or ORF 138 protein accumulated in the mitochondria of the transformant, it can be confirmed that the introduced gene is the Rf gene.

The method for confirming the reduction of the amount of ORF 125 or ORF 138 protein accumulated in the mitochondria is, for example, a method of confirming that the hybridizing signal amount of an antibody against the protein derived from a mitochondrial genome used as the internal standard, such as anti $F_1$-$F_0$ ATPase (hereafter abbreviated to ATPA) described in N. Koizuka et al. Theor Appl Genet, 100: 949-955, 2000, is equal between the cytoplasmic male sterile individual and the transformant in which the DNA has been introduced to the fertility-restored plant or the cytoplasmic male sterile individual, when ORF 125 or ORF 138 protein is detected by Western blotting method according to the condition described in the present specification, and that the amount accumulated in the transformant produced by introducing the DNA to the fertility-restored plant or the cytoplasmic male sterile individual has been reduced by more than 50%, preferably 60% or more, more preferably 80% or more as compared with the amount of ORF 125 or ORF 138 protein accumulated in the cytoplasmic male sterile individual.

Practically, in a flower bud of the cytoplasmic male sterile radish plant having ORF 125, when the fertility-restorer gene Rf is introduced, the amount of ORF 125 protein accumulated is reduced markedly resulting in almost no detection. In rapeseed, in a flower bud of the fertility-restored rapeseed plant in which the fertility-restorer gene has been introduced to the cytoplasmic male sterile rapeseed which has the ORF 125 by crossing, it has been observed that the amount of ORF 125 protein accumulated is reduced by 80% or more. In the example, in the flower bud of the transformant rapeseed in which the gene has been introduced to the cytoplasmic male sterile individual, it has been observed that the amount of ORF 125 protein accumulated is reduced by 80% or more.

The antibody against ORF 125 and ORF 138 protein in the method as described above can be obtained by the following common technique. These proteins are immunized to an animal as an antigen to obtain an antiserum, and immunogloburin G antibody can be purified by using protein A-bound affinity column. The antigen to be used can be obtained by purifying the protein from the cytoplasmic male sterile individual which expresses it and the cultured cell by an ordinary method. In addition, the antigen is also obtained by combining ORF 125 and ORF 138 genes to the expression vector to express it in *Escherichia coli* and yeast followed by purification in the similar way. Moreover, the peptide obtained by chemically synthesizing a full length or a part of ORF 125 and ORF 138 can be used as the antigen. The antibody against ATPA can also be obtained by the similar technique.

Further, by introducing a part or all of the gene of the present invention to the cell having a cms cytoplasm and/or the DNA of the present invention together with the induction promoter, the expression of cms can be regulated specifically and temporarily, and thus a new hybrid seed production system which need not a male sterility-maintaining line (maintainer) and/or restorer line (Rf line) necessary for hybrid seed production can be produced.

That is, rapeseed of the cms line is normally sterile and thus, propagation and maintenance of the cms line requires the maintainer in which cms and Rf are not involved. Therefore, so far, production of a hybrid seed required plants of 3 lines, namely, the Rf line, the cms line, and the maintainer. However, because Rf gene was isolated and identified by the present invention and hence, applying the method for conducting induction of the promoter by a chemical substance in hybrid production so as to regulate expression of the restorer gene allows construction of the cms line capable of propagation and maintenance even without the maintainer.

Specifically, a full length or a part of the gene of the present invention is integrated into a vector having the promoter induced from outside, for example, the drug sensitive promoter, in an antisense or a sense direction or is constructed vector to induce gene silencing with the inducible promoter. Then, the cell having the cms cytoplasm and DNA of the present invention or having the cms cytoplasm alone is transformed by using the vector.

The cell having the cms cytoplasm and/or DNA of the present invention may be not only the cell obtained by transforming a cell having the cms cytoplasm with DNA of the present invention by the method as described above, but also the cell obtained by crossing the cms line with the Rf line.

The inducible promoter described above is known, for example, from Japanese Patent Laid-open Publication No. 6-46697, and the method for preparation of the vector and transformation is exemplified by the techniques similar to those described above.

The promoter is not induced usually in the transformant, which is the cell obtained by the method as described above, has the cms cytoplasm, and has or has not DNA of the present invention, and to which a part or all of DNA of the present invention is integrated together with the induction promoter. Therefore, the plant which carry the vector designed for up-regulation above described gene shows fertility when the induction is applied or the plant which carry the vector designed for down-regulation of the gene shows fertility caused by the inhibition of the endogenous Rf gene expression, and maintenance of the line can be carried out by self pollination. In the production of the hybrid, the chemical substance having an ability of inducing the promoter is acted on the plant which carry a vector can downregulate the endogenous Rf gene and thus, expression of the Rf gene is inhibited. Thus, the plant becomes male sterile and hence, can be used as the cms line in the production of the hybrid seed. Futhermore, when the cms line having both the endogenous Rf gene and the downregulation construct, Rf line so far required for hybrid seed production is not needed. Therefore, every rapeseed cultivars or lines without Rf gene can be used as pollen donor (father). Thus in addition to the unnecessary of the maintainer, the Rf line becomes unnecessary and a production cost can be reduced considerably.

Applying these methods allow propagation and maintenance by self pollination even in the cms line. Consequently, though 3 lines are so far required for production of the hybrid seed, it becomes possible that the maintainer becomes unnecessary and a production cost can be reduced considerably.

The contents disclosed in each specification of Japanese Patent Application Nos. 2001-128008, 2001-202082 and 2002-20083, baaed on which the present application claims priorities, should be understood to be incorporated in the present specification by reference.

Examples of the present invention are given below in detail, but the following examples are in no way intended to limit the scope of the present invention.

EXAMPLES

Example 1

Isolation of DNA Marker which is Linked with the Cytoplasmic Male Fertility Restorer Gene, and Preparation of the Genome Map For isolation of the fertility restorer gene (Rf gene), it is first necessary to isolate the DNA marker located around the Rf gene and prepare the genome map showing a relationship between genetic distances of this DNA marker and Rf gene. As the starting point, positional cloning of an Rf region was carried out.

As the method for isolating the DNA marker, AFLP was carried out by using AFLP Analysis System I AFLP Starter Kit of GIBCO BRL for AFLP (Amplified fragment length polymorphism) method (Nucleic Acids Research, 1995, Vol. 23, NO. 21 4407-4414). As the material used for measuring the genetic distance from the marker, $F_2$ population of about 2100 individuals which were obtained by self pollination of eight individuals of radish $F_1$ generation produced by crossing one individual ((KC2/KA1)-1) of *Raphanus sativus* cv. Kosena of the cms line with one individual (Yuan10-3) of *Raphanus sativus* cv. Yuanhong according to the method described in N. Koizuka, et al., Theor Appl Genet, 100:949-955 2000, was used. As a result, in a form sandwiching the Rf gene, 5 markers linking in the position of the genetic distance of 0.2 to 0.3 cM from either side of the gene were isolated. FIG. 1 shows the genomic map showing the genetic distance of each DNA marker and the Rf gene.

Example 2

Preparing Contig and Analysis of the Rf Gene on the Basis on the Genomic Map

Subsequently to preparation of the genomic map, it is necessary that the genomic DNA corresponding to the position is cloned and the DNA markers sandwiching the Rf gene are linked. Since the DNA markers are distant from the Rf gene and thus, by combining a plurality of clones having the genome DNA fragment, the contig of the Rf gene region covering across DNA markers was prepared.

A group of clones having the genome DNA fragment is named a genomic library. We prepared two types of the library. As a DNA donor, the genomic DNA was prepared from Yuanhong radish which is same as the parent of the restorer line used for preparation of the $F_2$ population, by means of CTAB method (Murray, M. G. and Thompson, W. F. (1980) Nucleic Acids Res., 8, 4321) according to an ordinary technique. For the library, a lambda phage library of a 20 kb average length and $1.5 \times 10^5$ population number was prepared by using λ DASHII vector (STRATAGENE) as the lambda vector. As the cosmid vector, the cosmid library of a 40 kb average length and $5.5 \times 10^4$ population number was prepared by using pWEB::TNC vector (EPICENTRE TECHNOLOGIES).

In the contig preparation, a lambda clone was first isolated from the lambda phage library prepared in the above using the DNA marker located in both sides of the Rf gene as an index by plaque hybridization technique. A cosmid clone was isolated from the cosmid library by using colony hybridization technique to complete the contig covering across the DNA markers of both sides as shown in FIG. 1. For the cosmid clones, NIT7/2 and TO3-2, which compose a part of the contig, the nucleotide sequence was determined by an ordinary method.

Subsequently, the nucleotide sequence of the cosmid clones NIT7/2 and TO3-2 which compose a part of the contig above was analyzed by using "Genscan" (Mitsubishi Space Software) in consideration of a parameter for *Arabidopsis thaliana*, of which the genomic DNA sequence is similar to that of radish and the total genome sequence was determined recently. As the result, the promoter region which is seemed to express the Rf gene, the structural gene region containing the intron, and the terminator region were discovered. In addition, the gene having a form to be translated to the protein which introns have been removed from and the amino acid sequence thereof were obtained.

Example 3

Subcloning of the Genomic DNA Region

HpaI-SwaI fragment (8546 bp) of the DNA of the nucleotide sequence from 1st to 8553th of SEQ ID NO. 1, which contains enough regions from the promoter to the terminator which were presumed by "Genscan", was separated from the vector by gel electrophoresis using agarose (FMC) for fragment collection. A gel containing the DNA fragment was digested by a GELase (Epicentre Technologies) to collect the DNA. Then, cloned fragments were obtained by cleavage of the obtained fragment using a restriction enzyme, BamHI. These DNA fragments were subcloned to pGEM-T easy vector (Promega) to obtain cds6BT/pGEM-T easy. Details will be described below.

1 µg of NIT7/2 cosmid DNA and 10 unit of restriction enzyme HpaI (Takara) were added to 100 µl of 1×K restriction enzyme buffer solution (20 mM Tris-HCl (pH8.5), 10 mM $MgCl_2$, 1 mM Dithiothreitol, 100 mM KCl), and incubated at 37° C. for 1 hour.

After incubation, 10 µl of 3M sodium acetate (pH5.6) and 250 µl of ethanol were added and stirred, followed by cooling at −80° C. for 5 minutes, and then the mixture was centrifuged at 15000 rpm and 4° C. for 15 minutes. Supernatant was removed and 1 ml of 70% ethanol was gently added thereto, and the mixture was centrifuged at 15000 rpm and 4° C. for 5 minutes. Supernatant was removed and precipitant was dried using a centrifugal vacuum dryer for 5 minutes. 89 µl of sterilized water was added to the collected DNA precipitant to dissolve DNA.

To the dissolved DNA solution were added 10 µl of 10×H restriction enzyme buffer solution (500 mM Tris-HCl (pH7.5), 100 mM $MgCl_2$, 10 mM Dithiothreitol, 1000 mM NaCl), 1 µl of 10 unit/µl restriction enzyme SwaI (Takara), and the mixture was incubated at 25° C. for 1 hour. 11 µl of 10× loading buffer solution (1% SDS, 50% Glycetrol, 0.05% Bromophenol Blue) were added.

1.2 g of low melting point agarose, SeaPlaque GTG agarose (FMC) and 150 ml of 1×TAE (40 mM Tris-acetate, 1 mM EDTA) buffer solution were mixed, and the mixture was heated at 100° C. to melt agarose, and cooled down to 45° C. while stirring. A comb of 30 mm width×1 mm thickness was set on a 14×15 cm gel tray, and the cooled gel was poured for coagulation. The DNA to which a loading Dye had been added was poured into the gel comb and subjected to electrophoresis in 1×TAE at 30V/30 cm voltage for 18 hours.

The gel electrophoresed gel was transferred to 0.5 µg/ml of ethidium bromide/1×TAE solution for staining for 30 minutes. The gel was put on a transilluminator on which 365 nm long wave ultraviolet rays were irradiated, and a fragment of interest of 8546 bp was cut out using a sterilized knife. Subsequently, the gel was chopped to make about 1 mm square fragment and transferred to 2 ml microtube previously weighed, and the weight of the gel was measured.

1 µl of 50×GELase Buffer (2M Bis-Tris (pH6.0), 2M NaCl) per 50 mg weight of the gel, was added. The tube containing the gel was put in a dry heat block incubated at 68° C., the solution was stirred sometimes turning over and incubated for 10 minutes to melt the gel completely. This tube was transferred to the dry heat block incubated to 45° C. and the solution was stirred sometimes turning over and incubated for 5 minutes. 1 unit of GELase (Epicentre Technologies) per 200 mg weight of the gel was added to this tube, and the solution was stirred sometimes turning over and incubated for 30 minutes in the dry heat block incubated to 45° C.

⅓ volume of 10 M ammonium acetate (pH 7.0) per 1 volume of the gel was added, and the solution was stirred and centrifuged at 15000 rpm for 5 minutes. The supernatant was transferred to a fresh 2 ml microtube, and 2 volumes of ethanol were added thereto. The tube was stirred and centrifuged at 15000 rpm and 4° C. for 20 minutes. The supernatant was removed and 1 ml of 70% ethanol was gently added, and the solution was centrifuged at 15000 rpm and 4° C. for 5 minutes. The supernatant was removed and the precipitation was dried by the centrifugal vacuum dryer for 5 minutes. 20 µl of TE buffer (10 mM Tris-HCl (pH8.0), 1 mM EDTA) was added to the precipitation and the solution was completely dissolved to collect DNA.

To 20 µl of the collected DNA solution were added 10 µl of 10×K restriction enzyme buffer solution (200 mM Tris-HCl (pH8.5), 100 mM $MgCl_2$, 10 mM Dithiothreitol, 1000 mM KCl), 68 µl of $dH_2O$, 2 µl of 10 unit/µl of restriction enzyme BamHI (Takara), and the mixture was incubated at 30° C. for 1 hour. After incubation, 10 µl of 3M sodium acetate (pH5.6) and 250 µl of ethanol were added, and the mixture was stirred and cooled at −80° C. for 5 minutes, and centrifuged at 15000 rpm and 4° C. for 15 minutes. The supernatant was removed and 1 ml of 70% ethanol was gently added again, and the mixture was centrifuged at 15000 rpm at 4° C. for 5 minutes. The supernatant was removed and the precipitation was dried for 5 minutes using the centrifugal vacuum dryer. 20 µl of sterilized water was added to the collected DNA precipitation to dissolve it. 55 µl of sterilized water, 10 µl of 10×PCR buffer solution (100 mM Tris-HCl (pH8.3), 500 mM KCl), 6 µl of 25 mM MgCl$_2$, 8 µl of 2.5 mM dNTP mix, 1 µl of 5 unit/µl rTaq DNA polymerase (Takara) were added and mixred, and then the mixture was incubated at 72° C. for 30 minutes to add dATP to 3' terminal.

The above reaction solution was transferred to an ultrafiltration filter unit, Microcon-50 (Millipore), and centrifuged at 5000 rpm and 4° C. for 20 minutes. Water on a trap was discarded, 100 µl of sterilized water was again added, and the mixture was centrifuged at 5000 rpm and 4° C. for 20 minutes. 20 µl of the TE buffer solution (10 mM Tris-HCl (pH8.0), 1 mM EDTA) was added, the filter unit was removed, and the direction was reversed to attach to the new microtube. The solution was centrifuged at 3000 rpm and 4° C. for 5 minutes to collect the DNA on the filter unit.

1 µl of 50 ng/µl pGEM-T easy vector (Promega) and 6 µl of Solution I of DNA Ligation Kit Ver.2 (Takara) were mixed to 5 µl of the purified DNA obtained by the above method, and then the mixture was incubated at 16° C. for 30 minutes.

The above reaction solution was transferred to the ultrafiltration filter unit, Microcon-50 (Millipore) together with 100 µl of sterilized water, and then the solution was centrifuged at 5000 rpm and 4° C. for 20 minutes. Water on the trap was discarded, 100 µl of sterilized water was again added, and the mixture was centrifuged at 5000 rpm and 4° C. for 20 minutes. The filter unit was removed and the direction was reversed to attach to the new microtube.

DNA on the filter unit was collected by centrifugation at 3000 rpm and 4° C. for 5 minutes.

DNA collected in the tube was cooled by standing on ice. 30 µl of *Escherichia coli* DH10B (Gibco BRL) for electroporation was put in the tube and mixed gently. *Escherichia coli* cells mixed with DNA were transferred to a cuvette (USA Scientific Plastics) previously cooled on ice for electroporation (distance between electrodes was 1 mm). Using Electro Cell Manipulator 600 (BTX), electroporation was conducted under conditions of 1.25 kv, 129Ω, and 50 µF, and then 500 µl of SOC culture medium (Gibco BRL) warmed at 37° C. was added to the cuvette immediately. The *Escherichia coli* was transferred to a 10 ml culture tube and subjected to shake culturing at 37° C. for 1 hour. The cultured *Escherichia coli* was spread on LB agar medium (1% Bacto-Tryptone, 0.5% Bacto-Yeast Extract, 1% NaCl, 1.5% Bacto-Agar) to which 100 µg/ml of Ampiciline (Wako Pure Chemicals Ltd.), 20 µg/ml of X-Gal (Takara) and 1 mM of IPTG (Takara) were added, and cultured for 18 hours or longer at 37° C.

A white colony appeared on an agar culture medium was cultured at 37° C. for 18 h or longer on 2 ml of LB medium to which 100 µg/ml of Ampicillin was added. The plasmid DNA was extracted from cultured *Escherichia coli* cells by the ordinary method. It was confirmed that a fragment of interest was cloned in the plasmid DNA by cleavage with restriction enzyme EcoRI (Takara), and thus cds6BT/pGEM-T easy was obtained.

Individual *Escherichia coli* DH10B carrying cds6BT/pGEM-T easy which was obtained by the above method, was cultured at 37° C. for 18 hours on 100 ml of LB culture medium to which 100 g/ml of Ampicillin was added. Purification was carried out by alkali SDS method using Qiagen Midi Kit (QIAGEN).

Example 4-1

Preparation of the Vector for Plant Transformation
(1)

cds6BT/pGEM-Teasy was cleaved with restriction enzyme EcoRI and then separated from the vector by gel electrophoresis using agarose for fragment collection. The collected DNA fragment was cloned in EcoRI site of the vector for plant transformation pKM424 (a vector in which a fragment of CaMV35S promoter: GUS gene: NOS terminator were added to pKM424, is pLAN421 (Plant Cell Reports 10 (1991) 286-290) vector) to prepare the vector for plant transformation cds6BT/pKM424. A detail will be presented below.

To 100 µl of 1×H restriction enzyme buffer solution (50 mM Tris-HCl (pH 7.5), 10 mM MgCl$_2$, 1 mM Dithiothreitol, 100 mM NaCl) were added 1 µg of cds6BT/pGEM-T easy DNA and 10 units of restriction enzyme EcoRI (Takara), and the mixture was incubated at 37° C. for 1 hour.

Subsequently, EcoRI fragment containing cds6BT was separated and collected from cds6BT/pGEM-T easy by the same method as that for collecting the above HpaI-SwaI fragment.

To 100 µl of 1×H restriction enzyme buffer solution (50 mM Tris-HCl (pH 7.5), 10 mM MgCl$_2$, 1 mM Dithiothreitol, 100 mM NaCl) were added 1 µg of the vector for plant transformation pKM424 and 10 units of restriction enzyme EcoRI (Takara), and the mixture was incubated at 37° C. for 1 hour. After incubation, 100 µl of 1M Tris-HCl (pH8.0) and 1 unit of Bacterial Alkaline Phosphatase (Takara) were added and mixed. Then, dephosphorylation was carried out by incubating at 50° C. for 1 hour.

200 µl of phenol-chloroform saturated by TE buffer solution (10 mM Tris-HCl (pH8.0) and 1 mM EDTA) was added and the mixture was vigorously stirred. Centrifugation was performed at 15000 rpm for 5 minutes and then, the supernatant was transferred to a fresh tube. The same operation was repeated again to remove the protein. 20 µl of 3M sodium acetate (pH5.6) and 500 µl of ethanol were added, and the mixture was stirred and cooled at −80° C. for 5 minutes, followed by centrifugation at 15000 rpm and 4° C. for 15 minutes. The supernatant was removed and 1 ml of 70% ethanol was gently added and centrifuged at 15000 rpm and 4° C. for 5 minutes. The supernatant was removed and the precipitation was dried for 5 minutes using the centrifugal vacuum dryer. 100 µl of TE buffer solution (10 mM Tris-HCl (pH8.0), 1 mM EDTA) was added to the precipitation to dissolve it completely to make a 10 ng/µl concentration.

10 µl of purified EcoRI fragment, 1 µl of dephosphorylated pKM424vector, and 11 µl of Solution I of DNA Ligation Kit Ver. 2 (Takara) were mixed, and then the mixture was incubated at 16° C. for 30 minutes.

The above reaction solution was transferred to the ultrafiltration filter unit: Microcon-50 (Millipore) together with 100 µl of sterilized water and centrifuged at 5000 rpm and 4° C. for 20 minutes. Water on the trap was discarded, 100 µl of sterilized water was again added, and the solution was centrifuged at 5000 rpm and 4° C. for 20 minutes. The filter unit was removed and attached to a fresh microtube in a reverse direction.

Centrifugation was carried out at 3000 rpm and 4° C. for 5 minutes to collect the DNA on the filter unit.

The collected DNA contained in the tube was stood on ice to be cooled. 30 µl of *Escherichia coli* DH10B (Gibco BRL) for electroporation was put in the tube and mixed gently. The *Escherichia coli* mixed with DNA was transferred to a cuvette for electroporation (USA Scientific Plastics) previously cooled on ice (distance between electrodes was 1 mm). By using Electro Cell Manipulator 600 (BTX), electroporation was conducted under conditions of 1.25 kv, 129Ω and 50 µF, and then 500 µl of SOC culture medium (Gibco BRL) warmed at 37° C. was added to the cuvette immediately. The *Escherichia coli* was transferred to a 10 ml culture tube and subjected to shake culturing at 37° C. for 1 hour. The cultured *Escherichia coli* was spread on LB agar medium (1% Bacto-Tryptone, 0.5% Bacto-Yeast Extract, 1% NaCl, 1.5% Bacto-Agar) to which 50 μg/ml of Spectinomycin (Sigma) was added, and cultured for 18 hours or longer at 37° C.

The colony appeared on the agar medium was cultured in 2 ml of LB medium to which 50 μg/ml of Spectinomycin was added, at 37° C. for 18 hours or longer. The plasmid DNA was extracted from the cultured *Escherichia coli* by an ordinary method. It was confirmed that the region from BamHI site to HpaI site was cloned in the plasmid DNA by cleavage with restriction enzyme HindIII (Takara). The plasmid was named cds6BT/pKM424.

*Escherichia coli* DH10B carrying cds6BT/pKM424 was cultured in 250 ml of LB medium to which 50 μg/ml of Spectinomycin was added, at 37° C. for 18 hours. Purification was conducted by alkali SDS method using Qiagen Midi Kit (Qiagen Corp).

Example 4-2

Preparation of the Vector for Plant Transformation (2)

Figure 2:
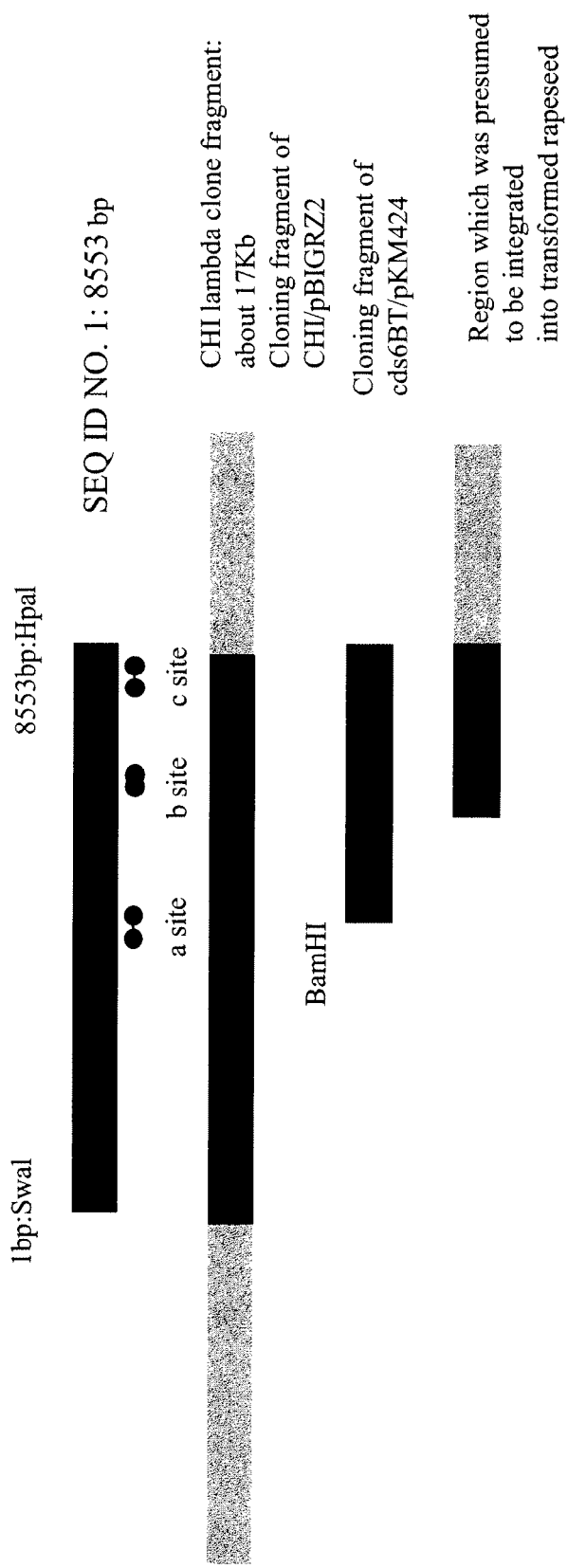
FIG. 2 shows diagrammatic view of a structure of a lambda clone CHI carrying the nucleotide sequence of SEQ ID NO. 1.

Lambda clone CHI (see FIG. 2, Cloned fragment of length of about 17 kb) carrying enough the nucleotide sequence of SEQ ID NO. 1 was cleaved with a restriction enzyme NotI (Takara) which is located in the multiple cloning site, and then separated from the vector by gel electrophoresis using agarose for collecting the fragment, and the collected fragment was cloned in the NotI site of the vector pBIGRZ2 (Bioscience and Industry 55 (1997) 37-39) for plant transformation to prepare the vector CHI/pBIGRZ2 for plant transformation. The detail will be presented below.

To 100 μl of 1×H restriction enzyme buffer solution (50 mM Tris-HCl (pH7.5), 10 mM MgCl$_2$, 1 mM Dithiothreitol, 100 mM NaCl, 0.01% BSA, and 0.01% TritonX-100) were added 1 μg of lambda clone CHI DNA and 10 units of restriction enzyme NotI (Takara), and the mixture was incubated at 37° C. for 1 hour. The NotI fragment of the lambda clone CHI was separated and collected by the same method as that applied for collecting HpaI-SwaI fragment as described above.

To 100 μl of 1×H restriction enzyme buffer solution (50 mM Tris-HCl (pH7.5), 10 mM MgCl$_2$, 1 mM Dithiothreitol, 100 mM NaCl, 0.01% BSA, and 0.01% TritonX-100) were added 1 μg of the vector pBIGRZ2 for plant transformation and 10 units of restriction enzyme NotI (Takara), and the mixture was incubated at 37° C. for 1 hour. After incubation, 100 μl of 1M Tris-HCl (pH8.0) and 1 unit of Bacterial Alkaline Phosphatase (Takara) were added and mixed, and then the mixture was incubated at 50° C. for 1 hour for dephosphorylation.

200 μl of phenol/chloroform saturated with TE buffer solution (10 mM Tris-HCl (pH8.0), 1 mM EDTA) was added, and then the mixture was stirred vigorously. After centrifugation at 15000 rpm for 5 minutes, the supernatant was transferred to a fresh tube. The same operation was repeated again to remove the protein. 20 μl of 3M sodium acetate (pH5.6) and 500 μl of ethanol was added and stirred, and then cooled at −80° C. for 5 minutes, followed by centrifugation at 15000 rpm at 4° C. for 15 minutes. The supernatant was removed and 1 ml of 70% ethanol was gently added, and the solution was centrifuged at 15000 rpm and 4° C. for 5 minutes. The supernatant was removed and the precipitation was dried for 5 minutes by using the centrifugal vacuum dryer. 100 μl of TE buffer solution (10 mM Tris-HCl (pH8.0), 1 mM EDTA) was added to the precipitation to dissolve it completely to make 10 ng/μl concentration.

10 μl of purified NotI fragment, 1 μl of dephosphorylated pBIGRZ2 vector, and 11 μl of solution I of DNA Ligation Kit Ver. 2 (Takara) was mixed, and the mixture was incubated at 16° C. for 30 minutes.

The above reaction solution was transferred to the ultrafiltration filter unit Microcon-50 (Millipore) together with 100 μl of sterilized water, and centrifuged at 5000 rpm and 4° C. for 20 minutes. Water on the trap was discarded, 100 μl of sterilized water was again added, and the mixture was centrifuged at 5000 rpm and 4° C. for 20 minutes. The filter unit was removed, and direction was reversed to attach to a fresh microtube. The solution was centrifuged at 3000 rpm at 4° C. for 5 minutes to collect the DNA on the filter unit.

The collected DNA contained in the tube was stood was on ice to be cooled. 30 μl of *Escherichia coli* DH10B (Gibco BRL) for electroporation was put in the tube and mixed gently. The *Escherichia coli* mixed with the DNA was transferred to the cuvette (USA Scientific Plastics) for electroporation which was previously cooled on ice (distance between electrodes was 1 mm). By using Electro Cell Manipulator 600 (BTX), electroporation was conducted under conditions of 1.25 kv, 129Ω and 50 μF, and then 500 μl of SOC culture medium (Gibco BRL) warmed at 37° C. was added to the cuvette immediately. The *Escherichia coli* was transferred to 10 ml culture tube and subjected to shake culturing at 37° C. for 1 hour. The cultured *Escherichia coli* was spread on LB agar medium (1% Bacto-Tryptone, 0.5% Bacto-Yeast Extract, 1% NaCl, 1.5% Bacto-Agar) to which 25 μg/ml of kanamycin (Wako Pure Chemicals) was added, and cultured at 37° C. for 18 hours or longer.

The colony appeared on the agar medium was cultured in 2 ml of LB medium to which 25 μg/ml of Kanamycin was added, at 37° C. for 18 hours or longer. The plasmid DNA was extracted from the cultured *Escherichia coli* by an ordinary technique. It was confirmed by cleavage with restriction enzyme HindIII (Takara) that a fragment of interest was cloned in the plasmid DNA. The plasmid was named CHI/pBIGRZ2.

*Escherichia coli* DH10B carring CHI/pBIGRZ2 was cultured in 250 ml of LB medium to which 25 μg/ml of Kanamycin was added, at 37° C. for 18 hours. Purification was carried out by alkali SDS method using Qiagen Midi Kit (Qiagen).

Example 5

Transfer of the Vector for Plant Transformation to *Agrobacterium*

A competent cell of *Agrobacterium* was prepared, and each of cds6BT/pKM424 vector and CHI/pBIGRZ2 vector obtained in Examples 4-1 and 4-2 was transferred to the prepared *Agrobacterium* EHA101 for plant transformation. Details will be given below.

The competent cell for electroporation of *Agrobacterium* EHA101 was prepared by the following method. The *Agrobacterium* EHA101 was streaked on LB agar medium to which 50 μg/ml of Kanamycin (Wako Pure Chemicals) and 25 μg/ml of Chloramphenicol (Wako Pure Chemicals) were added, and cultured at 28° C. for 24 hours or longer to obtain a single colony. 20 ml of the LB medium to which 50 μg/ml Kanamycin and 25 μg/ml Chloramphenicol were added, was put into a 50 ml centrifugal tube, the colony of about 1 mm diameter was inoculated and subjected to shake culturing at 28° C. for 40 hours. After 40 hours, a lid of the centrifugal tube was once opened followed by closing, and further culturing was conducted for 4 hours in the same way. The culture solution was centrifuged at 1500×g and 4° C. to collect the cells. In the tube from which the supernatant was discarded was added 40 ml of ice-cooled and sterilized 10% glycerol, followed by resuspension of the cells and centrifugation at 1500×g at 4° C. for collection of the cells. This operation was repeated twice. 500 μl of 10% sterilized ice-cooled glycerol was added to the obtained cells for resuspension. 100 μl of the cells were dispensed to each of sterilized microtubes and frozen with liquid nitrogen, and then stored at −80° C. in a freezer.

Competent cells of *Agrobacterium* EHA101 for electroporation were dissolved on ice. 40 μl of electrocompetent cells was put in previously cooled 1.5 ml tubes, and 100 ng of the plasmid DNA of either cds6BT/pKM424 or CHI/pBIGRZ2 was added and gently mixed.

*Agrobacterium* mixed with the DNA was transferred to the cuvette for electroporation (USA Scientific Plastics) which was precooled on ice (distance between electrodes was 1 mm). By using Electro Cell Manipulator 600 (BTX), electroporation was conducted under conditions of 1.44 kv, 129Ω and 50 μF, and then 500 μl of SOC culture medium (Gibco BRL) warmed at 30° C. was added to the cuvette immediately. The *Agrobacterium* was transferred to 10 ml culture tube and subjected to shake culturing at 30° C. for 1 hour.

As to *Agrobacterium* to which cds6BT/pKM424 vector was transferred, the cultured Agrobacterium was spread on the LB agar medium (1% Bacto-Tryptone, 0.5% Bacto-Yeast Extract, 1% NaCl, 1.5% Bacto-Agar) to which 50 μg/ml Kanamycin (Wako Pure Chemicals), 25 μg/ml Chloramphenicol (Wako Pure Chemicals), 50 μg/ml of Spectinomycin (Sigma) and 2.5 μg/ml of Tetracycline (Sigma) were added, and was cultured at 28° C. for 24 hours or longer.

As to *Agrobacterium* to which CHI/pBIGRZ2 vector was transferred, the cultured *Agrobacterium* was spread on the LB agar medium to which 50 μg/ml Kanamycin (Wako Pure Chemicals), 25 μg/ml Chloramphenicol (Wako Pure Chemicals) and 30 mg/ml of Hygromycin (Sigma) were added, and was cultured at 28° C. for 24 hours or longer.

The colony appeared on agar medium was cultured in 2 ml of LB medium to which the above antibiotics corresponding to each vector was added, at 30° C. for 24 hours or longer. The plasmid DNA was extracted from the cultured Agrobacterium by an ordinary method. It was confirmed by cleavage with restriction enzyme HindIII (Takara) that cds6BT/pKM424 vector or CHI/pBIGRZ2 vector was transferred to the *Agrobacterium*. The culture solution of 24 hour culturing which contains the confirmed clone was mixed with an equal amount of sterilized 80% glycerol, and was stored at −80° C. This clone was used for transformation of rapeseed plant.

Example 6

Preparation of Rapeseed Transformant

Transformation of rapeseed was conducted as follows. Seeds of CMS rapeseed (SW18) having the cms associated gene orf125 derived from radish was subjected to sterilizing treatment with a 10% hypochloride solution to be germinated on MS medium (T. Murashige and F. Skoog, Physiol. Plant. 15: 485, 1962) containing no hormone. Only a hypocotyl was dissected from a seedling plant 7 to 14 days after germination, cut and divided into a 3 to 5 mm length, and precultured on the MS medium (Sigma; M5519) containing sucrose (3%) and 2,4-D (1 mg/L) and agarose (0.4%) (Sigma; Type I) at 23° C. for 12 to 16 hours. In this time, co-culturing was carried out together with a cell line BY-2 derived from tobacco for nurse culture.

The *Agrobacterium* containing CHI/pBIGRZ2 was cultured at 28° C. for 8 to 48 hours to be grown to about $OD_{600}$=1.0. The cells of the *Agrobacterium* were suspended in a liquid MS hormone-free medium. The cut hypocotyl was mixed with this *Agrobacterium* solution, and subjected to co-culturing for about 20 minutes. After co-culturing, the hypocotyl from which *Agrobacterium* was removed by a filter paper, was cultured on, for example, the MS basic medium containing vitamin B5 (Sigma; M0404), sucrose (3%) and 2,4-D (1 mg/L), for 2 days for infection. After infection, the cotyledon was transferred to the bacteria removed medium obtained by adding an antibiotic Carbenicillin (Pfeizer: zeopen or GIBCO-BRL: Carbenicillin disodium salts) at a concentration of 500 mg/L to the MS basic medium containing vitamin B5, sucrose (3%) and 2,4-D (1 mg/L), so as to remove *Agrobacterium*.

After passed through 5 days to 1 week on the bacteria removed medium, the hypocotyl was cultured on the MS basic medium containing vitamin B5, sucrose (1%), benzylaminopurine (3 mg/L), Carbenicillin (500 mg/L) as well as silver nitrate (5 mg/L) and Kanamycin for selection (5 to 30 mg/L) (Nakalai Tesque; sulfate of Kanamycin) for 14 days to 21 days. In this time, there may appear a green callus, which should be immediately transferred by inoculating to the medium of the next step.

The medium of the next step is exemplified by the selection medium of, for example, the MS basic medium (Sigma; M5519), sucrose (1%), benzylaminopurine (3 mg/L), zeatin (1 mg/L), Carbenicillin (500 mg/L) and Kanamycin (5 to 30 mg/L). The hypocotyl forming the callus from a cut point was transferred to this culture medium, and was cultured at 23° C. for 3 weeks. Then, such transfer was repeated 3 to 5 times for every 3 weeks up to occurrence of the green callus.

The green callus was, at any time when it found, cut from the hypocotyl, and was transferred to the medium having the same composition. Thereafter, when only the green portion was cut and subcultured, an adventitious bud was formed with a probability of 1 to 30%. Subsequently, the adventitious bud was transferred to the B5 basic medium (Sigma; G5893) to which sucrose (3%) and benzylaminopurine (1 mg/L) were added, and grown followed by rooting on the MS medium (Sigma; M5519) containing sucrose (3%), naphthalene acid (0.1 mg/L) and benzylaminopurine (0.01 mg/L).

Example 7

Analysis of the Transformant (Detection of the DNA Transferred)

A leaf was taken from one individual of the transformant, which was obtained in the Example 6 and formed a bud, and the DNA was isolated using DNA isolation kit of Qiagen (DNAeasy Plant Mini).

Figure 3:
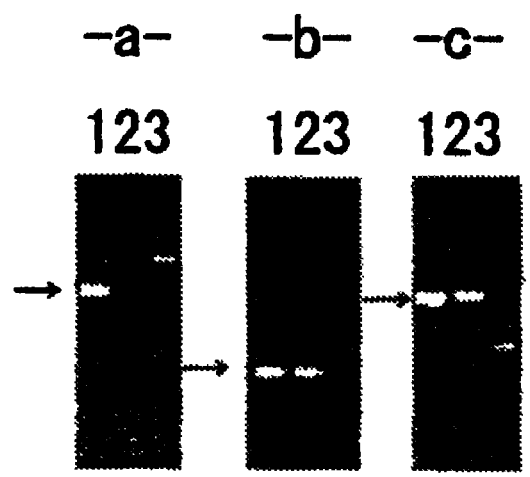
FIG. 3 shows a result of detection of a DNA introduced into transformant by using PCR method.

For 3 sites (sites a, b and c) of the DNA fragment transferred was detected by PCR method (the result is shown in FIG. 3). The site a is 568 bp from 3186 bp to 3753 bp nucleotide sequence of SEQ ID NO. 1, and as a forward primer "5'-GAAGCAAAAAAGAAAACGAGCAGAG-3'" (SEQ ID NO. 4) and as a reverse primer "5'-CCAAAAATC-CGAAATCCGAATAGAC-3'" (SEQ ID NO. 5) were used. The site b is 244 bp from 4869 bp to 5112 bp nucleotide sequence of SEQ ID NO. 1, and as a forward primer "5'-CTCGGCTCTGGGTTTAGTGA-3'" (SEQ ID NO. 6) and as a reverse primer "5'-TCCACAAACCCTAGCCAACA-3'"

(SEQ ID NO. 7) were used. The site c is 485 bp from 7766 bp to 8250 bp nucleotide sequence of SEQ ID NO. 1, and as a forward primer "5'-GCTTATGCTTCTCTGGTTCGCCTC-3'" (SEQ ID NO. 8) and as a reverse primer "5'-CTCAGTTTTCGTCACCTTACACAATGC-3'" (SEQ ID NO. 9) were used.

To 1 µl of the transformant DNA solution (50 ng/µl) were added 12.1 µl of sterilized water, 2 µl of 10×PCR buffer solution (100 mM Tris-HCl (pH8.3), 500 mM KCl), 1.2 µl of 25 mM MgCl$_2$, 1.6 µl of 2.5 mM dNTP mix, 1 µl of 10 µM forward primer solution for each site, 1 µl of 10 µM reverse primer solution for each site, 0.1 µl of 5 unit/µl of rTaq DNA polymerase (Takara), followed by mixing. Then, the DNA was amplified by repeating 35 times a cycle of 94° C. for 40 seconds, 55° C. for 30 seconds and 72° C. for 1 minute. UNOII (Biometra) was used as a thermal cycler. After completion of the reaction, the amplified product was detected by gel electrophoresis under the condition of 4% Nusive3:1 Agarose (FMC)/1×TBE (89 mM Tris-borate, 89 mM boric acid, 2 mM EDTA) buffer solution (see FIG. 3)

As the result, it was found that the site a was not transferred to this transformed rapeseed. It was found that in the remaining two sites (sites b and c), the amplification product having the same size to that of a positive control was obyielded and therefore, the DNA was integrated into the transformed rapeseed.

Example 8

Analysis of the Transformant (Detection of Reduced Accumulation of the cms Associated Protein ORF125)

A flower bud of the same plant as that of the Example 7 was taken, and the reduced accumulation of the cms associated protein ORF 125 was analyzed by Western blotting. The result is shown in FIG. 4.

(1) Extraction of the Protein from the Transformed Plant

Protein extraction and Western blotting were carried out according to the method of N. Koizuka et al (Theor Appl Genet (2000) 100: 949-955).

Specifically, 1 flower bud (1 mm in length) of the obtained transformed rapeseed and 100 µl of the ice-cooled buffer solution (50 mM Tris-HCl (pH7.5), 2% (W/V) SDS) for protein extraction were put in an ice-cooled mortar and were ground with a pestle. This solution was transferred to a centrifugal microtube and centrifuged at 15000 rpm for 15 minutes at 4° C. After centrifugation, the supernatant was transferred to a fresh centrifugal microtube and heated at 100° C.; for 5 minutes. Centrifugation was carried out again at 15000 rpm and 4° C. for 15 minutes, and the supernatant was transferred to a fresh centrifugal microtube to prepare SDS-solubilized protein solution. The concentration of the SDS-solubilized protein solution was measured by Bradford method using a protein quantification kit (Bio-rad). Simultaneously with this operation, the SDS-solubilized protein solution was similarly extracted from flower buds of rapeseed of the cytoplasmic male sterile line and rapeseed of the sterility restorer line, and the concentrations were measured.

(2) Separation of the Protein by SDS-PAGE and Transfer to a PVDF Membrane: Western Blotting Using 10% SDS polyacrylamide gel of 7×10 cm square, 15 µg of the SDS-solubilized protein was put on 1 lane for separation by electrophoresis. In addition, for comparison of accumulations of ORF125 protein, diluted series of rapeseed of the cytoplasmic male sterile line were put on the gel and separated. Electrophoresis was conducted under the condition of 10 mA for 1 hour and 15 mA for 1 hour. After electrophoresis, the protein contained in the polyacrylamide gel was transferred to the PVDF membrane (Millipore) using semi-dry blotting apparatus (Nipppon Electrophoresis) under the condition of 100 mA for an hour.

(3) Detection of the Protein Using an Antibody: Western Blotting

The PVDF membranes to which the protein was transferred were cut into halves and transferred to 10 ml of a blocking solution (20 mM Tris-HCl (pH 7.5), 500 mM NaCl, 0.05% Tween20, 5% skim milk), and were blocked by shaking for an hour. ATPA was detected on the top PVDF membrane as the control of a mitochondrial protein, and ORF125 which is the protein involved in the cytoplasmic male sterility was detected on the bottom PVDF membrane. The PVDF membrane was transferred to 10 ml of a primary antibody reaction solution (100 µl of an ATPA monoclonal antibody for detection of ATPA was added to 10 ml of the blocking solution, and 2 µl of rabbit antiserum against ORF125 for detection of ORF125 was added (M. Iwabuchi et al., Plant Molecular Biology (1999) 39: 183-188)), and shaken for 18 hours. The PVDF membrane was transferred to 100 ml of TTBS (20 mM Tris-HCl (pH7.5), 500 mM NaCl, 0.05% Tween20) and shaken for 10 minutes. This operation was repeated 3 times to wash out an excessive primary antibody solution. The PVDF membrane was transferred to 10 ml of a secondary antibody reaction solution (to 10 ml of the blocking solution were added 10 µl of peroxidase labeled goat anti-mouse IgG (Amersham) for detection of ATPA and 10 µl of alkali phosphatase labeled goat anti-rabbit IgG (Bio-rad) for detection of ORF125 respctively (M. Iwabuchi et al. Plant Molecular Biology (1999) 39: 183-188)), and both solutions were shaken for an hour. The PVDF membrane was transferred to 100 ml of TTBS (20 mM Tris-HCl (pH7.5), 500 mM NaCl, 0.05% Tween20), and was shaken for 10 minutes. This operation was repeated three times to wash out an excessive secondary antibody solution. A chemiluminescence system "ECL+" (Amersham) for peroxidase was used for detection of ATPA and exposure was carried out for 5 seconds for detection. For detection of ORF125, BCIP/NBT (MOSS Inc.) which is a coloring substrate for alkali phosphatase was used, and coloration and detection was carried out for 5 minutes.

As the result, it was shown that the accumulations of ATPA which is the control are almost unchanged in the flower bud of the cytoplasmic male sterile rapeseed of 2 lines, fertility-restored raperapeseed, and the flower bud of the transformant rapeseed obtained by introducing DNA in the cytoplasmic male sterile line, but the accumulation of ORF125 protein was reduced significantly in the transformant rapeseed. A degree of this reduction is equal to that of the fertility-restored line obtained by transferring a fertility restorer gene to the cytoplasmic male sterile line by crossing (FIG. 4, and M. Iwabuchi et al., Plant Molecular Biology (1999) 39: 183-188). It was showed that the degree of reduction of ORF125 protein accumulation was ⅛ to 1/16 in fertility-restored raperapeseed and about ⅛ in the transformant rapeseed by comparison with the diluted series. As described above, the restoration of fertility in rapeseed strongly relates with the reduction of accumulation of ORF125 protein, and both means an identical sense. Therefore, it was demonstrated that the DNA sequence has a function of reducing the accumulation of ORF125 protein in the mitochondria and is a genome DNA sequence carrying the fertility restorer gene.

In addition, the pollen grains were taken out from the flowering plant and microscopically observed. As the result, it was confirmed that normal pollens were produced (FIG. 5.)

Example 9

Isolation of cDNA

Isolation of cDNA was carried out by selecting the $F_2$ plant which has homozygous Rf1 genes and shows pollen fertility, as an RNA donor from the $F_2$ population used for preparation of the gene map, purifying mRNA from the flower bud, and then using 5'-RACE or 3'-RACE method after synthesis of the cDNA.

(Purification of mRNA)

Total RNA was extracted from the flower bud of the $F_2$ plant which has homozygous Rf1 genes and shows pollen fertility, by applying guanidium thiocyanate method as an ordinary method by using RNeasy kit (Qiagen). PolyA$^+$RNA was purified from the total RNA using "mRNA Purification kit" (Amersham Pharmacia) using Origo (dT) cellulose column, and was used as mRNA. (Isolation of cDNA by 5'-RACE and 3'-RACE)

cDNA was isolated using 1 μg of purified mRNA using "Marathon RACE system 5'RACE 3'RACE" kit based on 5'-RACE and 3'-RACE methods. As gene specific primers, 5'-GATTCCTTTCTCTTGCATTTCAG-3' (SEQ ID NO. 10) was used for the 5'-RACE, and 5'-ATCTCGTCCTTTACCT-TCTGTGG-3' (SEQ ID NO. 11) was used for the 3'-RACE. After the nucleotide sequence of the obtained clone was determined, the sequence of the cDNA was obtained (SEQ ID NO. 2).

Example 10

Conversion of cDNA to Amino Acid Sequence, and Analysis Thereof (1) Conversion of cDNA to the amino acid sequence was carried out using an ordinary genetic code and a gene analysis software "Genetyx-SV" (Software Development K.K.), resulting in obtaining the amino acid sequence of SEQ ID NO. 3. The PPR motif was analyzed by employing a program registered in Protein Families Database of Alignments and HMNs (hereafter abbreviated to Pfam; http://www.sanger.ac.uk/Software/Pfam/search.shtml).

As the result of the analysis, it was found that the translated product of the fertility restorer gene of SEQ ID NO. 1 was the protein having 16 PPR motifs. The PPR motif has 3 PPR clusters. The 3 clusters were:
(1) PPR cluster #1: the PPR cluster composed of consecutive 175 residues of the first to fifth PPR motifs from the N terminal;
(2) PPR cluster #2: the PPR cluster composed of consecutive 245 residues of the sixth to 12th PPR motifs from the N terminal; and
(3) PPR cluster #3: the PPR cluster composed of consecutive 140 residues of the 13th to 16th PPR motifs from the N terminal.

Example 11

Analysis of the Protein of the Present Invention

It was experimented whether or not translation is inhibited in *Escherichia coli* by binding to the transcription product (mRNA) of the gene of the protein ORF 125 causing Kosena cytoplasm male sterility.

The fertility restorer gene of SEQ ID NO. 2 was introduced into BamHI-SphI site of the expression vector pQE-80L (Qiagen) of *Escherichia coli* to construct the expression vector which adds six histidine residues (6× His) to the N terminal (pQEB1/cds6). DNA was amplified by using the primer: CGGGATCCGCTCACAATT (SEQ ID NO. 12) for introducing BamHI site and M13 primer RV (Takara) and using pSTV29 (Takara) vector as a template. For DNA amplification, Takara LA PCR Kit (Takara) was used. The amplified DNA was cleaved by restriction enzymes BamHI and EcoRI (Takara), and then was purified by using Suprec-02 (Takara). In order to synthesize a DNA fragment having BamHI and EcoRI sites in both ends of 5'-UTR site of orf125 gene and 25 amino acids of orf125, PCR was carried out according to Fujimoto' method (Plant PCR Experiment Protocol: Practice of DNA synthesis. PP 84-87 (Syuuzyunsya)) using 2 primers. The 2 primers used were:

```
125-5'BamHI:
                                    (SEQ ID NO. 13)
GCGGATCCCAATTTCATTCTGCATCACTCTCCCTGTCGTTATCGACCTC
GCAAGGTTTTTGAAACGGCCGAAACGGGAAGTGACAATACCGCTTTTCT
TC;
and 125-5'EcoRI:
                                    (SEQ ID NO. 14)
GGAATTCACTAACTTTACATTCAGTAGGAGTGAGATTATGACAAAAAGT
GGACAATTTTTCGAAAAAGGTAATCATGCATTTATATGCTGAAGAAAAG
CG.
```

The amplified DNA was cleaved with restriction enzymes BamHI and EcoRI (Takara) and purified by using Suprec-02 (Takara). The purified DNA was ligated using TaKaRa Ligation kit (Takara). *Escherichia coli* DH10B (Gibco BRL) was transformed therewith and was cultured at 37° C. for 18 hours or longer on LB agar medium (1% Bacto-Tryptone, 0.5% Bacto-Yeast Extract, 1% NaCl, 1.5% Bacto-Agar, 0.1 mM IPTG, 20 μg/ml X-Gal) to which 50 μg/ml of chloramphenicol (Sigma) was added. A plasmid was extracted from a pale blue colony by an ordinary method, and the nucleotide sequence was determined. Thus, a vector (pSTV125-5' #LA6) was constructed where 174 bp (7th to 180th nucleotides of the nucleotide sequence of FIG. 6) containing 5'-UTR region of orf125 gene and 25 amino acids of orf125 was introduced between EcoRI site and a transcription-starting point of lacZ gene. Further simultaneously, the vector having the fragment (7th to 193th nucleotide of the nucleotide sequence of FIG. 6) in which several mutations occur in the portion corresponding to the 174 bp, was obtained (pSTV125-5' #LA12).

The vectors pSTV125-5' #LA6 and #LA12 were each transferred to *Escherichia coli* DH10B (Gibco BRL), and the cells were standing-cultured on the agar medium obtained by adding 50 μg/ml of chloramphenicol (Wako Pure Chemicals), 200 μM of IPTG (Wako Pure Chemicals) and 40 μg/ml of X-Gal (Takara) to LB medium, at 37° C. overnight to grow the colony, resulting in pale blue colony. Thus, it was confirmed that that the transferred LacZ gene was expressed in *Escherichia coli* to which either vector was transferred.

In addition, in order to transfer the above pSTV125-5' vector and pQEB1/cds6 vector to the *Escherichia coli* which is same as that described above, when the cells were cultured using the medium to which 50 μg/ml of Ampicillin was added, in the case of co-cultureing with pSTV125-5' #LA6, the colony became white. However, in case of co-culturing with pSTV125-5' #LA12 having a mutation in a transfer fragment site, the colony became pale blue, and the degree of bluing was same as that of the case of #LA12 alone. Whether *Escherichia coli* lack any one of these transferred vectors was examined by extracting the vectors by an ordinary method after culturing of each colony.

From the above results, it is understood that the protein expressed in *Escherichia coli* by pQEB1/cds6 vector became the white colony through suppression of expression of LacZ gene as the result of binding with mRNA of pSTV125-5' #LA6. In case of co-culturing with pSTV125-5' #LA12, it is understood that mutation occurs in the transfer fragment site and thus, the protein derived from pQEB1/cds6 can not be bound to mRNA and as the result, LacZ gene is expressed to make blue.

Consequently, it is supposed that the protein having the amino acid sequence of SEQ ID NO. 3 influences mRNA of orf125, more specifically the transcription product of a code region of at least orf125-5'UTR region and 25 amino acid residues of ORF125 so as to suppress expression of the ORF125 protein.

It is presumed that the translation product of the gene of the present invention is, after translocated to the mitochondria, binds to the male sterile gene in the mitochondria to inhibit translation, resulting in reduction of the accumulation of the causal protein of cytoplasmic male sterility and thereby cytoplasmic male sterility is restored to fertility.

Example 12

Isolation of the Fertility Restorer Gene of Kosena Rapeseed

The genome sequence of the fertility restorer gene was obtained from the line of rapeseed (hereafter Kosena rapeseed) which was obtained by transferring the fertility restorer gene of Kosena radish by cell fusion, by applying PCR method. The DNA was extracted from 0.1 g of a leaf of Kosena rapeseed using DNA Isolation Kit (DNeasy plant mini) of Qiagen. In order to amplify the DNA, 5'-ACAT-AAAAATCACTAGATACTTGACATGGAGGC-3' (SEQ ID NO. 30) which is the sequence of 1027 bp to 1059 bp nucleotide of SEQ ID NO. 1, was designed as the forward primer and 5'-AAGAGGAGGAAGATGGCATCACAGC-3' (SEQ ID NO. 31) which is the sequence of 7675 bp to 7651 bp nucleotide of SEQ ID NO. 1, was designed as the reverse primer.

To 10 µl of Kosena rapeseed DNA solution (50 ng/µl) were added 49 µl of sterilized water, 10 µl of 10× LA PCR buffer solution (Takara), 10 µl of 25 mM MgCl₂, 16 µl of 2.5 mM dNTP mix, 2 µl of 10 µM forward primer solution, 2 µl of 10 µM reverse primer solution, and 1 µl of 5 unit/1 µl of TaKaRa LA Taq (Takara), followed by mixing. DNA was amplified by repeating 30 times a cycle of 98° C. for 20 seconds and 68° C. for 15 minutes. The thermal cycler used was UNOII (Biometra). After completion of the reaction, about 6 kb of the amplified product was purified using the ultrafiltration filter unit Microcon-PCR (Millipore). The nucleotide sequence of 3306 bp of 4280th to 7585th nucleotide of SEQ ID NO. 1 was determined by an ordinary method using the purified product as the template (SEQ ID NO. 15). By comparison of the genome nucleotide sequence obtained from Kosena rapeseed with the sequence obtained from Yuanhong radish, DNA nucleotide substitutions were found in 7 bp among 3306 bp, and it was revealed that they have a high homology.

Further, cDNA sequence of the fertility restorer gene of Kosena rapeseed at 3' part was obtained by RT-PCR, and it was confirmed that introns were spliced in the same manner as in Yuanhong radish. From the bud of Kosena rapeseed, the total RNA was extracted by AGPC (Acid Guanidium-Phenol-Chloroform) method (Syuuzyunsya. Cell Engineering Separate volume: Biotechnology Experiment Illustrated, (2) Fundamentals of gene analysis: 161 to 166) which is an ordinary method. From 1 µg of total RNA, cDNA was synthesized using SUPERSCRIPT II RNaseH-Reverse Transcriptase (Invitrogen). 5'-TGGAGTAAAGAGGAACTAAAAAGGGC-3' (SEQ ID NO. 32) was used as the fertility restorer gene 3' part specific forward primer and 5'-CAGACAATAGACG-CATAAAAGGC-3' (SEQ ID NO. 33) was used as the fertility restorer gene 3' part specific reverse primer. The DNA was amplified by adding and mixing 14.9 µl of sterilized water, 2.5 µl of 10×PCR buffer solution (Takara), 1.5 µl of 25 mM MgCl₂, 2 µl of 2.5 mM dNTP mix, 1.5 µl of 10 µM forward primer solution, 1.5 µl of 10 µM reverse primer solution and 0.1 µl of 5 unit/µl TaKaRa Taq (Takara) to 1 µl of Kosena rapeseed cDNA solution and repeating 35 times a cycle of 94° C. for 40 seconds, 60° C. for 30 seconds and 72° C. for 2 minutes. The thermal cycler used was UNOII (Biometra). To 3 µl of the amplified product were added 1 µl of pGEM-Teasy vector (Promega), 5 µl of 2× ligation buffer solution (Promega) and 1 µl of T4 DNA ligase (Promega), and the mixture was left standing at room temperature for 1 hour to ligate to the vector. *Escherichia coli* DH5α (Gibco BRL) was transformed with this vector to obtion a clone. The nucleotide sequence of the obtained clone was determined by an ordinary method, and it was confirmed that introns of the cDNA of Kosena rapeseed was spliced in the similar way as in Yuanhong radish. Thus, it was found that 7 bp base substitutions found by the genome sequence comparison were present in 5444 bp to 5814 bp of SEQ ID NO. 1 and did not influence the splicing.

From the above results, it was found that the fertility restorer gene of Kosena rapeseed was expressed in the similar way as in Yuanhong radish. The sequence of cDNA which encodes only the translation region is shown in SEQ ID NO. 16. The amino acid sequence (SEQ ID NO. 17) was obtained from this cDNA sequence.

Example 13

Isolation of Partial Sequence of the Fertility Restorer Gene of a Wild Radish, *Raphanus raphanistrum* (Hereafter *R. raphanistrum*)

A partial sequence of the fertility restorer gene of *R. raphanistrum* was isolated from a cDNA.
(Purification of mRNA)
Total RNA was extracted from the bud of *R. raphanistrum* by AGPC (Acid Guanidium-Phenol-Chloroform) method (Syuuzyunsya. Cell Engineering Separate volume: Biotechnology Experiment Illustrated, (2) Fundamentals of gene analysis: 161 to 166) which is an ordinary method. PolyA⁺ RNA was purified from total RNA using "mRNA Purification kit" (Amersham Pharmacia) using Oligo (dT) cellulose column, and was used as mRNA.
(Isolation of the Partial Sequence of cDNA)
cDNA was synthesized from 1 µg of purified mRNA using "Marathon RACE system 5'RACE 3'RACE" kit (Clontech).
5'-GATTCCTTTCTCTTGCATTTCAG-3' (SEQ ID NO. 34) was used as the fertility restorer gene specific forward primer and 5'-ATCTCGTCCTTTACCTTCTGTGG-3' (SEQ ID NO. 35) was used as the fertility restorer gene specific reverse primer.

To 1 µl of *R. raphanistrum* cDNA solution were added 14.4 µl of sterilized water, 2.5 µl of 10× Pyrobest PCR buffer solution (Takara), 2 µl of 2.5 mM dNTP mix, 2.5 µl of 10 µM forward primer solution, 2.5 µl of 10 µM reverse primer solution, and 0.1 µl of 5 unit/2 µl of Pyrobest DNA polymerase (Takara), followed by mixing. DNA was amplified by repeating 30 times a cycle of 98° C. for 5 seconds, 55° C. for 30 seconds, and 72° C. for 1 minute and 30 seconds. The thermal cycler used was UNOII (Biometra). 0.1 µl of 5 unit/µl TaKaRa Taq (Takara) was added and mixed to the amplified DNA solution. Then, adenine nucleotide was added to 3' terminal of DNA by treatment of incubation at 72° C. for 10 minutes. To 3 µl of the amplified product were added 1 µl of pGEM-Teasy vector (Promega), 5 µl of 2× ligation buffer solution (Promega) and 1 µl of T4 DNA ligase (Promega), and the mixture was left standing at room temperature for an hour for ligation with the vector. *Escherichia coli* DH5α (Gibco BRL) was transformed with this vector to obtain a clone. The nucleotide sequence of the obtained clone was determined by an ordinary method, and cDNA partial sequence was obtained (SEQ ID NO. 20). Moreover, the amino acid sequence (SEQ ID NO. 21) was obtained from the cDNA sequence.

Example 14

Isolation of the Fertility Restorer Gene of Ogura Rapeseed

The cDNA sequence of the fertility restorer gene was isolated from the line of rapeseed which was obtained by transferring the fertility restorer gene of Ogura radish by crossing (hereafter Ogura rapeseed), by applying 5'RACE method and 3'RACE method.
(Purification of mRNA)

Total RNA was extracted from the flower buds of Ogura rapeseed by AGPC (Acid Guanidium-Phenol-Chloroform) method (Syuuzyunsya. Cell Engineering Separate volume: Biotechnology Experiment Illustrated, (2) Fundamentals of gene analysis: 161 to 166) which is an ordinary method. PolyA⁺RNA was purified using "mRNA Purification kit" (Amersham Pharmacia Corp.) using Origo (dT) cellulose column, and was used as mRNA.
(Isolation of the Partial Sequence of cDNA)

cDNA was synthesized from 1 µg of purified mRNA using "Marathon RACE system 5'RACE 3'RACE" kit (Clontech). 5'-GATCCATGCATTTGTCAAGG-3' (SEQ ID NO. 36) was used as the fertility restorer gene specific forward primer and CATTTGTGTAGCCTCATCTAGG-3' (SEQ ID NO. 37) was used as the fertility restorer gene specific reverse primer.

To 1 µl of Ogura rapeseed cDNA solution were added 14.4 µl of sterilized water, 2.5 µl of 10× Pyrobest PCR buffer solution (Takara), 2 µl of 2.5 mM dNTP mix, 2.5 µl of 10 µM forward primer solution, 2.5 g, 1 of 10 µM reverse primer solution, and 0.1 µl of 5 unitig 1 of Pyrobest DNA polymerase (Takara), followed by mixing. DNA was amplified by repeating 30 times a cycle of 98° C. for 5 seconds, 55° C. for 30 seconds and 72° C. for 1 minute and 30 seconds. The thermal cycler used was UNOII (Biometra). 0.1 µl of 5 unit/µl TaKaRa Taq was added and mixed to the amplified DNA solution, then, adenine nucleotide was added to 3' terminal of the DNA by treatment of incubation at 72° C. for 10 minutes. To 3 µl of the amplified product were added 1 µl of pGEM-Teasy vector (Promega), 5 µl of 2× ligation buffer solution (Promega) and 1 µl of T4 DNA ligase (Promega), and the mixture was left standing at room temperature for 1 hour to ligate with the vector. *Escherichia coli* DH5α (Gibco BRL) was transformed with this vector to obtain a clone. The nucleotide sequence of the obtained clone was determined by an ordinary method, and four partial sequences of cDNA were obtained. On the basis of information of the obtained four partial sequences, primers were designed at four common parts for 5'RACE and 3'RACE, and each cDNA was isolated.
(Isolation of cDNA by 5'RACE and 3'RACE)

cDNA was isolated in the same way as described above and performing 5'RACE and 3'RACE using "Marathon RACE system 5'RACE 3'RACE" kit (Clontech). As the gene specific primer, 5'-CATTTGTGTAGCCTCATCTAGG-3' (SEQ ID NO. 37) and 5'-GTCCGGAGAGCAGCCCTTGGTAG-3' (SEQ ID NO. 38) were used for 5'RACE, and 5'-TCATCG-TATAATTCTTCAGCCTC-3' (SEQ ID NO. 39) was used for 3'-RACE.

In 5'RACE, PCR was performed twice to obtain DNA. To 2 µl of an Ogura rapeseed cDNA solution which was diluted 250 times were added 8.6 µl of sterilized water, 2 µl of 10×LA PCR buffer solution (Takara), 2 µl of 25 mM MgCl₂, 3.2 µl of 2.5 mM dNTP mix, 1 µl of 10 µM primer solution of SEQ ID NO. 9907F, 1 µl of 10 µM adapter primer solution (Marathon RACE system 5'RACE 3'RACE kit, Clontech) and 0.2 µl of 5 unit/µl TaKaRa LA Taq (Takara), followed by mixing. DNA was amplified by repeating 5 times a cycle of 98° C. for 5 seconds and 72° C. for 3 minutes, 5 times a cycle at 98° C. for 5 seconds and 70° C. for 3 minutes, and 25 times a cycle of 98° C. for 5 seconds and 68° C. for 3 minutes. The obtained DNA solution was diluted 100 times, and to 2 µl thereof were added 8.6 µl of sterilized water, 2 µl of 10× LA PCR buffer solution (Takara), 2 µl of 25 mM MgCl₂, 3.2 µl of 2.5 mM dNTP mix, 1 µl of 10 µM primer solution of SEQ ID NO. 5' ogu-1, 1 µl of 10 µM adapter primer solution (Marathon RACE system 5'RACE 3'RACE kit, Clontech) and 0.2 µl of 5 unit/µl TaKaRa LA Taq (Takara), followed by mixing. DNA was amplified by repeating 5 times a cycle of 98° C. for 5 seconds and 72° C. for 3 minutes, 5 times a cycle of 98° C. for 5 seconds and 70° C. for 3 minutes, and 25 times a cycle of 98° C. for 5 seconds and 68° C. for 3 minutes. The thermal cycler used was UNOII (Biometra).

In 3' RACE, to 2 µl of an Ogura rapeseed cDNA solution which was diluted 50 times were added 8.6 µl of sterilized water, 2 µl of 10× LA PCR buffer solution (Takara), 2 µl of 25 mM MgCl₂, 3.2 µl of 2.5 mM dNTP mix, 1 µl of 10 µM primer solution of SEQ ID NO. 3' ogu-1, 1 µl of 10 µM adapter primer solution (Marathon RACE system 5'RACE 3'RACE kit, Clontech) and 0.2 µl of 5 unit/µl TaKaRa LA Taq (Takara), followed by mixing. DNA was amplified by repeating 35 times a cycle of 98° C. for 5 seconds, 63° C. for 30 seconds and 72° C. for 2 minutes.

To 3 µl of the amplified product were added 1 µl of pGEM-Teasy vector (Promega), 5 µl of 2× ligation buffer solution (Promega), and 1 µl of T4 DNA ligase (Promega), and the mixture was left standing at room temperature for 1 hour to ligate with the vector. *Escherichia coli* DH5α (Gibco BRL) was transformed with this vector to obtain a clone. The nucleotide sequence of the obtained clone was determined, and then, 5'RACE sequence and 3'RACE sequence corresponding to the above 4 partial sequences of cDNA were obtained. The full length cDNA sequence was obtained by combinating each sequence. Among these, the sequence having the highest homology with cDNA sequence of Yuanhong radish was identified as the fertility restorer gene of Kosena rapeseed (SEQ ID NO. 18). Further, the amino acid sequence (SEQ ID NO. 19) was obtained from the cDNA.

Example 15

Analysis of the Fertility Restorer Gene

For individual fertility restorer genes obtained by the above method, analyses were conducted by using an gene analysis software "Mac Vector 6.5" (Oxford Molecular Ltd.) for homology of the cDNA sequence and the amino acid sequence and by using Protein families database of alignments and HMNs usable in Sanger Institute, U. K. for motif analysis.

All of the Rf genes derived from Yuanhong radish, Kosena rapeseed and Ogura rapeseed according to the present invention have 16 PPR motifs, and these PPR motif groups are divided into 3 blocks of 5, 7, and 4 motifs from the amino terminal, and the fourth amino acid located in the second PPR motif from the amino terminal was asparagine. The partial fragment derived from *Raphanus raphanistrum* was also analyzed by applying it to the corresponding part (94th to 264th of the SEQ ID NO. 26) of the above sequence, and as the result, it was found that it had a part corresponding to the first to sixth PPR motifs from the amino terminal, and the PPR motif groups and the fourth amino acid located in the second PPR motif from the amino terminal also showed the characteristics as described above.

Moreover, among 3 fertility restorer genes obtained from Yuanhong radish, Kosena rapeseed and Ogura rapeseed, and the protein (SEQ ID NO. 26) and the gene encoding it (SEQ ID NO. 27) of the present invention which were obtained by the result of the analysis of the partial sequence of the fertility restorer gene of *R. raphanistrum*, Yuanhong radish shows very high homology with Kosena rapeseed. That is, the amino acid sequences show high homology value of 99.6% (only 3 amino acids are different) and the nucleotide sequences show high homology value of 99.7%. Therefore, the protein having an amino acid sequence of SEQ ID NO. 29 and the gene (SEQ ID NO. 25) encoding it are particularly preferred.

On the other hand, comparison of Ogura rapeseed with Yuanhong radish and Ogura rapeseed with Kosena rapeseed showed a high homology. Each homology in the amino acid sequence showed 92.0% in comparison of Ogura rapeseed with Yuanhong radish and 91.6% in comparison of Ogura rapeseed with Kosena rapeseed. The comparison in the nucleotide sequence showed about 95% in both cases. These values are lower than those between Yuanhong radish and Kosena rapeseed.

Example 16

Preparation and Analysis of Transformant Rapeseed to Which cds6BT/pKM424 was Introduced Using the method described in Examples 5 and 6, *Agrobacterium* EHA101 line to which cds6BT/pKM424 was introduced, was infected to the hypocotyl of rapeseed to obtain a transgenic plant.

The transformant rapeseed to which cds6BT/pKM424 was introduced was analyzed as follows.

(1) Detection of the Introduced Gene

The plant transforming vector, cds6BT/pKM424, was infected to the male sterile line SW18 to introduce the gene therein, and Southern hybridization was conducted to identify an introduced site in 3 plants of which pollen fertility has been restored. Total DNAs isolated from the transgenic plant by CTAB method were digested with a restriction enzyme BamHI, and the obtained DNA fragment was separated by 0.7% agarose gel and was fixed on a nylon membrane. To this nylon membrane was hybridized $^{32}$P labeled DNA probe (site specific) to detect a signal. Upon introducing cds6BT fragment to pKM424, BamHI and HpaI sites in the introducing fragment side disappear and, hence, BamHI site is present in 1 site on the vector. The Southern hybridization pattern is shown in FIG. 7. In FIG. 7, BamHI digested of total DNA (2.5 µg radish or 5 µg *Brassica napus*) was hybridized with TOT7 probe. Rf Radish: fertility-restored radish plant which is homozygous for restorer of fertility locus; SW18: *B. napus* CMS line; Westar: *Brassica* napus cv Westar. #33, #32 and #34: transgenic line with 4.7-kbp BamHI/Hpa I fragment. TOT7 fragment was amplified by PCR from CHI DNA with primers 5'-AAAGACGGACGTCATACCGATG-3' (SEQ ID NO. 40) and 5'-GACATGTAGGCCCAATGTCGT-3' (SEQ ID NO. 41).

From the Southern hybridization pattern, it was found that the transgenic plant contained the complete BamHI-HpaI fragment containing cds6 gene. Plant #32 containing 1 copy of the introduced gene was selected from the 3 plants, and was used for the following experiments.

(2) Expression Analysis of cds6 in the Transgenic Plant

Gene expression of cds6 site in the transgenic plant #32 was analyzed. Total RNAs were isolated from a bud of the transgenic plant by using RNeasy kit (Qiagen). Using these total RNAs as a substrate, cDNA was prepared by using an oligo-dT primer and Superscript II reverse transcriptase kit (Invitrogen). Using the cDNA as a template, RT-PCR was conducted. As the primers, DNAs of SEQ ID NO. 10 and SEQ ID NO. 33 were used. The result of RT-PCR analysis was shown in FIG. 8. In FIG. 8, Rf Radish: fertility-restored radish plant which is homozygous for restorer of fertility locus; SW18: *B. napus* CMS line; Westar: *Brassica napus* cv Westar; and #32: transgenic line with 4.7-kbp BamHI/Hpa I fragment. From an inflorescence of the transgenic plant, a PCR fragment having a length same to that of radish fertile plant having the Rf gene could be detected. Therefore, it has been found that the transgenic plant containing 3811st to 5091st sequence in the DNA sequences of SEQ ID NO. 1 which is present in the sequence of the introduced radish gene contains the promoter region capable of expressing the fertility restoration gene in the anther of the plant.

Moreover, by using the procedure described in Example 8, reduction of ORF125 mitochondrial protein which is a product of CMS causal gene was studied with respect to the bud of the transgenic plant #32. The result of Western blotting of ORF125 protein in transgenic *Brassica napus* plant is shown in FIG. 9. In FIG. 9, 15 µg of total protein from the immature inflorescence of each plant was applied. SW18: *B. napus* CMS line; Westar: *Brassica napus* cv Westar; and #32 transgenic line with 4.7-kbp BamHI/Hpa I fragment. In the transgenic plant #32 having BamHI-HpaI fragments containing cds6, it was confirmed that ORF125 protein was reduced with restoration of pollen fertility. Using the orf125 gene of the mitochondrial DNA as the probe, Southern hybridization was carried for the BamHI digested total DNAs of the transgenic plant #32. The result of the Southern blot analysis of orf125 locus transgenic *Brassica napus* plant is shown in FIG. 10. In FIG. 10, BamHI digested of total DNA (5 µg *Brassica napus*) hybridized with orf125 probe. SW18: *B. napus* CMS line; Westar: *Brassica napus* cv Westar; #32: transgenic line with 4.7-kbp BamHI/Hpa I fragment. The signal intensity of orf125 showed no difference between the transformant and the male sterile plant. Therefore, it is presumed that the introduced gene fragment does not reduce copy number of orf125, but reduces the protein content by regulating the gene expression, resulting in restoring pollen fertility.

Example 17

Agricultural Traits of the Plant to which a Fertility Restoring Gene was Introduced by Transformation The cytoplasm male sterile rapeseed line SW18 (Japanese Patent Laid-open Publication No. 1-218530) was crossed with the transgenic plant #32 to which cds6BT was intoroduced, to yield $F_1$ seed. Selfed-seeds of this #32 (hereinafter, a self pollinating generation of the transformant will be represented using T (Transgenic)$_n$. For example, self pollinating 1st generation is $T_1$) were collected. These seeds were grown in an open field of a western part of Canada in summer of 2002 to study agricultural traits.

$F_1$ seed and $T_1$ seed were grown side together with cultivar Westar as a control plant in a parallel alignment in the same field to study the flowering time (number of days from planting to an end of flower), plant height, and a yield per row (Table 1). The flowering time showed no large difference between the cultivar Westar and the transgenic lines ($F_1$ and $T_1$). The plant height showed somewhat lower in $F_1$ line, but no large difference was found. For the yield, when means of every line were compared with Westar assigned to 100, the $F_1$ line showed the yield as higher than Westar as about 19%. All plants of Westar and transgenic lines ($F_1$ and $T_1$) did not lodge before harvest and thus, there is no problem in tolerance against lodging.

From these results, rapeseed having the DNA of the present invention has no problem in agricultural traits. Further, in the case where the $F_1$ line produced by crossing with the cytoplasmic male sterile plant was selected, the yield becomes higher than those of Westar and $T_1$ lines. It is suggested that even if the pollen parent has been segregated in the hemizygote (1 copy of the gene has been held), an effect of making the $F_1$ cultivar appears.

TABLE 1

Agronomic traits of $F_1$ and $T_1$ lines in filed trials, 2002 at Lethbride, Canada

| Cross | Plots | Generations | End of flower (DAP)* | Plant height (cm) | Yields (gram/row) | Average Yields** |
|---|---|---|---|---|---|---|
| SW18 × cdsSBT/pKM424-#32 | 1 | $F_1$ | 69 | 100 | 395 | |
| | 2 | | 71 | 100 | 609 | 502(119) |
| cds6BT/pKM424-#32-self | 1 | $T_1$ | 69 | 110 | 414 | |
| | 2 | | 71 | 105 | 482 | 448(106) |
| Westar (control OP variety) | 1 | | 69 | 100 | 356 | |
| | 2 | | 67 | 105 | 488 | 422(100) |

*Days after planting. This data represent flowering time of the each line.
**Numbers in parenthesis are ratio of average yields calculating by average yield data of Westar as 100.

Example 18

Selection of Homozygote

The plant transforming vector cds6BT/pKM424 described in Example 4-1 was used for transformation based on the procedure described in Example 6, and the obtained transformant #32 was used for selection of the homozygote. The selfed-seeds were collected for $T_0$ plant of #32 and a segregation ratio of pollen fertility was studied. As the result, the segregation ratio matching with the segregation ratio, fertile: sterile=3:1, expected in the case having heterozygous dominant 1 gene in Mendelian inheritance, was obtained (Table 2). Therefore, it was found that 1 copy of the fertility restoration gene was introduced to this plant. The selfed seed of the fertile plant of the $T_1$ generation was planted, 1 plant of each $T_1$ generation was assigned to 1 line, and plantlets of each of 20 seeds produced in 10 lines in total were screened by PCR.

PCR was carried out by using the PCR primer b site described in Example 7, and the homozygous line was selected by using, as an index, the fact that all plants of $T_2$ generation showed positive signal in PCR. The pollen fertility of these homozygotes was similar with pollen fertility of $T_0$ generation, and the seed fertility was also similar with that of the transformant parent, Westar.

TABLE 2

Segregation of $F_1$ and $T_1$ plants derived from a transgenic plant #32 carrying an radish Rf gene

| | | Male fertility | | Observed | Expected |
|---|---|---|---|---|---|
| Crosses | Generations | Fertile | Sterile | ratio | raio |
| SW18 × cds6BT/pKM424-#32 | $F_1$ | 100 | 102 | 0.98:1 | 1:1 |
| cds6BT/pKM424-#32-self | $T_1$ | 137 | 48 | 2.85:1 | 3:1 |

Example 19

Evaluation of Seed Glucosinolate (GSL) Contents of Transgenic Rf Line

In order to evaluate the seed glucosinolate contents, test paper containing glucose oxidase/peroxidase were used (Robbelen and Theis 1980). The yellow test paper may turn into blue that result from reaction for glucose derived from GSLs by hydrolization of endogenous myrosinase.

Selfed-seeds of fertile T2 plants of #32 line were harvested by bagging at the field in Canada (see Example 17, Table 1). In parallel, selfed-seeds of cv. Westar grown at the same field were also harvested by bagging as negative control of the analysis.

Five seeds of T2 plants of Rf (#32) line, cv. Westar and Isuzu-natane (a high GSL variety) were analyzed. Seeds of each line were crushed in motor and pestle. 100 μl of distilled water was added to obtain seed extract into each motor and incubate five minutes under room temperature. After incubation, TES-tapes (Shionogi co. &Ltd) were immersed into the seed extracts until the paper imbibed the moisture contents.

FIG. 11 shows the results of TES-tape analysis. In FIG. 11, Sample #1-10: T3 seeds of T2 plants derived from #32 plants transformed with cds6BT/pKM424 (see Example 4-2). Sample #11-15: seeds of spring canola cultivar Westar (10 micormolar/g seed). Seeds were harvested from the plants grown at the filed in Canada, 2003 summer. All the seeds were harvested by self-pollination controlling with bagging. Sample #16: seeds of Japanese rapeseed cultivar cv. Isuzu-natane that contains high GSL in the seeds. A band on the paper slip results from high glucose content derived from GSLs in Isuzu-natane seeds.

A canola culivar, Westar, showed no color change. Yellow-colored TES tape was turned into blue in high GSL variety, Isuzu-natane. Deep blue color of high GSL sample Isuzu-natane indicates high GSL contents of the sample. No color change was observed in yellow TES tape neither with T2 samples, suggesting that the GSL contents of the T2 sample was similar to that of negative control spring canola variety cv. Westar (10 micomolar/g seed, by L. Serynk 1995).

Röbellen and Theis (1980) Glucosinolates and breeding for meal quality. In: *Brassica* crops and wild allies. Biology and breeding S. Tsunoda, K. Hinata and C. Gomez-Campo (eds.) Japan Scientific Society Press, Tokyo pp 287-299

Catalogue of oilseed rape cultivars 1995 ed. compiled by Larry Serynk, Mycogen Plant Sciences 5649 E Buckeye Road Madison, Wis. USA 53716

INDUSTRIAL APPLICABILITY

According to the present invention, Rf gene, particularly the Rf1 gene derived from radish was isolated and a structure thereof was determined. According to the present invention, a means for establishing a rapeseed fertility restorer line can be provided using the isolated Rf gene.

The invention claimed is:
1. An isolated DNA encoding a protein involved in restoration of a cytoplasmic male sterile individual to fertility, selected from the group consisting of:
   (1) an isolated DNA which encodes a protein having the amino acid sequence of SEQ ID NO. 26;
   (2) an isolated DNA which encodes a protein having an amino acid sequence that is 92% or more homologous to the amino acid sequence of SEQ ID NO. 26;
   (3) an isolated DNA having 95% of or higher homology to a DNA sequence encoding a protein having the amino acid sequence of SEQ ID NO. 26;
   (4) an isolated DNA which encodes a protein having the amino acid sequence of SEQ ID NO. 19;
   (5) an isolated DNA which encodes a protein having an amino acid sequence that is 92% or more homologous to the amino acid sequence of SEQ ID NO. 19;
   (6) an isolated DNA having 95% or higher homology to a DNA sequence encoding a protein having the amino acid sequence of SEQ ID NO. 19;
   (7) an isolated DNA having the nucleotide sequence of SEQ ID NO. 18; and
   (8) an isolated DNA having 95% or higher homology to the nucleotide sequence of SEQ ID NO. 18.
2. The isolated DNA of claim 1 which further encodes a signal peptide sequence to translocate to a mitochondria at the amino terminal or has a sequence of -LysAspGluLeu- at the carboxyl terminal.
3. The isolated DNA of claim 1 which encodes a protein having the amino acid sequence of SEQ ID NO. 26.
4. The isolated DNA of claim 1 which encodes the protein having the amino acid sequence of SEQ ID NO. 19.
5. The isolated DNA of claim 1, of any of the following:
   (1) an isolated DNA having the nucleotide sequence of SEQ ID NO. 18;
   or
   (2) an isolated DNA having 95% or higher homology to the nucleotide sequence of or SEQ ID NO. 18.
6. A vector comprising the isolated DNA of claim 1.
7. A transformant containing the isolated DNA of claim 1.
8. The transformant of claim 7 which is a transformed plant.
9. A method for the restoration of the cytoplasmic male sterile individual to fertility, wherein the DNA encoding a protein involved in restoration of a cytoplasmic male sterile individual to fertility of claim 1 is introduced with an induction type promoter into a cell or tissue of a *Brassica* plant; wherein the promoter is positioned with respect to the DNA encoding the protein, involved in restoration of a cytoplasmic male sterile individual to fertility, to enable transcription thereof in the cell or tissue; so that the cell or tissue can regulate expression of the cytoplasmic male sterile gene.
10. An isolated DNA of claim 1 further comprising a promoter DNA having the sequence from 3754th to 5091th nucleotides of the nucleotide sequence of SEQ ID NO. 1, wherein the promoter DNA is positioned with respect to the DNA sequence encoding a protein involved in restoration of a cytoplasmic male sterile individual to fertility to enable transcription thereof.
11. A plant-transforming vector which comprises the isolated DNA of claim 1 and a promoter DNA having an ability of transcribing an mRNA at least in an anther, wherein the promoter is positioned with respect to the DNA encoding a protein involved in restoration of a cytoplasmic male sterile individual to fertility to enable transcription thereof.
12. A method for producing a hybrid plant seed having fertility restoration ability, comprising the step of crossing a mother and a pollen parent, wherein a cytoplasmic male sterile line plant is used as the mother, and a transformed plant comprising the DNA of claim 1 is used as the pollen parent.
13. An isolated DNA of claim 1 encoding a protein involved in restoration of a cytoplasmic male sterile individual to fertility, selected from the group consisting of:
   (1) an isolated DNA which encodes a protein having the amino acid sequence of SEQ ID NO. 26;
   (2) an isolated DNA which encodes a protein having an amino acid sequence that is 92% or more homologous to the amino acid sequence of SEQ ID NO. 26; and
   (3) an isolated DNA having 95% or higher homology to a DNA sequence encoding a protein having the amino acid sequence of SEQ ID NO. 26.
14. An isolated DNA of claim 1 encoding a protein involved in restoration of a cytoplasmic male sterile individual to fertility, selected from the group consisting of:
   (1) an isolated DNA which encodes a protein having the amino acid sequence of SEQ ID NO. 26; and (2) an isolated DNA which encodes a protein having an amino acid sequence that is 92% or more homologous to the amino acid sequence of SEQ ID NO. 26.
15. An isolated DNA of claim 1 encoding a protein involved in restoration of a cytoplasmic male sterile individual to fertility, selected from the group consisting of:
   (1) an isolated DNA which encodes a protein having the amino acid sequence of SEQ ID NO. 19;
   (2) an isolated DNA which encodes a protein having an amino acid sequence that is 92% or more homologous to the amino acid sequence of SEQ ID NO. 19; and
   (3) an isolated DNA having 95% or higher homology to a DNA sequence encoding a protein having the amino acid sequence of SEQ ID NO. 19.
16. An isolated DNA of claim 1 encoding a protein involved in restoration of a cytoplasmic male sterile individual to fertility, selected from the group consisting of:
   (1) an isolated DNA which encodes a protein having the amino acid sequence of SEQ ID NO. 19; and
   (2) an isolated DNA which encodes a protein having an amino acid sequence that is 92% or more homologous to the amino acid sequence of SEQ ID NO. 19.
17. A transformant containing the isolated DNA of claim 1 which is a plant cell or plant tissue of a *Brassica* plant or a transformed *Brassica* plant.
18. The transformant of claim 17 which is a transformed *Brassica* plant.
19. A transformant having a cytoplasmic male sterile gene wherein the isolated DNA of claim 1 is introduced with an induction type promoter into a cell of the transformant, wherein the promoter is positioned with respect to the isolated DNA to enable transcription thereof in the transformant, so that the transformant can regulate expression of the cytoplasmic male sterile gene, wherein the transformant is a cell or tissue of a *Brassica* plant or a transformed *Brassica* plant.
20. A method for maintaining a cytoplasmic male sterile Brassica line by crossing said line with the transformant of claim 17.
21. A seed, pollen, protoplast, cell, vegetative portion, hypocotyl, gamete or root, which is obtained from the transformant of claim 17 and which comprises said isolated DNA.
22. A transformed Brassica plant having the vector of claim 11.
23. A hybrid plant seed of a *Brassica* plant having fertility restoration ability, produced by crossing a mother, which is a cytoplasmic male sterile line *Brassica* plant; with a pollen parent, which is a fertility restoring line *Brassica plant*, which is a transformed plant containing the isolated DNA of claim 1.

24. The hybrid plant seed according to claim 23, wherein the cytoplasmic male sterile line plant of said mother is a cytoplasmic male sterile hybrid line comprising cytoplasm derived from Ogura or Kosena radish.

25. The hybrid plant seed according to claim 23, wherein the *Brassica* plant belongs to the species *Brassica napus*.

26. A seed, pollen, protoplast, cell, vegetative portion, hypocotyl, gamete, or root, each comprising a DNA of claim 1; which is obtained by planting and growing a hybrid plant seed of a *Brassica* plant having fertility restoration ability, produced by crossing a mother, which is a cytoplasmic male sterile line *Brassica* plant; with a pollen parent, which is a fertility restoring line *Brassica* plant, which is a transformed plant containing said isolated DNA.

27. A seed, pollen, protoplast, cell, vegetative portion, hypocotyl, gamete or root of a *Brassica* plant, each of which comprises the isolated DNA of claim 1.

28. A transformant or transformed plant comprising (1) the isolated DNA of claim 1, (2) a vector containing said isolated DNA, or (3) a plant-transforming vector containing said isolated DNA and a promoter DNA having the ability to transcribe an mRNA at least in an anther, wherein the promoter is positioned with respect to said isolated DNA to enable transcription thereof; wherein the transformant or transformed plant is homozygous for a gene encoding the protein involved in restoration of a cytoplasmic male sterile plant to fertility encoded by said isolated DNA; and wherein the transformant is a cell or tissue of a *Brassica* plant and the transformed plant is a *Brassica* plant.

29. A vector comprising the isolated DNA of claim 2.

30. A vector comprising the isolated DNA of claim 10.

31. The transformant of claim 17 wherein the *Brassica* plant is a *Brassica napus* plant.

32. A method for maintaining a cytoplasmic male sterile *Brassica* line by crossing the line with the transformant of claim 19.

33. The isolated DNA of claim 1 having the nucleotide sequence of SEQ ID NO. 18.

34. A vector comprising the isolated DNA of claim 33.

35. A transformant containing the isolated DNA of claim 33 which is a plant cell or plant tissue of a *Brassica* plant or a transformed *Brassica* plant.

36. An isolated DNA which encodes a protein involved in restoration of a cytoplasmic male sterile individual to fertility wherein the protein consists of the amino acid sequence of SEQ ID NO. 19.

* * * * *

SEQUENCE LISTING

<160> NUMBER OF SEQ ID NOS: 41

<210> SEQ ID NO 1
<211> LENGTH: 8553
<212> TYPE: DNA
<213> ORGANISM: Raphanus sativus

<400> SEQUENCE: 1

```
atttaaattt tatacttaat atgtatttaa actctccaat gcaataaggg atataaacaa      60
aaggtattca tagatgttat gtattcgtac accgatgtat tcgtatacct taaatatatg     120
tatacttatg tatacatata cttgtgtatt cgtacacctt aagtattcga tgggttatgt     180
tggtattcgt atattttatg tatttgtaca ccttatgtat acttatgtat atgtacacct     240
tatgtatttg tacatcttaa gtattagatg agttatgttg atattcgtac accttatgta     300
ttcgtacacc ttctgtatac cttaggtatt cgtacacctt aggtatttgt acacctaagg     360
tattcgtaca ccttatgtat acttatgtat acgtacacct tatatattcg aacaccttag     420
atattcgtac atcttatgta tacgtatact tatttcttga gttatagtga attagattgt     480
attaaacgtt agacataggg ttccggattt atccaagggt tccagattgt ttcagattct     540
ggatttaccc aatggttctg gatttaccca agggttccgg atttaggatt caaggtttag     600
agtttaggat tttaggttta gtgttttgtt gatgattttt aatatttaag ataaatgtag     660
acaaatttgt tcttcctacc attttgacaa aaaatgaaag atctatgtag gtttccaagt     720
ttattaaatt tacccagatt tatgaaaatt atccataaat ttatataatt ttatgaataa     780
tttatcattt atttgggtaa atttcataaa tatgaaagtt tcttttatgg gtcaaaatgt     840
ataatttatt cggattctgg atttacccaa gggttccgga tttacccaag gattccagat     900
ttaggattca tggtttagag tttaggagtt tatgtttagt gttttgttga tgattttaaa     960
tatttaagat aagaagttta tgcgagagaa tttggtcaaa ctcaggttga gtcttaactt    1020
cttaagacat aaaaatcact agatacttga catggaggca ccaaattatc ctatattttt    1080
tggacttaat cttggtgtac ccctagagta aaccttaagg ttcaccaacc aatagaaatc    1140
actcatttca cagttgatat cttttaaaaa agtaaacaaa atattgtcga gttatattac    1200
atttttaaaa taaaatatt aaaaaataaa aataataata tatgcaaaaa aaagattt     1260 ttaaaaagat tttaatttcg tcaacaaaac actaaactct aaactctaaa tcctaaaccc    1320
ttggataaat actaaaccct aaattaaaaa cattaaacca taatagtatt tttaagattt    1380
aatgttttag tgtttagtgt ttttgattta gaatttagga ttatccaagt gtttatgatt    1440
tatccaaggg tttagggttt agaatttagg gtttagggtt tagagtttaa aattatccaa    1500
gggtctaggg tatacccaag ggtttagggt ttaggattta gggtttaggg tttagaattt    1560
agggtttagg gtttagagtt taaaattatc caagggttta gggtataccc aagggtttag    1620
ggtttaggat ttagggttta aggtttagtg ttttttgacg atattaaaaa tagttttcaa    1680
```

```
aaattcattt tttgtaacgg ctattatttt tttttatat tttatttatt ttaaaaacat    1740
aatataactt gacaatattt tcttttcttt ttaaaaaaaa tattaattat gaaatacttg    1800
attcctattg gttgggtgaa cctaaatgtt cactctaggg gtgaacctaa ggataactct    1860
attttttggg gtgaaatagc actatagcgg atatctttttt caatagatta taagcacggc    1920
tctacctatg actaatcaag aacttgggat gattggaaat ctgcaggttg tactcaatat    1980
gggattatat tggttctaac aagtagatat gatccttgaa aattaaagtt attagatcag    2040
ttcatcgtga aaggtgtagg gtttgtcatt ttattaacaa atttgtcatt tcattaacaa    2100
tttttgtcat tttataaaca tgaaaattat aacgaatgca ctttgctgcc agatcccaat    2160
ttgtcatttt attttgggga aaaaatgta gcatttcgtg agtgtttcta ttttggcaa     2220 aaacaaaaag tgtgagatca attttgacca aaaaaaatg taagattcac gtaggtttcc    2280
aaatttatta aatttaccca actatattaa aattaaatgt agacaaattt gttttcctgc    2340
cattttggca aaaaatgaag gatctatgaa ggtttccaag tttattaaat ttactcagat    2400
ttatgataat tatccataaa tttacataat tttatgaatt atcatttatt tgggtagatt    2460
tcataaatat gaaagtttct tttatgagtc aaaatgtata atttattggg taactttcat    2520 aaatttttaga atttacatcg atttatatt aattcgtata gatttatgtt gactttatat    2580
atgaaaaaat atgtattata ttaaaagtag ttgctcatat atgattttta aatattaaat    2640
atgatccaaa agtttaatga ataagaatg tttatggaat ttacaaaagt tagttgttaa    2700
aagttagtgg gaaaaaaatt ttttttttata ggcaaagtgg attttgggtc ccacgaaatt    2760
acttttccaa cttgccaagt ttaataggca aaaaggttaa aaatgtcata aatttattct    2820
ctctctacta ggttgcccaa ttgcctaata taaacttgag gtggcctatt tttctaattc    2880
aaacttaaaa gttgcccttt cccctaattg acccataaaa gaatgaaaga catttttctt    2940
ttccaaatta caatccctag ataattttat tttgtaggtg cattccatcg gttatgatta    3000
cagaatagct acgcttctct attgattctt attgcgccgt tggtgacgtt ttccatggaa    3060
tcaagtagtg ttttatctcc tatcactaac aacatattca tagattttgt ttatcacttg    3120
ttctgtgttc ctgatcatat acttgactca gtttctgtga tttcatcaag ttttttgagaa    3180 cagaagaagc aaaaaagaaa acgagcagag ctgctcttac aatgtttttaa ccgtgagtga    3240 taaatttatt tacataaaag tattttaaaa atagatttaa tcaaccaatt taatatatta    3300 ttttatatttt agttcatttt tttttgacat ctttttatatt tagttagaa caccctctatt    3360 tgagtacaac atagattata atgataaatt tataaaatag cataatttttt tattttcatt    3420 gttttatgat aaaattctaa ataacaataa ttataatatt attatattac taattgcaaa    3480
aattaattaa tacattattt tataataaat atttaaaacg ttgggtagga ttttgttaga    3540 ttttttttcaa caaattttgt tatagctaaa ataaaattca aatgtattgt taaaattgat    3600
tttttttttt tttgattatt aagatttaat ataaataaac atatatgtca tattaaaatat    3660 ttaactaagt ggtcctaatc tttgaactag gggtgggcgt tcgggtacct attcgggttt    3720
cggttcgagt ctattcggat ttcggatttt tggggtcaaa gattttagcc ccattcggtt    3780
atttctaaat tacggttcgg gttcggttcg gatccttgcg gattcggttc gggttcggat    3840
aacccgttta aattatttttc aaaatttttaa aatttcatta tatattttaa acttttcgaa    3900
atttgtaaac aaaataatat attacatata aatttcaata atatgtgtcg aagtaccaaa    3960
acttaacatg taaattggtt tgatttggat atttggatag aaaatcaatc atattttata    4020 tattttttggt gttttgagta tgctttaact atttatacat gtacttttta atgttttttat    4080
```

```
atattttcta gtattttgaa caatttaaaa gtattatata tatttagat gcttttaat    4140 atatattcaa tctaaaaata gttaaatata tatgtatatt aatctatttc ggatacattc    4200
ggatatccaa aatattttgg ttcggatcgg gttcggtttt ggttcttaa ataccaaaaa    4260 tttaaaccta ttcggatatt caattaattt cggttcggat ttggtattac ttttgcagat    4320
cggattcggt tcggttcttt ggattcagtt ttttgtcca gccctactct gaacagtaga    4380 taaaaatag aaccctaaat taataggtta gattttggtt aggtctttct aattagtatg    4440
gagattctcg attccttctc attgcagtgt ggtatgtcca actcattgtt tatgtacata    4500
tccaatttag ttttgagtca aatgtttagt tacttaagag ttgaatgaaa taggggatga    4560
tattgatggc caaggttctc ccaaagtaaa taactttgtt tatatttaa gttagcttat    4620 aacatcaata aaaatgtcat taactggttc aataaaaatg tcattaactg gttcctctaa    4680
tataattatt taacacacct ggctgttgat aaattttat gatcgtttaa taatttaga    4740 agtggatagt ctgtaaatgg tctttgattg gtcgtcttga tttttaaaag tggactaaac    4800
aagaaggctt agtaataaat actgaaccgg aactctactg gtttcaatag ctcggtttat    4860
caatttctct cggctctggg tttagtgaat catgtggccc tgtgggttta aacaaggaac    4920
tcaatcaatc aactggtgac aaatctgaac cggaaattgt ataattcaaa ctgaaccggt    4980
tcttgtaaaa caaatggaac ccgtttgtac tttatctctc gtttattttc tcagtcacga    5040
gtttttttta gagatcgacg aagaacaaaa tttaggcgaa acaaaaataa aatgttggct    5100
agggtttgtg gattcaagtg ttcttcttct cctgctgagt ctgcggctag attgttctgt    5160
acgagatcga ttcgtgatac tctggccaag gcaagcggag agagttgcga agcaggtttt    5220
ggaggagaga gtttgaagct gcaaagtggg tttcatgaaa tcaaaggttt agaggatgcg    5280
attgatttgt tcagtgacat gcttcgatct cgtcctttac cttctgtggt tgatttctgt    5340
aaattgatgg gtgtggtggt gagaatgaaa cgcccggatc ttgtgatttc tctctatcag    5400
aagatggaaa ggaaacagat tcgatgtgat atatacagct tcaatattct gataaaatgt    5460
ttctgcagct gctctaagct ccccttttgct ttgtctacat ttggtaagat caccaagctt    5520
ggactccacc ctgatgttgt taccttcacc accctgctcc atggattatg tgtggaagat    5580
agggtttctg aagccttgga ttttttttcat caaatgtttg aaacgacatg taggcccaat    5640
gtcgtaacct tcaccacttt gatgaacggt cttttgccgcg agggtagaat tgtcgaagcc    5700
gtagctctgc ttgatcggat gatggaagat ggtctccagc ctacccagat tacttatgga    5760
acaatcgtag atgggatgtg taagaaggga gatactgtgt ctgcactgaa tctgctgagg    5820
aagatggagg aggtgagcca catcataccc aatgttgtaa tctatagtgc aatcattgat    5880
agcctttgta aagacggacg tcatagcgat gcacaaaatc ttttcactga aatgcaagag    5940
aaaggaatct ttcccgattt atttacctac aacagtatga tagttggttt ttgtagctct    6000
ggtagatgga gcgacgcgga gcagttgttg caagaaatgt tagaaaggaa gatcagccct    6060
gatgttgtaa cttataatgc tttgatcaat gcatttgtca aggaaggcaa gttctttgag    6120
gctgaagaat tatacgatga gatgcttcca agggtataa tccctaatac aatcacatat    6180
agttcaatga tcgatggatt ttgcaaacag aatcgtcttg atgctgctga gcacatgttt    6240
tatttgatgg ctaccaaggg ctgctctccc aacctaatca ctttcaatac tctcatagac    6300
ggatattgtg gggctaagag gatagatgat ggaatggaac ttctccatga gatgactgaa    6360
acaggattag ttgctgacac aactacttac aacactctta ttcacgggtt ctatctggtg    6420
ggcgatctta atgctgctct agaccttta caagagatga tctctagtgg tttgtgccct    6480
```

```
gatatcgtta cttgtgacac tttgctggat ggtctctgcg ataatgggaa actaaaagat    6540
gcattggaaa tgtttaaggt tatgcagaag agtaagaagg atcttgatgc tagtcacccc    6600
ttcaatggtg tggaacctga tgttcaaact tacaatatat tgatcagcgg cttgatcaat    6660
gaagggaagt ttttagaggc cgaggaatta tacgaggaga tgccccacag gggtatagtc    6720
ccagatacta tcacctatag ctcaatgatc gatggattat gcaagcagag ccgcctagat    6780
gaggctacac aaatgtttga ttcgatgggt agcaagagct tctctccaaa cgtagtgacc    6840
tttactacac tcattaatgg ctactgtaag gcaggaaggg ttgatgatgg gctggagctt    6900
ttctgcgaga tgggtcgaag agggatagtt gctaacgcaa ttacttacat cactttgatt    6960
tgtggttttc gtaaagtggg taatattaat ggggctctag acattttcca ggagatgatt    7020
tcaagtggtg tgtatcctga taccattacc atccgcaata tgctgactgg tttatggagt    7080
aaagaggaac taaaagggc agtggcaatg cttgagaaac tgcagatgag tatggtatgt    7140
aagtttctgt tcagtctatg tattttttat ataaacaaga atgtatacat tcttttgtgt    7200
gtagcttcag attgatgata cacgttctgg aattaaccat tggtttggtt ttgcattgta    7260
ggatctatca tttgggggat gaatgatcaa agatttcctt ctgtttgcgc agcagagctt    7320
caatgtcatt ttgtttctgc tgctgcatgt atacccacct aatgtttgat caaatcgttg    7380
aatagagtga tcatagtgaa aaattgtgtg gttagtaagt tattttgctg ctattctaat    7440
gacagccttt tatgcgtcta ttgtctgggc ttaataaatt tgaccatttc caattaaatt    7500
ccatacactt gtttcacgca agattattgg tctgaactaa agaggcacac cttccagaag    7560
atttcaggtg ttaaaagatg tttaggtgtc tgcccgttct gtagctgtca ccatggttat    7620
cgtcaagctc ggtcttcatg agagctgata gctgtgatgc catcttcctc ctcttcttca    7680
tattggctct gtcctgcctt gtctgctccc atgtgggttc aggaggagat catgttcttt    7740
taatcttggt ggaaatgttg ttgtcgctta tgcttctctg gttcgcctct tgacttgctt    7800
agcttcattc tttatctcca aattgctatg aaatcaattt accataagta gaataaactt    7860
gcagattcat tctattattg cttaagcttt tgttaatcaa caaagaaacc agagacgaga    7920
aatacaaact ctataagctt ctcttttttc tttcttgata gtaaaaccgg ttagagagta    7980
gagattgatc atatgaacta aaaatcgata ctaaaacggt ttggctccga cttataaacc    8040
ggaaccccac cgttttgcat ctctctctca aacatcacac aatgtccaag atgaagaagt    8100
atttgtgttg tcatctctct gggtgaggag atgcaaatgt tatattctaa ttgttttcag    8160
tgcttggtct aacttttttta agagattact cccagtggtt ggatcaaaga aagagtcaac    8220
attgcattgt gtaaggtgac gaaaactgag ttaaagtaag tgagaacaat acttcaatgc    8280
ttttcttgtg acaacctgtg taatcatcgc atttgaatat atatgtatat gatgcttatg    8340
atgaagctat gagaataggc aaataggggtc tgtgttattt ccctgcgatt ctagattctg    8400
atttgttttt ccttcttaat atttagatta ggtggtcttg cttatcctgt tttagtatta    8460
gagtcggagt tttggggatg aatcatcccg gatgatatat acaattgtgt attttatgaa    8520
tttcagtttt tagtggataa tgaacacgtt aac                                 8553
```

<210> SEQ ID NO 2
<211> LENGTH: 2064
<212> TYPE: DNA
<213> ORGANISM: Raphanus sativus

<400> SEQUENCE: 2

```
atgttggcta gggtttgtgg attcaagtgt tcttcttctc ctgctgagtc tgcggctaga      60
```

-continued

```
ttgttctgta cgagatcgat tcgtgatact ctggccaagg caagcggaga gagttgcgaa    120
gcaggttttg gaggagagag tttgaagctg caaagtgggt tcatgaaat caaaggttta    180 gaggatgcga ttgatttgtt cagtgacatg cttcgatctc gtcctttacc ttctgtggtt    240
gatttctgta aattgatggg tgtggtggtg agaatggaac gcccggatct tgtgatttct    300
ctctatcaga agatggaaag gaaacagatt cgatgtgata tatacagctt caatattctg    360
ataaaatgtt tctgcagctg ctctaagctc ccctttgctt tgtctacatt tggtaagatc    420
accaagcttg gactccaccc tgatgttgtt accttcacca ccctgctcca tggattatgt    480
gtggaagata gggtttctga agccttggat tttttttcatc aaatgtttga aacgacatgt    540
aggcccaatg tcgtaacctt caccactttg atgaacggtc tttgccgcga gggtagaatt    600
gtcgaagccg tagctctgct tgatcggatg atggaagatg gtctccagcc tacccagatt    660
acttatggaa caatcgtaga tgggatgtgt aagaagggag atactgtgtc tgcactgaat    720
ctgctgagga agatggagga ggtgagccac atcatacccca tgttgtaat ctatagtgca    780 atcattgata gcctttgtaa agacggacgt catagcgatg cacaaaatct tttcactgaa    840
atgcaagaga aggaatcttt tcccgattta tttacctaca acagtatgat agttggtttt    900
tgtagctctg gtagatggag cgacgcggag cagttgttgc aagaaatgtt agaaaggaag    960
atcagccctg atgttgtaac ttataatgct ttgatcaatg catttgtcaa ggaaggcaag   1020
ttctttgagg ctgaagaatt atacgatgag atgcttccaa ggggtataat ccctaataca   1080
atcacatata gttcaatgat cgatggattt tgcaaacaga atcgtcttga tgctgctgag   1140
cacatgtttt atttgatggc taccaagggc tgctctccca acctaatcac tttcaatact   1200
ctcatagacg atattgtgg ggctaagagg atagatgatg gaatggaact tctccatgag   1260
atgactgaaa caggattagt tgctgacaca actacttaca cactcttat tcacgggttc   1320 tatctggtgg gcgatcttaa tgctgctcta gacctttac aagagatgat ctctagtggt   1380
ttgtgccctg atatcgttac ttgtgacact ttgctggatg gtctctgcga taatgggaaa   1440
ctaaaagatg cattggaaat gtttaaggtt atgcagaaga gtaagaagga tcttgatgct   1500
agtcacccct tcaatggtgt ggaacctgat gttcaaactt acaatatatt gatcagcggc   1560
ttgatcaatg aagggaagtt tttagaggcc gaggaattat acgaggagat gccccacagg   1620
ggtatagtcc cagatactat cacctatagc tcaatgatcg atggattatg caagcagagc   1680
cgcctagatg aggctacaca aatgtttgat tcgatgggta gcaagagctt ctctccaaac   1740
gtagtgacct ttactacact cattaatggc tactgtaagg caggaagggt tgatgatggg   1800
ctggagcttt tctgcgagat gggtcgaaga gggatagttg ctaacgcaat tacttacatc   1860
actttgattt gtggttttcg taaagtgggt aatattaatg gggctctaga cattttccag   1920
gagatgattt caagtggtgt gtatcctgat accattacca tccgcaatat gctgactggt   1980
ttatggagta agaggaact aaaaagggca gtggcaatgc ttgagaaact gcagatgagt   2040
atggatctat catttggggg atga                                          2064
```

<210> SEQ ID NO 3
<211> LENGTH: 687
<212> TYPE: PRT
<213> ORGANISM: Raphanus sativus

<400> SEQUENCE: 3

```
Met Leu Ala Arg Val Cys Gly Phe Lys Cys Ser Ser Ser Pro Ala Glu
 1               5                  10                  15
```

```
Ser Ala Ala Arg Leu Phe Cys Thr Arg Ser Ile Arg Asp Thr Leu Ala
                20                  25                  30
Lys Ala Ser Gly Glu Ser Cys Glu Ala Gly Phe Gly Gly Glu Ser Leu
             35                  40                  45
Lys Leu Gln Ser Gly Phe His Glu Ile Lys Gly Leu Glu Asp Ala Ile
         50                  55                  60
Asp Leu Phe Ser Asp Met Leu Arg Ser Arg Pro Leu Pro Ser Val Val
 65                  70                  75                  80
Asp Phe Cys Lys Leu Met Gly Val Val Arg Met Glu Arg Pro Asp
                 85                  90                  95
Leu Val Ile Ser Leu Tyr Gln Lys Met Glu Arg Lys Gln Ile Arg Cys
                100                 105                 110
Asp Ile Tyr Ser Phe Asn Ile Leu Ile Lys Cys Phe Cys Ser Cys Ser
                115                 120                 125
Lys Leu Pro Phe Ala Leu Ser Thr Phe Gly Lys Ile Thr Lys Leu Gly
            130                 135                 140
Leu His Pro Asp Val Val Thr Phe Thr Thr Leu Leu His Gly Leu Cys
145                 150                 155                 160
Val Glu Asp Arg Val Ser Glu Ala Leu Asp Phe Phe His Gln Met Phe
                165                 170                 175
Glu Thr Thr Cys Arg Pro Asn Val Val Thr Phe Thr Thr Leu Met Asn
                180                 185                 190
Gly Leu Cys Arg Glu Gly Arg Ile Val Glu Ala Val Ala Leu Leu Asp
                195                 200                 205
Arg Met Met Glu Asp Gly Leu Gln Pro Thr Gln Ile Thr Tyr Gly Thr
210                 215                 220
Ile Val Asp Gly Met Cys Lys Lys Gly Asp Thr Val Ser Ala Leu Asn
225                 230                 235                 240
Leu Leu Arg Lys Met Glu Glu Val Ser His Ile Ile Pro Asn Val Val
                245                 250                 255
Ile Tyr Ser Ala Ile Ile Asp Ser Leu Cys Lys Asp Gly Arg His Ser
                260                 265                 270
Asp Ala Gln Asn Leu Phe Thr Glu Met Gln Glu Lys Gly Ile Phe Pro
            275                 280                 285
Asp Leu Phe Thr Tyr Asn Ser Met Ile Val Gly Phe Cys Ser Ser Gly
    290                 295                 300
Arg Trp Ser Asp Ala Glu Gln Leu Leu Gln Glu Met Leu Glu Arg Lys
305                 310                 315                 320
Ile Ser Pro Asp Val Val Thr Tyr Asn Ala Leu Ile Asn Ala Phe Val
                325                 330                 335
Lys Glu Gly Lys Phe Phe Glu Ala Glu Glu Leu Tyr Asp Glu Met Leu
            340                 345                 350
Pro Arg Gly Ile Ile Pro Asn Thr Ile Thr Tyr Ser Ser Met Ile Asp
        355                 360                 365
Gly Phe Cys Lys Gln Asn Arg Leu Asp Ala Ala Glu His Met Phe Tyr
    370                 375                 380
Leu Met Ala Thr Lys Gly Cys Ser Pro Asn Leu Ile Thr Phe Asn Thr
385                 390                 395                 400
Leu Ile Asp Gly Tyr Cys Gly Ala Lys Arg Ile Asp Asp Gly Met Glu
                405                 410                 415
Leu Leu His Glu Met Thr Glu Thr Gly Leu Val Ala Asp Thr Thr Thr
            420                 425                 430
Tyr Asn Thr Leu Ile His Gly Phe Tyr Leu Val Gly Asp Leu Asn Ala
        435                 440                 445
```

Ala Leu Asp Leu Leu Gln Glu Met Ile Ser Ser Gly Leu Cys Pro Asp
    450                 455                 460

Ile Val Thr Cys Asp Thr Leu Asp Gly Leu Cys Asp Asn Gly Lys
465                 470                 475                 480

Leu Lys Asp Ala Leu Glu Met Phe Lys Val Met Gln Lys Ser Lys Lys
                485                 490                 495

Asp Leu Asp Ala Ser His Pro Phe Asn Gly Val Glu Pro Asp Val Gln
                500                 505                 510

Thr Tyr Asn Ile Leu Ile Ser Gly Leu Ile Asn Glu Gly Lys Phe Leu
                515                 520                 525

Glu Ala Glu Glu Leu Tyr Glu Glu Met Pro His Arg Gly Ile Val Pro
    530                 535                 540

Asp Thr Ile Thr Tyr Ser Ser Met Ile Asp Gly Leu Cys Lys Gln Ser
545                 550                 555                 560

Arg Leu Asp Glu Ala Thr Gln Met Phe Asp Ser Met Gly Ser Lys Ser
                565                 570                 575

Phe Ser Pro Asn Val Val Thr Phe Thr Thr Leu Ile Asn Gly Tyr Cys
                580                 585                 590

Lys Ala Gly Arg Val Asp Asp Gly Leu Glu Leu Phe Cys Glu Met Gly
    595                 600                 605

Arg Arg Gly Ile Val Ala Asn Ala Ile Thr Tyr Ile Thr Leu Ile Cys
610                 615                 620

Gly Phe Arg Lys Val Gly Asn Ile Asn Gly Ala Leu Asp Ile Phe Gln
625                 630                 635                 640

Glu Met Ile Ser Ser Gly Val Tyr Pro Asp Thr Ile Thr Ile Arg Asn
                645                 650                 655

Met Leu Thr Gly Leu Trp Ser Lys Glu Glu Leu Lys Arg Ala Val Ala
                660                 665                 670

Met Leu Glu Lys Leu Gln Met Ser Met Asp Leu Ser Phe Gly Gly
    675                 680                 685

<210> SEQ ID NO 4
<211> LENGTH: 25
<212> TYPE: DNA
<213> ORGANISM: Artificial
<220> FEATURE:
<223> OTHER INFORMATION: Probe

<400> SEQUENCE: 4
gaagcaaaaa agaaaacgag cagag                                    25

<210> SEQ ID NO 5
<211> LENGTH: 25
<212> TYPE: DNA
<213> ORGANISM: Artificial
<220> FEATURE:
<223> OTHER INFORMATION: Probe

<400> SEQUENCE: 5
ccaaaaatcc gaaatccgaa tagac                                    25

<210> SEQ ID NO 6
<211> LENGTH: 20
<212> TYPE: DNA
<213> ORGANISM: Artificial
<220> FEATURE:
<223> OTHER INFORMATION: Probe

<400> SEQUENCE: 6

```
ctcggctctg ggtttagtga                                              20

<210> SEQ ID NO 7
<211> LENGTH: 20
<212> TYPE: DNA
<213> ORGANISM: Artificial
<220> FEATURE:
<223> OTHER INFORMATION: Probe

<400> SEQUENCE: 7
tccacaaacc ctagccaaca                                              20

<210> SEQ ID NO 8
<211> LENGTH: 24
<212> TYPE: DNA
<213> ORGANISM: Artificial
<220> FEATURE:
<223> OTHER INFORMATION: Probe

<400> SEQUENCE: 8
gcttatgctt ctctggttcg cctc                                         24

<210> SEQ ID NO 9
<211> LENGTH: 27
<212> TYPE: DNA
<213> ORGANISM: Artificial
<220> FEATURE:
<223> OTHER INFORMATION: Probe

<400> SEQUENCE: 9
ctcagttttc gtcaccttac acaatgc                                      27

<210> SEQ ID NO 10
<211> LENGTH: 23
<212> TYPE: DNA
<213> ORGANISM: Artificial
<220> FEATURE:
<223> OTHER INFORMATION: Probe

<400> SEQUENCE: 10
gattcctttc tcttgcattt cag                                          23

<210> SEQ ID NO 11
<211> LENGTH: 23
<212> TYPE: DNA
<213> ORGANISM: Artificial
<220> FEATURE:
<223> OTHER INFORMATION: Probe

<400> SEQUENCE: 11
atctcgtcct ttaccttctg tgg                                          23

<210> SEQ ID NO 12
<211> LENGTH: 18
<212> TYPE: DNA
<213> ORGANISM: Artificial
<220> FEATURE:
<223> OTHER INFORMATION: Probe

<400> SEQUENCE: 12
cgggatccgc tcacaatt                                                18

<210> SEQ ID NO 13
<211> LENGTH: 100
<212> TYPE: DNA
<213> ORGANISM: Artificial
<220> FEATURE:
```

```
<223> OTHER INFORMATION: Probe

<400> SEQUENCE: 13
gcggatccca atttcattct gcatcactct ccctgtcgtt atcgacctcg caaggttttt      60
gaaacggccg aaacgggaag tgacaatacc gcttttcttc                          100

<210> SEQ ID NO 14
<211> LENGTH: 100
<212> TYPE: DNA
<213> ORGANISM: Artificial
<220> FEATURE:
<223> OTHER INFORMATION: Probe

<400> SEQUENCE: 14
ggaattcact aactttacat tcagtaggag tgagattatg acaaaaagtg gacaattttt      60
cgaaaaaggt aatcatgcat ttatatgctg aagaaaagcg                          100

<210> SEQ ID NO 15
<211> LENGTH: 3306
<212> TYPE: DNA
<213> ORGANISM: Raphanus sativus

<400> SEQUENCE: 15
caattaattt cggttcggat ttggtattac ttttgcagat cggattcggt tcggttcttt      60
ggattcagtt tttttgtcca gccctactct gaacagtaga taaaaaatag aaccctaaat     120
taataggtta gattttggtt aggtctttct aattagtatg gagattctcg attccttctc     180
attgcagtgt ggtatgtcca actcattgtt tatgtacata tccaatttag ttttgagtca     240
aatgtttagt tacttaagag ttgaatgaaa taggggatga tattgatggc caaggttctc     300
ccaaagtaaa taactttgtt tatatttttaa gttagcttat aacatcaata aaaatgtcat     360
taactggttc aataaaaatg tcattaactg gttcctctaa tataattatt taacacacct     420
ggctgttgat aaattttat gatcgtttaa taatttaga agtggatagt ctgtaaatgg      480
tctttgattg gtcgtcttga tttttaaaag tggactaaac aagaaggctt agtaataaat     540
actgaaccgg aactctactg gtttcaatag ctcggtttat caatttctct cggctctggg     600
tttagtgaat catgtggccc tgtgggttta acaaggaac tcaatcaatc aactggtgac      660
aaatctgaac cggaaattgt ataattcaaa ctgaaccggt tcttgtaaaa caaatggaac     720
ccgtttgtac tttatctctc gtttatttc tcagtcacga gttttttta gagatcgacg      780 aagaacaaaa tttaggcgaa acaaaaataa aatgttggct agggtttgtg gattcaagtg     840
ttcttcttct cctgctgagt ctgcggctag attgttctgt acgagatcga ttcgtgatac      900
tctggccaag gcaagcggag agagttgcga agcaggtttt ggaggagaga gtttgaagct     960
gcaaagtggg tttcatgaaa tcaaaggttt agaggatgcg attgatttgt tcagtgacat    1020
gcttcgatct cgtcctttac cttctgtggt tgatttctgt aaattgatgg gtgtggtggt    1080
gagaatggaa cgcccggatc ttgtgatttc tctctatcag aagatggaaa ggaaacagat    1140
tcgatgtgat atatacagct tcaatattct gataaaatgt ttctgcagct gctctaagct    1200 ccccttttgct ttgtctacat ttggtaagct caccaagctt ggactccacc ctgatgttgt    1260
taccttcacc accctgctcc acggattgtg cgtggaagat agggtttctg aagctttgaa    1320
tttgtttcat caaatgtttg aaacgacatg taggcccaat gtcgtaacct tcaccacttt    1380
gatgaacggc ctttgccgcg agggtagaat tgtcgaagcc gtagctctgc ttgatcggat    1440
gatggaagat ggtctccagc ctacccagat tacttatgga acaatcgtag atgggatgtg    1500
```

-continued

```
taagaaggga gatactgtgt ctgcactgaa tctgctgagg aagatggagg aggtgagcca    1560
catcataccc aatgttgtaa tctatagtgc aatcattgat agcctttgta aagacggacg    1620
tcatagcgat gcacaaaatc ttttcactga aatgcaagag aaaggaatct ttcccgattt    1680
atttacctac aacagtatga tagttggttt ttgtagctct ggtagatgga gcgacgcgga    1740
gcagttgttg caagaaatgt tagaaaggaa gatcagccct gatgttgtaa cttataatgc    1800
tttgatcaat gcatttgtca aggaaggcaa gttctttgag gctgaagaat tatacgatga    1860
gatgcttcca aggggtataa tccctaatac aatcacatat agttcaatga tcgatggatt    1920
ttgcaaacag aatcgtcttg atgctgctga gcacatgttt tatttgatgg ctaccaaggg    1980
ctgctctccc aacctaatca ctttcaatac tctcatagac ggatattgtg gggctaagag    2040
gatagatgat ggaatggaac ttctccatga gatgactgaa acaggattag ttgctgacac    2100
aactacttac aacactctta ttcacggggtt ctatctggtg ggcgatctta atgctgctct    2160
agacctttta caagagatga tctctagtgg tttgtgccct gatatcgtta cttgtgacac    2220
tttgctggat ggtctctgcg ataatgggaa actaaaagat gcattggaaa tgtttaaggt    2280
tatgcagaag agtaagaagg atcttgatgc tagtcacccc ttcaatggtg tggaacctga    2340
tgttcaaact tacaatatat tgatcagcgg cttgatcaat gaagggaagt ttttagaggc    2400
cgaggaatta tacgaggaga tgccccacag gggtatagtc ccagatacta tcacctatag    2460
ctcaatgatc gatggattat gcaagcagag ccgcctagat gaggctacac aaatgtttga    2520
ttcgatgggt agcaagagct ctctccaaa cgtagtgacc tttactacac tcattaatgg    2580
ctactgtaag gcaggaaggg ttgatgatgg gctggagctt ttctgcgaga tgggtcgaag    2640
agggatagtt gctaacgcaa ttacttacat cactttgatt tgtggttttc gtaaagtggg    2700
taatattaat ggggctctag acattttcca ggagatgatt tcaagtggtg tgtatcctga    2760
taccattacc atccgcaata tgctgactgg tttatggagt aaagaggaac taaaagggc    2820
agtggcaatg cttgagaaac tgcagatgag tatggtatgt aagtttctgt tcagtctatg    2880
tattttttat ataaacaaga atgtatacat tcttttgtgt gtagcttcag attgatgata    2940
cacgttctgg aattaaccat tggtttggtt ttgcattgta ggatctatca tttgggggat    3000
gaatgatcaa agattttctt ctgtttgcgc agcagagctt caatgtcatt tgtttctgc    3060
tgctgcatgt ataccctact aatgtttgat caaatcgttg aatagagtga tcatagtgaa    3120
aaattgtgtg gttagtaagt tattttgctg ctattctaat gacagccttt tatgcgtcta    3180
ttgtctgggc ttaataaatt tgaccatttc caattaaatt ccatacactt gtttcacgca    3240
agattattgg tctgaactaa agaggcacac cttccagaag atttcaggtg ttaaaagatg    3300
tttagg                                                              3306
```

<210> SEQ ID NO 16
<211> LENGTH: 2064
<212> TYPE: DNA
<213> ORGANISM: Raphanus sativus

<400> SEQUENCE: 16

```
atgttggcta gggtttgtgg attcaagtgt tcttcttctc ctgctgagtc tgcggctaga     60
ttgttctgta cgagatcgat tcgtgatact ctggccaagg caagcggaga gagttgcgaa    120
gcaggttttg gaggagagag tttgaagctg caaagtgggt tcatgaaaat caaaggttta    180
gaggatgcga ttgatttgtt cagtgacatg cttcgatctc gtcctttacc ttctgtggtt    240
gatttctgta aattgatggg tgtggtggtg agaatggaac gcccggatct tgtgatttct    300
```

```
ctctatcaga agatggaaag gaaacagatt cgatgtgata tatacagctt caatattctg    360
ataaaatgtt tctgcagctg ctctaagctc ccctttgctt tgtctacatt tggtaagctc    420
accaagcttg gactccaccc tgatgttgtt accttcacca ccctgctcca cggattgtgc    480
gtggaagata gggtttctga agctttgaat ttgtttcatc aaatgtttga aacgacatgt    540
aggcccaatg tcgtaacctt caccactttg atgaacggtc tttgccgcga gggtagaatt    600
gtcgaagccg tagctctgct tgatcggatg atggaagatg tctccagcc tacccagatt    660
acttatggaa caatcgtaga tgggatgtgt aagaagggag atactgtgtc tgcactgaat    720
ctgctgagga gatggagga ggtgagccac atcatcccca atgttgtaat ctatagtgca    780
atcattgata gcctttgtaa agacggacgt catagcgatg cacaaaatct tttcactgaa    840
atgcaagaga aaggaatctt tcccgattta tttacctaca acagtatgat agttggtttt    900
tgtagctctg gtagatggag cgacgcggag cagttgttgc aagaaatgtt agaaaggaag    960
atcagccctg atgttgtaac ttataatgct ttgatcaatg catttgtcaa ggaaggcaag   1020
ttctttgagg ctgaagaatt atacgatgag atgcttccaa ggggtataat ccctaataca   1080
atcacatata gttcaatgat cgatggattt tgcaaacaga atcgtcttga tgctgctgag   1140
cacatgtttt atttgatggc taccaagggc tgctctccca acctaatcac tttcaatact   1200
ctcatagacg gatattgtgg ggctaagagg atagatgatg aatgaaact tctccatgag   1260
atgactgaaa caggattagt tgctgacaca actacttaca acactcttat tcacgggttc   1320
tatctggtgg gcgatcttaa tgctgctcta gaccttttac aagagatgat ctctagtggt   1380
ttgtgccctg atatcgttac ttgtgacact ttgctggatg gtctctgcga taatgggaaa   1440
ctaaaagatg cattggaaat gtttaaggtt atgcagaaga gtaagaagga tcttgatgct   1500
agtcacccct tcaatggtgt ggaacctgat gttcaaactt acaatatatt gatcagcggc   1560
ttgatcaatg aagggaagtt tttagaggcc gaggaattat acgaggagat gccccacagg   1620
ggtatagtcc cagatactat cacctatagc tcaatgatcg atggattatg caagcagagc   1680
cgcctagatg aggctacaca aatgtttgat tcgatgggta gcaagagctt ctctccaaac   1740
gtagtgacct ttactacact cattaatggc tactgtaagg caggaagggt tgatgatggg   1800
ctggagcttt tctgcgagat gggtcgaaga gggatagttg ctaacgcaat tacttacatc   1860
actttgattt gtggttttcg taaagtgggt aatattaatg gggctctaga cattttccag   1920
gagatgattt caagtggtgt gtatcctgat accattacca tccgcaatat gctgactggt   1980
ttatggagta agaggaact aaaaagggca gtggcaatgc ttgagaaact gcagatgagt   2040
atggatctat catttggggg atga                                          2064
```

<210> SEQ ID NO 17
<211> LENGTH: 688
<212> TYPE: PRT
<213> ORGANISM: Raphanus sativus
<220> FEATURE:
<221> NAME/KEY: Xaa
<222> LOCATION: (688)..(688)
<223> OTHER INFORMATION: Xaa can be any amino acid
<220> FEATURE:
<221> NAME/KEY: misc_feature
<222> LOCATION: (688)..(688)
<223> OTHER INFORMATION: Xaa can be any naturally occurring amino acid

<400> SEQUENCE: 17

Met Leu Ala Arg Val Cys Gly Phe Lys Cys Ser Ser Ser Pro Ala Glu
1               5                   10                  15

Ser Ala Ala Arg Leu Phe Cys Thr Arg Ser Ile Arg Asp Thr Leu Ala

```
                    20                  25                  30
Lys Ala Ser Gly Glu Ser Cys Glu Ala Gly Phe Gly Gly Glu Ser Leu
                35                  40                  45
Lys Leu Gln Ser Gly Phe His Glu Ile Lys Gly Leu Glu Asp Ala Ile
            50                  55                  60
Asp Leu Phe Ser Asp Met Leu Arg Ser Arg Pro Leu Pro Ser Val Val
65                  70                  75                  80
Asp Phe Cys Lys Leu Met Gly Val Val Arg Met Glu Arg Pro Asp
                85                  90                  95
Leu Val Ile Ser Leu Tyr Gln Lys Met Glu Arg Lys Gln Ile Arg Cys
                100                 105                 110
Asp Ile Tyr Ser Phe Asn Ile Leu Ile Lys Cys Phe Ser Cys Ser
                115                 120                 125
Lys Leu Pro Phe Ala Leu Ser Thr Phe Gly Lys Leu Thr Lys Leu Gly
                130                 135                 140
Leu His Pro Asp Val Val Thr Phe Thr Thr Leu Leu His Gly Leu Cys
145                 150                 155                 160
Val Glu Asp Arg Val Ser Glu Ala Leu Asn Leu Phe His Gln Met Phe
                165                 170                 175
Glu Thr Thr Cys Arg Pro Asn Val Val Thr Phe Thr Thr Leu Met Asn
                180                 185                 190
Gly Leu Cys Arg Glu Gly Arg Ile Val Glu Ala Val Ala Leu Leu Asp
                195                 200                 205
Arg Met Met Glu Asp Gly Leu Gln Pro Thr Gln Ile Thr Tyr Gly Thr
                210                 215                 220
Ile Val Asp Gly Met Cys Lys Lys Gly Asp Thr Val Ser Ala Leu Asn
225                 230                 235                 240
Leu Leu Arg Lys Met Glu Glu Val Ser His Ile Ile Pro Asn Val Val
                245                 250                 255
Ile Tyr Ser Ala Ile Ile Asp Ser Leu Cys Lys Asp Gly Arg His Ser
                260                 265                 270
Asp Ala Gln Asn Leu Phe Thr Glu Met Gln Glu Lys Gly Ile Phe Pro
                275                 280                 285
Asp Leu Phe Thr Tyr Asn Ser Met Ile Val Gly Phe Cys Ser Ser Gly
                290                 295                 300
Arg Trp Ser Asp Ala Glu Gln Leu Leu Gln Glu Met Leu Glu Arg Lys
305                 310                 315                 320
Ile Ser Pro Asp Val Val Thr Tyr Asn Ala Leu Ile Asn Ala Phe Val
                325                 330                 335
Lys Glu Gly Lys Phe Phe Glu Ala Glu Leu Tyr Asp Glu Met Leu
                340                 345                 350
Pro Arg Gly Ile Ile Pro Asn Thr Ile Thr Tyr Ser Ser Met Ile Asp
                355                 360                 365
Gly Phe Cys Lys Gln Asn Arg Leu Asp Ala Ala Glu His Met Phe Tyr
                370                 375                 380
Leu Met Ala Thr Lys Gly Cys Ser Pro Asn Leu Ile Thr Phe Asn Thr
385                 390                 395                 400
Leu Ile Asp Gly Tyr Cys Gly Ala Lys Arg Ile Asp Asp Gly Met Glu
                405                 410                 415
Leu Leu His Glu Met Thr Glu Thr Gly Leu Val Ala Asp Thr Thr Thr
                420                 425                 430
Tyr Asn Thr Leu Ile His Gly Phe Tyr Leu Val Gly Asp Leu Asn Ala
                435                 440                 445
```

-continued

```
Ala Leu Asp Leu Leu Gln Glu Met Ile Ser Ser Gly Leu Cys Pro Asp
    450                 455                 460

Ile Val Thr Cys Asp Thr Leu Leu Asp Gly Leu Cys Asp Asn Gly Lys
465                 470                 475                 480

Leu Lys Asp Ala Leu Glu Met Phe Lys Val Met Gln Lys Ser Lys Lys
                485                 490                 495

Asp Leu Asp Ala Ser His Pro Phe Asn Gly Val Glu Pro Asp Val Gln
                500                 505                 510

Thr Tyr Asn Ile Leu Ile Ser Gly Leu Ile Asn Glu Gly Lys Phe Leu
            515                 520                 525

Glu Ala Glu Glu Leu Tyr Glu Glu Met Pro His Arg Gly Ile Val Pro
    530                 535                 540

Asp Thr Ile Thr Tyr Ser Ser Met Ile Asp Gly Leu Cys Lys Gln Ser
545                 550                 555                 560

Arg Leu Asp Glu Ala Thr Gln Met Phe Asp Ser Met Gly Ser Lys Ser
                565                 570                 575

Phe Ser Pro Asn Val Val Thr Phe Thr Thr Leu Ile Asn Gly Tyr Cys
                580                 585                 590

Lys Ala Gly Arg Val Asp Asp Gly Leu Glu Leu Phe Cys Glu Met Gly
            595                 600                 605

Arg Arg Gly Ile Val Ala Asn Ala Ile Thr Tyr Ile Thr Leu Ile Cys
    610                 615                 620

Gly Phe Arg Lys Val Gly Asn Ile Asn Gly Ala Leu Asp Ile Phe Gln
625                 630                 635                 640

Glu Met Ile Ser Ser Gly Val Tyr Pro Asp Thr Ile Thr Ile Arg Asn
                645                 650                 655

Met Leu Thr Gly Leu Trp Ser Lys Glu Glu Leu Lys Arg Ala Val Ala
                660                 665                 670

Met Leu Glu Lys Leu Gln Met Ser Met Asp Leu Ser Phe Gly Gly Xaa
            675                 680                 685
```

<210> SEQ ID NO 18
<211> LENGTH: 2073
<212> TYPE: DNA
<213> ORGANISM: Raphanus sativus

<400> SEQUENCE: 18

```
atgttggcta gggtttgtgg attcaagtgt tcttcttctc ctgctgtgtc tgcggctaga      60
ttgttctgta cgagatcgat tcgtgatact ctggccaagg caagcaggga tggagagagt     120
tgcgaagcag gttttggagg agagagtttg aagctgcaaa gtgggtttca tgaaatcaaa     180
ggtttagagg atgcgattga tttgttcagt gacatgcttc gatctcgtcc tttaccttct     240
gtggttgatt tctgtaaatt gatgggtgtg gtggtgagga tgaaacgccc ggatgttgtg     300
atttctctcc ataagaagat ggaaatgcgg cgcattccat gtgatgcata cagcttcaat     360
attctgataa agtgtttctg cagctgctct aagctgccct tgctttgtc tacatttggt      420 aagctcacca agcttggact ccaccctgat gttgttacct tcaccaccct tctccacgga     480
ttgtgtgtgg aaaataggg ttctgaagct ttgaatttgt tcatcaaat gtttgaaacg       540 rcatgtaggc ccaatgtcgt aaccttcacc actttgatga acggtctttg ccgcgagggt     600
agaattgtcg aagccgtagc tctacttgat cggatgatga agatggtct ccagcctacc      660 cagattactt atggaacaat cgtagatggg atgtgtaaga agggagatac tgtgtctgca     720
ctgaatctgc tgaggaagat ggaggaggtg agccacatca tacccaatgt tgtaatctat     780
agtgcaatca ttgatagcct tgtaaagac ggacgtcata gcgattctca aaatctttc       840
```

```
actgaaatgc aagagaaagg aatctttcca gatttattta cctacaactg tatgatcaac    900
gggttttgta gctctggtag atggatcgac gcggagcagt tgttgcaaga aatgttagaa    960
aggaagatca gccctgatgt tgtaacttat aatgctttga tcaatgcatt tgtcaaggaa   1020
ggcaagttct ttgaggctga agaattatac gatgagatgc ttcctagggg tataatccct   1080
aatacaatca catatagttc aatgatcgat ggattttgca acagaatcg tcttgatgct    1140
gctgagcaca tgttttattt gatgcctacc aagggctgct ctccggacgt attcactttc   1200
aatactctca tagacggata tcgtgggggct aagaggatag atgatggaat ggaacttctc   1260
catgagatga ctgaagcagg attagttgct aacacagtta cttacaacac tcttattcac   1320
gggttttgtc aggtgggcga tcttactgct gctctagacc ttctacatga atgattttct   1380
agtggtgtgt gccctaatgt cgttacttgt agcactttgc tggatggtct ctgcgataac   1440
gggaaactaa aagatgcatg gaactgtttt aaggttatgc agaagagtaa gatggatctt   1500
gatgctagtc accccttcaa tggtgtggaa cctgatgttc aaacttacaa tatattgatc   1560
agcggcttga tcaatgaagg gaagttttta gaggctgagg aattatacaa ggagatgccc   1620
cacagggggta tagtcccaga tactattacc tatagctcaa tgatcgatgg actatgcaag   1680
cagagccgcc tggatgaggc tacacaaatg tttgattcga tgggtagcaa gagcttctct   1740
ccaaacgtag tgacctttac tacactcatt gatggctact gtaaagcagg aagggttgat   1800
gatgggctgg agcttttctg cgagatgggt agaagaggga tagttgctaa tacaattact   1860
tacatcactt tgattcgtgg tttttcgcaat gtgggtaata ttaatggggc tctagacatt   1920
ttccaggaga tgatttcaag tggtgtgtat cctggtatca ttactatccg cagtatgctg   1980
actggtttat ggagtaaaga ggaactaaaa aggacagtgg caatgcttga ggaactgcag   2040
atgagtgtgg ggtatcagtt ggaggatgaa tga                                2073

<210> SEQ ID NO 19
<211> LENGTH: 691
<212> TYPE: PRT
<213> ORGANISM: Raphanus sativus
<220> FEATURE:
<221> NAME/KEY: misc_feature
<222> LOCATION: (691)..(691)
<223> OTHER INFORMATION: Xaa can be any naturally occurring amino acid
<220> FEATURE:
<221> NAME/KEY: misc_feature
<222> LOCATION: (693)..(693)
<223> OTHER INFORMATION: Xaa can be any amino acid

<400> SEQUENCE: 19

Met Leu Ala Arg Val Cys Gly Phe Lys Cys Ser Ser Ser Pro Ala Val
1               5                   10                  15

Ser Ala Ala Arg Leu Phe Cys Thr Arg Ser Ile Arg Asp Thr Leu Ala
            20                  25                  30

Lys Ala Ser Arg Asp Gly Glu Ser Cys Glu Ala Gly Phe Gly Gly Glu
        35                  40                  45

Ser Leu Lys Leu Gln Ser Gly Phe His Glu Ile Lys Gly Leu Glu Asp
    50                  55                  60

Ala Ile Asp Leu Phe Ser Asp Met Leu Arg Ser Arg Pro Leu Pro Ser
65                  70                  75                  80

Val Val Asp Phe Cys Lys Leu Met Gly Val Val Arg Met Lys Arg
                85                  90                  95

Pro Asp Val Val Ile Ser Leu His Lys Lys Met Glu Met Arg Arg Ile
                100                 105                 110
```

-continued

```
Pro Cys Asp Ala Tyr Ser Phe Asn Ile Leu Ile Lys Cys Phe Cys Ser
    115                 120                 125
Cys Ser Lys Leu Pro Phe Ala Leu Ser Thr Phe Gly Lys Leu Thr Lys
130                 135                 140
Leu Gly Leu His Pro Asp Val Val Thr Phe Thr Thr Leu Leu His Gly
145                 150                 155                 160
Leu Cys Val Glu Asn Arg Gly Ser Glu Ala Leu Asn Leu Phe His Gln
                165                 170                 175
Met Phe Glu Thr Thr Cys Arg Pro Asn Val Val Thr Phe Thr Thr Leu
            180                 185                 190
Met Asn Gly Leu Cys Arg Glu Gly Arg Ile Val Glu Ala Val Ala Leu
        195                 200                 205
Leu Asp Arg Met Met Glu Asp Gly Leu Gln Pro Thr Gln Ile Thr Tyr
    210                 215                 220
Gly Thr Ile Val Asp Gly Met Cys Lys Lys Gly Asp Thr Val Ser Ala
225                 230                 235                 240
Leu Asn Leu Leu Arg Lys Met Glu Glu Val Ser His Ile Ile Pro Asn
                245                 250                 255
Val Val Ile Tyr Ser Ala Ile Ile Asp Ser Leu Cys Lys Asp Gly Arg
            260                 265                 270
His Ser Asp Ser Gln Asn Leu Phe Thr Glu Met Gln Glu Lys Gly Ile
        275                 280                 285
Phe Pro Asp Leu Phe Thr Tyr Asn Cys Met Ile Asn Gly Phe Cys Ser
    290                 295                 300
Ser Gly Arg Trp Ile Asp Ala Glu Gln Leu Leu Gln Glu Met Leu Glu
305                 310                 315                 320
Arg Lys Ile Ser Pro Asp Val Val Thr Tyr Asn Ala Leu Ile Asn Ala
                325                 330                 335
Phe Val Lys Glu Gly Lys Phe Phe Glu Ala Glu Leu Tyr Asp Glu
            340                 345                 350
Met Leu Pro Arg Gly Ile Ile Pro Asn Thr Ile Thr Tyr Ser Ser Met
    355                 360                 365
Ile Asp Gly Phe Cys Lys Gln Asn Arg Leu Asp Ala Ala Glu His Met
370                 375                 380
Phe Tyr Leu Met Pro Thr Lys Gly Cys Ser Pro Asp Val Phe Thr Phe
385                 390                 395                 400
Asn Thr Leu Ile Asp Gly Tyr Arg Gly Ala Lys Arg Ile Asp Asp Gly
                405                 410                 415
Met Glu Leu Leu His Glu Met Thr Glu Ala Gly Leu Val Ala Asn Thr
            420                 425                 430
Val Thr Tyr Asn Thr Leu Ile His Gly Phe Cys Gln Val Gly Asp Leu
    435                 440                 445
Thr Ala Ala Leu Asp Leu Leu His Glu Met Ile Ser Ser Gly Val Cys
450                 455                 460
Pro Asn Val Val Thr Cys Ser Thr Leu Leu Asp Gly Leu Cys Asp Asn
465                 470                 475                 480
Gly Lys Leu Lys Asp Ala Trp Glu Leu Phe Lys Val Met Gln Lys Ser
                485                 490                 495
Lys Met Asp Leu Asp Ala Ser His Pro Phe Asn Gly Val Glu Pro Asp
            500                 505                 510
Val Gln Thr Tyr Asn Ile Leu Ile Ser Gly Leu Ile Asn Glu Gly Lys
    515                 520                 525
Phe Leu Glu Ala Glu Glu Leu Tyr Lys Glu Met Pro His Arg Gly Ile
530                 535                 540
```

Val Pro Asp Thr Ile Thr Tyr Ser Ser Met Ile Asp Gly Leu Cys Lys
545                 550                 555                 560

Gln Ser Arg Leu Asp Glu Ala Thr Gln Met Phe Asp Ser Met Gly Ser
            565                 570                 575

Lys Ser Phe Ser Pro Asn Val Val Thr Phe Thr Leu Ile Asp Gly
        580                 585                 590

Tyr Cys Lys Ala Gly Arg Val Asp Asp Gly Leu Glu Leu Phe Cys Glu
        595                 600                 605

Met Gly Arg Arg Gly Ile Val Ala Asn Thr Ile Thr Tyr Ile Thr Leu
610                 615                 620

Ile Arg Gly Phe Arg Asn Val Gly Asn Ile Asn Gly Ala Leu Asp Ile
625                 630                 635                 640

Phe Gln Glu Met Ile Ser Ser Gly Val Tyr Pro Gly Ile Ile Thr Ile
                645                 650                 655

Arg Ser Met Leu Thr Gly Leu Trp Ser Lys Glu Glu Leu Lys Arg Thr
                660                 665                 670

Val Ala Met Leu Glu Glu Leu Gln Met Ser Val Gly Tyr Gln Leu Glu
            675                 680                 685

Asp Glu Xaa
    690

<210> SEQ ID NO 20
<211> LENGTH: 516
<212> TYPE: DNA
<213> ORGANISM: Raphanus raphanistrum

<400> SEQUENCE: 20
aatggaacgc ccggatcttg tgatttctct ctatcaaaag atggaaagga aacagattcc     60
atgtgatgta tacagcttta atattctgat aaaatgtttc tgcagttgct ctaagcttcc    120
ctttgctttg tctacatttg gtaagatcac caagcttgga ctccaccctg atgttgctac    180
cttcaacacc ctgctccacg gattatgtct tgataagagg gtttctgaag ccttggattt    240
gtttcatcaa atgtttgaaa cgacatgtag gccgaacatc ataacgttta ccacgctgat    300
gaacggtctt tgctacgagg gtagagttgt cgaagctgta gctctgcttg atcggatgct    360
agaagatggt ctccagcctg accagattac ttacggaaca attgtagacg ggatgtgtaa    420
gatgggagac actgtgtctg cattgaatct tctgaggaag atggaggagt tgagccacat    480
caaacccaat gtggtaatct atagtgccat cattga                              516

<210> SEQ ID NO 21
<211> LENGTH: 171
<212> TYPE: PRT
<213> ORGANISM: Raphanus raphanistrum

<400> SEQUENCE: 21

Met Glu Arg Pro Asp Leu Val Ile Ser Leu Tyr Gln Lys Met Glu Arg
1               5                   10                  15

Lys Gln Ile Pro Cys Asp Val Tyr Ser Phe Asn Ile Leu Ile Lys Cys
            20                  25                  30

Phe Cys Ser Cys Ser Lys Leu Pro Phe Ala Leu Ser Thr Phe Gly Lys
        35                  40                  45

Ile Thr Lys Leu Gly Leu His Pro Asp Val Ala Thr Phe Asn Thr Leu
    50                  55                  60

Leu His Gly Leu Cys Leu Asp Lys Arg Val Ser Glu Ala Leu Asp Leu
65                  70                  75                  80

```
Phe His Gln Met Phe Glu Thr Thr Cys Arg Pro Asn Ile Ile Thr Phe
                85                  90                  95
Thr Thr Leu Met Asn Gly Leu Cys Tyr Glu Gly Arg Val Val Glu Ala
            100                 105                 110
Val Ala Leu Leu Asp Arg Met Leu Glu Asp Gly Leu Gln Pro Asp Gln
        115                 120                 125
Ile Thr Tyr Gly Thr Ile Val Asp Gly Met Cys Lys Met Gly Asp Thr
    130                 135                 140
Val Ser Ala Leu Asn Leu Leu Arg Lys Met Glu Glu Leu Ser His Ile
145                 150                 155                 160
Lys Pro Asn Val Val Ile Tyr Ser Ala Ile Ile
                165                 170

<210> SEQ ID NO 22
<211> LENGTH: 2073
<212> TYPE: DNA
<213> ORGANISM: Raphanus
<220> FEATURE:
<221> NAME/KEY: misc_feature
<222> LOCATION: (113)..(118)
<223> OTHER INFORMATION: n can be any nucleotide

<400> SEQUENCE: 22
```

| | | | | | |
|---|---|---|---|---|---|
| atgttggcta | gggtttgtgg | attcaagtgt | tcttcttctc | ctgctgwgtc | tgcggctaga | 60 |
| ttgttctgta | cgagatcgat | tcgtgatact | ctggccaagg | caagcrgrga | krnnnnnngt | 120 |
| tgcgaagcag | gttttggagg | agagagtttg | aagctgcaaa | gtgggtttca | tgaaatcaaa | 180 |
| ggtttagagg | atgcgattga | tttgttcagt | gacatgcttc | gatctcgtcc | tttaccttct | 240 |
| gtggttgatt | tctgtaaatt | gatgggtgtg | gtggtgagra | tgaacgccc | ggatsttgtg | 300 |
| atttctctcy | atmaraagat | ggaaakgmrr | crsattcsat | gtgatryata | cagcttyaat | 360 |
| attctgataa | artgtttctg | cagytgctct | aagctbccct | ttgctttgtc | tacatttggt | 420 |
| aagmtcacca | agcttggact | ccaccctgat | gttgytacct | tcamcaccct | kctccaygga | 480 |
| ttrtgystkg | awrakagggk | ttctgaagcy | ttgratttkt | ttcatcaaat | gtttgaaacg | 540 |
| rcatgtaggc | csaayrtcrt | aacsttyacc | ackytgatga | acggtctttg | cyrcgagggt | 600 |
| agarttgtcg | aagcygtagc | tctrcttgat | cggatgmtrg | aagatggtct | ccagcctrmc | 660 |
| cagattactt | ayggaacaat | ygtagayggg | atgtgtaaga | wgggagayac | tgtgtctgca | 720 |
| ytgaatctkc | tgaggaagat | ggaggagktg | agccacatca | wacccaatgt | kgtaatctat | 780 |
| agtgcmatca | ttgatagcct | ttgtaaagac | ggacgtcata | gcgatkcwca | aaatcttttc | 840 |
| actgaaatgc | aagagaaagg | aatctttccm | gatttattta | cctacaacwg | tatgatmrwy | 900 |
| ggkttttgta | gctctggtag | atggakcgac | gcggagcagt | tgttgcaaga | aatgttagaa | 960 |
| aggaagatca | gccctgatgt | tgtaacttat | aatgctttga | tcaatgcatt | tgtcaaggaa | 1020 |
| ggcaagttct | ttgaggctga | agaattatac | gatgagatgc | ttccwagggg | tataatccct | 1080 |
| aatacaatca | catatagttc | aatgatcgat | ggattttgca | aacagaatcg | tcttgatgct | 1140 |
| gctgagcaca | tgtttttattt | gatgsctacc | aagggctgct | ctccsracst | awtcactttc | 1200 |
| aatactctca | tagacggata | tygtggggct | aagaggatag | atgatggaat | ggaacttctc | 1260 |
| catgagatga | ctgaarcagg | attagttgct | racacaryta | cttacaacac | tcttattcac | 1320 |
| gggttytrtc | wggtgggcga | tcttamtgct | gctctagacc | ttytacawga | gatgatytct | 1380 |
| agtggtktgt | gccctratrt | cgttacttgt | rrcactttgc | tggatggtct | ctgcgataay | 1440 |
| gggaaactaa | aagtgcatk | ggaamtgttt | aaggttatgc | agaagagtaa | gawggatctt | 1500 |

```
gatgctagtc accccttcaa tggtgtggaa cctgatgttc aaacttacaa tatattgatc    1560
agcggcttga tcaatgaagg gaagttttta gaggcygagg aattatacra ggagatgccc    1620
cacaggggta tagtcccaga tactatyacc tatagctcaa tgatcgatgg aytatgcaag    1680
cagagccgcc trgatgaggc tacacaaatg tttgattcga tgggtagcaa gagcttctct    1740
ccaaacgtag tgacctttac tacactcatt ratggctact gtaargcagg aagggttgat    1800
gatgggctga agcttttctg cgagatgggt mgaagaggga tagttgctaa yrcaattact    1860
tacatcactt tgattygtgg ttttcgyaaw gtgggtaata ttaatggggc tctagacatt    1920
ttccaggaga tgatttcaag tggtgtgtat cctgrtayca ttacyatccg cartatgctg    1980
actggtttat ggagtaaaga ggaactaaaa aggrcagtgg caatgcttga graactgcag    2040
atgagtrtgg rkywwymrtt kgrggrwkra tga                                 2073

<210> SEQ ID NO 23
<211> LENGTH: 2073
<212> TYPE: DNA
<213> ORGANISM: Raphanus
<220> FEATURE:
<221> NAME/KEY: misc_feature
<222> LOCATION: (113)..(118)
<223> OTHER INFORMATION: n can be any nucleotide

<400> SEQUENCE: 23
atgttggcta gggtttgtgg attcaagtgt tcttcttctc ctgctgwgtc tgcggctaga     60
ttgttctgta cgagatcgat tcgtgatact ctggccaagg caagcrgrga krnnnnnngt    120
tgcgaagcag gttttggagg agagagtttg aagctgcaaa gtgggtttca tgaaatcaaa    180
ggtttagagg atgcgattga tttgttcagt gacatgcttc gatctcgtcc tttaccttct    240
gtggttgatt tctgtaaatt gatgggtgtg gtggtgagra tgraacgccc ggatsttgtg    300
atttctctcy atmagaagat ggaaakgmrr crsattcsat gtgatryata cagcttcaat    360
attctgataa artgtttctg cagctgctct aagctsccct ttgctttgtc tacatttggt    420
aagmtcacca agcttggact ccaccctgat gttgttacct tcaccaccct kctccaygga    480
ttrtgygtgg aarataggk ttctgaagcy ttgratttkt ttcatcaaat gtttgaaacg    540
rcatgtaggc ccaatgtcgt aaccttcacc actttgatga acggtctttg ccgcgagggt    600
agaattgtcg aagccgtagc tctrcttgat cggatgatgg aagatggtct ccagcctacc    660
cagattactt atggaacaat cgtagatggg atgtgtaaga agggagatac tgtgtctgca    720
ctgaatctgc tgaggaagat ggaggaggtg agccacatca tacccaatgt tgtaatctat    780
agtgcaatca ttgatagcct ttgtaaagac ggacgtcata gcgatkcwca aaatctttc    840 actgaaatgc aagagaaagg aatctttccm gatttatttta cctacaacwg tatgatmrwy    900 ggktttttgta gctctggtag atggakcgac gcggagcagt tgttgcaaga aatgttagaa    960
aggaagatca gccctgatgt tgtaacttat aatgctttga tcaatgcatt tgtcaaggaa   1020
ggcaagttct ttgaggctga agaattatac gatgagatgc ttccwagggg tataatccct   1080
aatacaatca catatagttc aatgatcgat ggattttgca aacagaatcg tcttgatgct   1140
gctgagcaca tgttttatttt gatgsctacc aagggctgct ctccsracst awtcactttc   1200
aatactctca tagacggata tygtggggct aagaggatag atgatggaat ggaacttctc   1260
catgagatga ctgaarcagg attagttgct racacaaryta cttacaacac tcttattcac   1320
gggttytrtc wggtgggcga tcttamtgct gctctagacc ttytacawga gatgatytct   1380
agtggtktgt gccctratrt cgttacttgt rrcactttgc tggatggtct ctgcgataay   1440
```

```
gggaaactaa aagatgcatk ggaamtgttt aaggttatgc agaagagtaa gawggatctt    1500
gatgctagtc acccccttcaa tggtgtggaa cctgatgttc aaacttacaa tatattgatc    1560
agcggcttga tcaatgaagg gaagttttta gaggcygagg aattatacra ggagatgccc    1620
cacagggata tagtcccaga tactatyacc tatagctcaa tgatcgatgg aytatgcaag    1680
cagagccgcc trgatgaggc tacacaaatg tttgattcga tgggtagcaa gagcttctct    1740
ccaaacgtag tgacctttac tacactcatt ratggctact gtaargcagg aagggttgat    1800
gatgggctgg agcttttctg cgagatgggt mgaagaggga tagttgctaa yrcaattact    1860
tacatcactt tgattygtgg ttttcgyaaw gtgggtaata ttaatggggc tctagacatt    1920
ttccaggaga tgatttcaag tggtgtgtat cctgrtayca ttacyatccg cartatgctg    1980
actggtttat ggagtaaaga ggaactaaaa aggrcagtgg caatgcttga graactgcag    2040
atgagtrtgg rkywwymrtt kgrggrwkra tga                                2073
```

```
<210> SEQ ID NO 24
<211> LENGTH: 2064
<212> TYPE: DNA
<213> ORGANISM: Raphanus

<400> SEQUENCE: 24
```

```
atgttggcta gggtttgtgg attcaagtgt tcttcttctc ctgctgagtc tgcggctaga     60
ttgttctgta cgagatcgat tcgtgatact ctggccaagg caagcggaga gagttgcgaa    120
gcaggttttg gaggagagag tttgaagctg caaagtgggt ttcatgaaat caaaggttta    180
gaggatgcga ttgatttgtt cagtgacatg cttcgatctc gtcctttacc ttctgtggtt    240
gatttctgta aattgatggg tgtggtggtg agaatggaac gcccggatct tgtgatttct    300
ctctatcara agatggaaag gaaacagatt csatgtgatr tatacagctt yaatattctg    360
ataaaatgtt tctgcagytg ctctaagcty ccctttgctt tgtctacatt tggtaagmtc    420
accaagcttg gactccaccc tgatgttgyt accttcamca ccctgctcca yggattrtgy    480
stkgawraka gggtttctga agcyttgrat ttkttttcatc aaatgtttga aacgacatgt    540
aggccsaayr tcrtaacstt yaccackytg atgaacggtc tttgcyrcga gggtagartt    600
gtcgaagcyg tagctctgct tgatcggatg mtrgaagatg gtctccagcc trmccagatt    660
acttayggaa caatygtaga ygggatgtgt aagawgggag ayactgtgtc tgcaytgaat    720
ctkctgagga agatggagga gktgagccac atcawaccca atgtkgtaat ctatagtgcm    780
atcattgata gcctttgtaa agacggacgt catagcgatg cacaaaatct tttcactgaa    840
atgcaagaga aaggaatctt tcccgattta tttacctaca acagtatgat agttggtttt    900
tgtagctctg gtagatggag cgacgcggag cagttgttgc aagaaatgtt agaaggaag     960 atcagccctg atgttgtaac ttataatgct ttgatcaatg catttgtcaa ggaaggcaag   1020
ttctttgagg ctgaagaatt atacgatgag atgcttccaa ggggtataat ccctaataca   1080
atcacatata gttcaatgat cgatggatt tgcaaacaga atcgtcttga tgctgctgag   1140
cacatgtttt atttgatggc taccaagggc tgctctccca acctaatcac tttcaatact   1200
ctcatagacg gatattgtgg ggctaagagg atagatgatg aatggaact tctccatgag   1260 atgactgaaa caggattagt tgctgacaca actacttaca cactcttat tcacgggttc   1320 tatctggtgg gcgatcttaa tgctgctcta gacctttac aagagatgat ctctagtggt   1380
ttgtgccctg atatcgttac ttgtgacact tgctggatg gtctctgcga taatgggaaa   1440
ctaaaagatg cattggaaat gtttaaggtt atgcagaaga gtaagaagga tcttgatgct   1500
```

```
agtcacccct tcaatggtgt ggaacctgat gttcaaactt acaatatatt gatcagcggc    1560
ttgatcaatg aagggaagtt tttagaggcc gaggaattat acgaggagat gccccacagg    1620
ggtatagtcc cagatactat cacctatagc tcaatgatcg atggattatg caagcagagc    1680
cgcctagatg aggctacaca aatgtttgat tcgatgggta gcaagagctt ctctccaaac    1740
gtagtgacct ttactacact cattaatggc tactgtaagg caggaagggt tgatgatggg    1800
ctggagcttt tctgcgagat gggtcgaaga gggatagttg ctaacgcaat tacttacatc    1860
actttgattt gtggttttcg taaagtgggt aatattaatg gggctctaga cattttccag    1920
gagatgattt caagtggtgt gtatcctgat accattacca tccgcaatat gctgactggt    1980
ttatggagta agaggaact aaaaagggca gtggcaatgc ttgagaaact gcagatgagt    2040
atggatctat catttggggg atga                                          2064

<210> SEQ ID NO 25
<211> LENGTH: 2064
<212> TYPE: DNA
<213> ORGANISM: Raphanus

<400> SEQUENCE: 25
atgttggcta gggtttgtgg attcaagtgt tcttcttctc ctgctgagtc tgcggctaga     60
ttgttctgta cgagatcgat tcgtgatact ctggccaagg caagcggaga gagttgcgaa    120
gcaggttttg gaggagagag tttgaagctg caaagtgggt ttcatgaaat caaaggttta    180
gaggatgcga ttgatttgtt cagtgacatg cttcgatctc gtcctttacc ttctgtggtt    240
gatttctgta aattgatggg tgtggtggtg agaatggaac gcccggatct tgtgatttct    300
ctctatcaga agatggaaag gaaacagatt cgatgtgata tatacagctt caatattctg    360
ataaaatgtt tctgcagctg ctctaagctc ccctttgctt tgtctacatt tggtaagmtc    420
accaagcttg gactccaccc tgatgttgtt accttcacca ccctgctcca yggattrtgy    480
gtggaagata gggtttctga agcyttgrat ttktttcatc aaatgtttga acgacatgt    540 aggcccaatg tcgtaacctt caccactttg atgaacggtc tttgccgcga gggtagaatt    600
gtcgaagccg tagctctgct tgatcggatg atggaagatg gtctccagcc tacccagatt    660
acttatggaa caatcgtaga tgggatgtgt aagaagggag atactgtgtc tgcactgaat    720
ctgctgagga agatggagga ggtgagccac atcatacccca atgttgtaat ctatagtgca    780
atcattgata gcctttgtaa agacggacgt catagcgatg cacaaaatct tttcactgaa    840
atgcaagaga aggaatcttt cccgatttta tttacctaca cagtatgata gttggttttt    900
tgtagctctg gtagatggag cgacgcggag cagttgttgc aagaaatgtt agaaaggaag    960
atcagccctg atgttgtaac ttataatgct ttgatcaatg catttgtcaa ggaaggcaag    1020
ttctttgagg ctgaagaatt atacgatgag atgcttccaa ggggtataat ccctaataca    1080
atcacatata gttcaatgat cgatggattt tgcaaacaga atcgtcttga tgctgctgag    1140
cacatgtttt atttgatggc taccaagggc tgctctccca acctaatcac tttcaatact    1200
ctcatagacg atattgtggg gctaagagg atagatgatg gaatggaact tctccatgag    1260
atgactgaaa caggattagt tgctgacaca actacttaca cactcttat tcacgggttc    1320 tatctggtgg gcgatcttaa tgctgctcta gacctttac aagagatgat ctctagtggt    1380
ttgtgccctg atatcgttac ttgtgacact ttgctggatg gtctctgcga taatgggaaa    1440
ctaaaagatg cattggaaat gtttaaggtt atgcagaaga gtaagaagga tcttgatgct    1500
agtcacccct tcaatggtgt ggaacctgat gttcaaactt acaatatatt gatcagcggc    1560
```

-continued

```
ttgatcaatg aagggaagtt tttagaggcc gaggaattat acgaggagat gccccacagg    1620
ggtatagtcc cagatactat cacctatagc tcaatgatcg atggattatg caagcagagc    1680
cgcctagatg aggctacaca aatgtttgat tcgatgggta gcaagagctt ctctccaaac    1740
gtagtgacct ttactacact cattaatggc tactgtaagg caggaagggt tgatgatggg    1800
ctggagcttt tctgcgagat gggtcgaaga gggatagttg ctaacgcaat tacttacatc    1860
actttgattt gtggttttcg taaagtgggt aatattaatg gggctctaga catttttccag   1920 gagatgattt caagtggtgt gtatcctgat accattacca tccgcaatat gctgactggt    1980
ttatggagta aagaggaact aaaaagggca gtggcaatgc ttgagaaact gcagatgagt    2040
atggatctat catttggggg atga                                            2064
```

```
<210> SEQ ID NO 26
<211> LENGTH: 690
<212> TYPE: PRT
<213> ORGANISM: Raphanus
<220> FEATURE:
<221> NAME/KEY: Xaa
<222> LOCATION: (16)..(16)
<223> OTHER INFORMATION: Glu or Val
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: Xaa
<222> LOCATION: (36)..(36)
<223> OTHER INFORMATION: Arg or none
<220> FEATURE:
<221> NAME/KEY: misc_feature
<222> LOCATION: (36)..(37)
<223> OTHER INFORMATION: Xaa can be any naturally occurring amino acid
<220> FEATURE:
<221> NAME/KEY: Xaa
<222> LOCATION: (37)..(37)
<223> OTHER INFORMATION: Asp or none
<220> FEATURE:
<221> NAME/KEY: Xaa
<222> LOCATION: (95)..(95)
<223> OTHER INFORMATION: Glu or Lys
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: Xaa
<222> LOCATION: (99)..(99)
<223> OTHER INFORMATION: Leu or Val
<220> FEATURE:
<221> NAME/KEY: misc_feature
<222> LOCATION: (99)..(99)
<223> OTHER INFORMATION: Xaa can be any naturally occurring amino acid
<220> FEATURE:
<221> NAME/KEY: Xaa
<222> LOCATION: (104)..(104)
<223> OTHER INFORMATION: Tyr or His
<220> FEATURE:
<221> NAME/KEY: misc_feature
<222> LOCATION: (104)..(105)
<223> OTHER INFORMATION: Xaa can be any naturally occurring amino acid
<220> FEATURE:
<221> NAME/KEY: Xaa
<222> LOCATION: (105)..(105)
<223> OTHER INFORMATION: Gln or Lys
<220> FEATURE:
<221> NAME/KEY: Xaa
<222> LOCATION: (109)..(109)
<223> OTHER INFORMATION: Arg or Met
<220> FEATURE:
<221> NAME/KEY: misc_feature
<222> LOCATION: (109)..(111)
<223> OTHER INFORMATION: Xaa can be any naturally occurring amino acid
<220> FEATURE:
```

```
<221> NAME/KEY: Xaa
<222> LOCATION: (110)..(110)
<223> OTHER INFORMATION: Lys or Arg
<220> FEATURE:
<221> NAME/KEY: Xaa
<222> LOCATION: (111)..(111)
<223> OTHER INFORMATION: Gln or Arg
<220> FEATURE:
<221> NAME/KEY: Xaa
<222> LOCATION: (113)..(113)
<223> OTHER INFORMATION: Arg or Pro
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: Xaa
<222> LOCATION: (116)..(116)
<223> OTHER INFORMATION: Ile, Ala or Val
<220> FEATURE:
<221> NAME/KEY: misc_feature
<222> LOCATION: (116)..(116)
<223> OTHER INFORMATION: Xaa can be any naturally occurring amino acid
<220> FEATURE:
<221> NAME/KEY: Xaa
<222> LOCATION: (142)..(142)
<223> OTHER INFORMATION: Leu or Ile
<220> FEATURE:
<221> NAME/KEY: misc_feature
<222> LOCATION: (142)..(142)
<223> OTHER INFORMATION: Xaa can be any naturally occurring amino acid
<220> FEATURE:
<221> NAME/KEY: Xaa
<222> LOCATION: (152)..(152)
<223> OTHER INFORMATION: Val or Ala
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: Xaa
<222> LOCATION: (155)..(155)
<223> OTHER INFORMATION: Thr or Asn
<220> FEATURE:
<221> NAME/KEY: misc_feature
<222> LOCATION: (155)..(155)
<223> OTHER INFORMATION: Xaa can be any naturally occurring amino acid
<220> FEATURE:
<221> NAME/KEY: Xaa
<222> LOCATION: (163)..(163)
<223> OTHER INFORMATION: Val or Leu
<220> FEATURE:
<221> NAME/KEY: misc_feature
<222> LOCATION: (163)..(165)
<223> OTHER INFORMATION: Xaa can be any naturally occurring amino acid
<220> FEATURE:
<221> NAME/KEY: Xaa
<222> LOCATION: (164)..(164)
<223> OTHER INFORMATION: Glu or Asp
<220> FEATURE:
<221> NAME/KEY: Xaa
<222> LOCATION: (165)..(165)
<223> OTHER INFORMATION: Asp, Asn or Lys
<220> FEATURE:
<221> NAME/KEY: Xaa
<222> LOCATION: (167)..(167)
<223> OTHER INFORMATION: Val or Gly
<220> FEATURE:
<221> NAME/KEY: misc_feature
<222> LOCATION: (167)..(167)
<223> OTHER INFORMATION: Xaa can be any naturally occurring amino acid
<220> FEATURE:
<221> NAME/KEY: Xaa
<222> LOCATION: (172)..(172)
<223> OTHER INFORMATION: Asn or Asp
<220> FEATURE:
<221> NAME/KEY: misc_feature
<222> LOCATION: (172)..(173)
<223> OTHER INFORMATION: Xaa can be any naturally occurring amino acid
<220> FEATURE:
```

```
<221> NAME/KEY: Xaa
<222> LOCATION: (173)..(173)
<223> OTHER INFORMATION: Leu or Phe
<220> FEATURE:
<221> NAME/KEY: Xaa
<222> LOCATION: (186)..(186)
<223> OTHER INFORMATION: Val or Ile
<220> FEATURE:
<221> NAME/KEY: misc_feature
<222> LOCATION: (186)..(187)
<223> OTHER INFORMATION: Xaa can be any naturally occurring amino acid
<220> FEATURE:
<221> NAME/KEY: Xaa
<222> LOCATION: (187)..(187)
<223> OTHER INFORMATION: Val or Ile
<220> FEATURE:
<221> NAME/KEY: Xaa
<222> LOCATION: (198)..(198)
<223> OTHER INFORMATION: Arg or Tyr
<220> FEATURE:
<221> NAME/KEY: misc_feature
<222> LOCATION: (198)..(198)
<223> OTHER INFORMATION: Xaa can be any naturally occurring amino acid
<220> FEATURE:
<221> NAME/KEY: Xaa
<222> LOCATION: (202)..(202)
<223> OTHER INFORMATION: Ile or Val
<220> FEATURE:
<221> NAME/KEY: misc_feature
<222> LOCATION: (202)..(202)
<223> OTHER INFORMATION: Xaa can be any naturally occurring amino acid
<220> FEATURE:
<221> NAME/KEY: Xaa
<222> LOCATION: (213)..(213)
<223> OTHER INFORMATION: Met or Leu
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: Xaa
<222> LOCATION: (220)..(220)
<223> OTHER INFORMATION: Thr or Asp
<220> FEATURE:
<221> NAME/KEY: misc_feature
<222> LOCATION: (220)..(220)
<223> OTHER INFORMATION: Xaa can be any naturally occurring amino acid
<220> FEATURE:
<221> NAME/KEY: Xaa
<222> LOCATION: (234)..(234)
<223> OTHER INFORMATION: Lys or Met
<220> FEATURE:
<221> NAME/KEY: misc_feature
<222> LOCATION: (234)..(234)
<223> OTHER INFORMATION: Xaa can be any naturally occurring amino acid
<220> FEATURE:
<221> NAME/KEY: Xaa
<222> LOCATION: (250)..(250)
<223> OTHER INFORMATION: Val or Leu
<220> FEATURE:
<221> NAME/KEY: misc_feature
<222> LOCATION: (250)..(250)
<223> OTHER INFORMATION: Xaa can be any naturally occurring amino acid
<220> FEATURE:
<221> NAME/KEY: Xaa
<222> LOCATION: (254)..(254)
<223> OTHER INFORMATION: Ile or Lys
<220> FEATURE:
<221> NAME/KEY: misc_feature
<222> LOCATION: (254)..(254)
<223> OTHER INFORMATION: Xaa can be any naturally occurring amino acid
<220> FEATURE:
<221> NAME/KEY: Xaa
<222> LOCATION: (276)..(276)
<223> OTHER INFORMATION: Ala or Ser
<220> FEATURE:
<221> NAME/KEY: misc_feature
<222> LOCATION: (276)..(276)
<223> OTHER INFORMATION: Xaa can be any naturally occurring amino acid
<220> FEATURE:
```

```
<221> NAME/KEY: Xaa
<222> LOCATION: (297)..(297)
<223> OTHER INFORMATION: Ser or Cys
<220> FEATURE:
<221> NAME/KEY: misc_feature
<222> LOCATION: (297)..(297)
<223> OTHER INFORMATION: Xaa can be any naturally occurring amino acid
<220> FEATURE:
<221> NAME/KEY: Xaa
<222> LOCATION: (300)..(300)
<223> OTHER INFORMATION: Val or Asn
<220> FEATURE:
<221> NAME/KEY: misc_feature
<222> LOCATION: (300)..(300)
<223> OTHER INFORMATION: Xaa can be any naturally occurring amino acid
<220> FEATURE:
<221> NAME/KEY: Xaa
<222> LOCATION: (309)..(309)
<223> OTHER INFORMATION: Ser or Ile
<220> FEATURE:
<221> NAME/KEY: misc_feature
<222> LOCATION: (309)..(309)
<223> OTHER INFORMATION: Xaa can be any naturally occurring amino acid
<220> FEATURE:
<221> NAME/KEY: Xaa
<222> LOCATION: (389)..(389)
<223> OTHER INFORMATION: Ala or Pro
<220> FEATURE:
<221> NAME/KEY: misc_feature
<222> LOCATION: (389)..(389)
<223> OTHER INFORMATION: Xaa can be any naturally occurring amino acid
<220> FEATURE:
<221> NAME/KEY: Xaa
<222> LOCATION: (396)..(396)
<223> OTHER INFORMATION: Asn or Asp
<220> FEATURE:
<221> NAME/KEY: misc_feature
<222> LOCATION: (396)..(398)
<223> OTHER INFORMATION: Xaa can be any naturally occurring amino acid
<220> FEATURE:
<221> NAME/KEY: Xaa
<222> LOCATION: (397)..(397)
<223> OTHER INFORMATION: Leu or Val
<220> FEATURE:
<221> NAME/KEY: Xaa
<222> LOCATION: (398)..(398)
<223> OTHER INFORMATION: Ile or Phe
<220> FEATURE:
<221> NAME/KEY: Xaa
<222> LOCATION: (408)..(408)
<223> OTHER INFORMATION: Cys or Arg
<220> FEATURE:
<221> NAME/KEY: misc_feature
<222> LOCATION: (408)..(408)
<223> OTHER INFORMATION: Xaa can be any naturally occurring amino acid
<220> FEATURE:
<221> NAME/KEY: Xaa
<222> LOCATION: (426)..(426)
<223> OTHER INFORMATION: Thr or Ala
<220> FEATURE:
<221> NAME/KEY: misc_feature
<222> LOCATION: (426)..(426)
<223> OTHER INFORMATION: Xaa can be any naturally occurring amino acid
<220> FEATURE:
<221> NAME/KEY: Xaa
<222> LOCATION: (431)..(431)
<223> OTHER INFORMATION: Asp or Asn
<220> FEATURE:
<221> NAME/KEY: misc_feature
<222> LOCATION: (431)..(431)
<223> OTHER INFORMATION: Xaa can be any naturally occurring amino acid
<220> FEATURE:
<221> NAME/KEY: Xaa
<222> LOCATION: (433)..(433)
<223> OTHER INFORMATION: Thr or Val
<220> FEATURE:
<221> NAME/KEY: misc_feature
<222> LOCATION: (433)..(433)
<223> OTHER INFORMATION: Xaa can be any naturally occurring amino acid
<220> FEATURE:
```

```
<221> NAME/KEY: Xaa
<222> LOCATION: (443)..(443)
<223> OTHER INFORMATION: Tyr or Cys
<220> FEATURE:
<221> NAME/KEY: misc_feature
<222> LOCATION: (443)..(444)
<223> OTHER INFORMATION: Xaa can be any naturally occurring amino acid
<220> FEATURE:
<221> NAME/KEY: Xaa
<222> LOCATION: (444)..(444)
<223> OTHER INFORMATION: Leu or Gln
<220> FEATURE:
<221> NAME/KEY: Xaa
<222> LOCATION: (449)..(449)
<223> OTHER INFORMATION: Asn or Thr
<220> FEATURE:
<221> NAME/KEY: misc_feature
<222> LOCATION: (449)..(449)
<223> OTHER INFORMATION: Xaa can be any naturally occurring amino acid
<220> FEATURE:
<221> NAME/KEY: Xaa
<222> LOCATION: (456)..(456)
<223> OTHER INFORMATION: Gln or His
<220> FEATURE:
<221> NAME/KEY: misc_feature
<222> LOCATION: (456)..(456)
<223> OTHER INFORMATION: Xaa can be any naturally occurring amino acid
<220> FEATURE:
<221> NAME/KEY: Xaa
<222> LOCATION: (463)..(463)
<223> OTHER INFORMATION: Leu or Val
<220> FEATURE:
<221> NAME/KEY: misc_feature
<222> LOCATION: (463)..(463)
<223> OTHER INFORMATION: Xaa can be any naturally occurring amino acid
<220> FEATURE:
<221> NAME/KEY: Xaa
<222> LOCATION: (466)..(466)
<223> OTHER INFORMATION: Asp or Asn
<220> FEATURE:
<221> NAME/KEY: misc_feature
<222> LOCATION: (466)..(467)
<223> OTHER INFORMATION: Xaa can be any naturally occurring amino acid
<220> FEATURE:
<221> NAME/KEY: Xaa
<222> LOCATION: (467)..(467)
<223> OTHER INFORMATION: Ile or Val
<220> FEATURE:
<221> NAME/KEY: Xaa
<222> LOCATION: (471)..(471)
<223> OTHER INFORMATION: Asp or Ser
<220> FEATURE:
<221> NAME/KEY: misc_feature
<222> LOCATION: (471)..(471)
<223> OTHER INFORMATION: Xaa can be any naturally occurring amino acid
<220> FEATURE:
<221> NAME/KEY: Xaa
<222> LOCATION: (487)..(487)
<223> OTHER INFORMATION: Leu or Trp
<220> FEATURE:
<221> NAME/KEY: misc_feature
<222> LOCATION: (487)..(487)
<223> OTHER INFORMATION: Xaa can be any naturally occurring amino acid
<220> FEATURE:
<221> NAME/KEY: Xaa
<222> LOCATION: (489)..(489)
<223> OTHER INFORMATION: Met or Leu
<220> FEATURE:
<221> NAME/KEY: misc_feature
<222> LOCATION: (489)..(489)
<223> OTHER INFORMATION: Xaa can be any naturally occurring amino acid
<220> FEATURE:
<221> NAME/KEY: Xaa
<222> LOCATION: (498)..(498)
<223> OTHER INFORMATION: Lys or Met
<220> FEATURE:
<221> NAME/KEY: misc_feature
<222> LOCATION: (498)..(498)
<223> OTHER INFORMATION: Xaa can be any naturally occurring amino acid
<220> FEATURE:
```

```
<221> NAME/KEY: Xaa
<222> LOCATION: (537)..(537)
<223> OTHER INFORMATION: Glu or Lys
<220> FEATURE:
<221> NAME/KEY: misc_feature
<222> LOCATION: (537)..(537)
<223> OTHER INFORMATION: Xaa can be any naturally occurring amino acid
<220> FEATURE:
<221> NAME/KEY: Xaa
<222> LOCATION: (591)..(591)
<223> OTHER INFORMATION: Asn or Asp
<220> FEATURE:
<221> NAME/KEY: misc_feature
<222> LOCATION: (591)..(591)
<223> OTHER INFORMATION: Xaa can be any naturally occurring amino acid
<220> FEATURE:
<221> NAME/KEY: Xaa
<222> LOCATION: (618)..(618)
<223> OTHER INFORMATION: Ala or Thr
<220> FEATURE:
<221> NAME/KEY: misc_feature
<222> LOCATION: (618)..(618)
<223> OTHER INFORMATION: Xaa can be any naturally occurring amino acid
<220> FEATURE:
<221> NAME/KEY: Xaa
<222> LOCATION: (626)..(626)
<223> OTHER INFORMATION: Cys or Arg
<220> FEATURE:
<221> NAME/KEY: misc_feature
<222> LOCATION: (626)..(626)
<223> OTHER INFORMATION: Xaa can be any naturally occurring amino acid
<220> FEATURE:
<221> NAME/KEY: Xaa
<222> LOCATION: (630)..(630)
<223> OTHER INFORMATION: Lys or Asn
<220> FEATURE:
<221> NAME/KEY: misc_feature
<222> LOCATION: (630)..(630)
<223> OTHER INFORMATION: Xaa can be any naturally occurring amino acid
<220> FEATURE:
<221> NAME/KEY: Xaa
<222> LOCATION: (652)..(652)
<223> OTHER INFORMATION: Asp or Gly
<220> FEATURE:
<221> NAME/KEY: misc_feature
<222> LOCATION: (652)..(653)
<223> OTHER INFORMATION: Xaa can be any naturally occurring amino acid
<220> FEATURE:
<221> NAME/KEY: Xaa
<222> LOCATION: (653)..(653)
<223> OTHER INFORMATION: Thr or Ile
<220> FEATURE:
<221> NAME/KEY: Xaa
<222> LOCATION: (658)..(658)
<223> OTHER INFORMATION: Asn or Ser
<220> FEATURE:
<221> NAME/KEY: misc_feature
<222> LOCATION: (658)..(658)
<223> OTHER INFORMATION: Xaa can be any naturally occurring amino acid
<220> FEATURE:
<221> NAME/KEY: Xaa
<222> LOCATION: (672)..(672)
<223> OTHER INFORMATION: Ala or Thr
<220> FEATURE:
<221> NAME/KEY: misc_feature
<222> LOCATION: (672)..(672)
<223> OTHER INFORMATION: Xaa can be any naturally occurring amino acid
<220> FEATURE:
<221> NAME/KEY: Xaa
<222> LOCATION: (678)..(678)
<223> OTHER INFORMATION: Lys or Glu
<220> FEATURE:
<221> NAME/KEY: misc_feature
<222> LOCATION: (678)..(678)
<223> OTHER INFORMATION: Xaa can be any naturally occurring amino acid
<220> FEATURE:
<221> NAME/KEY: Xaa
<222> LOCATION: (683)..(683)
<223> OTHER INFORMATION: Met or Val
<220> FEATURE:
```

```
<221> NAME/KEY: misc_feature
<222> LOCATION: (683)..(690)
<223> OTHER INFORMATION: Xaa can be any naturally occurring amino acid
<220> FEATURE:
<221> NAME/KEY: Xaa
<222> LOCATION: (684)..(684)
<223> OTHER INFORMATION: Asp or Gly
<220> FEATURE:
<221> NAME/KEY: Xaa
<222> LOCATION: (685)..(685)
<223> OTHER INFORMATION: Leu or Tyr
<220> FEATURE:
<221> NAME/KEY: Xaa
<222> LOCATION: (686)..(686)
<223> OTHER INFORMATION: Ser or Gln
<220> FEATURE:
<221> NAME/KEY: Xaa
<222> LOCATION: (687)..(687)
<223> OTHER INFORMATION: Phe or Leu
<220> FEATURE:
<221> NAME/KEY: Xaa
<222> LOCATION: (688)..(688)
<223> OTHER INFORMATION: Gly or Glu
<220> FEATURE:
<221> NAME/KEY: Xaa
<222> LOCATION: (689)..(689)
<223> OTHER INFORMATION: Gly or Asp
<220> FEATURE:
<221> NAME/KEY: Xaa
<222> LOCATION: (690)..(690)
<223> OTHER INFORMATION: Glu or none

<400> SEQUENCE: 26

Met Leu Ala Arg Val Cys Gly Phe Lys Cys Ser Ser Pro Ala Xaa
1               5                   10                  15

Ser Ala Ala Arg Leu Phe Cys Thr Arg Ser Ile Arg Asp Thr Leu Ala
            20                  25                  30

Lys Ala Ser Xaa Xaa Gly Glu Ser Cys Glu Ala Gly Phe Gly Gly Glu
        35                  40                  45

Ser Leu Lys Leu Gln Ser Gly Phe His Glu Ile Lys Gly Leu Glu Asp
    50                  55                  60

Ala Ile Asp Leu Phe Ser Asp Met Leu Arg Ser Arg Pro Leu Pro Ser
65                  70                  75                  80

Val Val Asp Phe Cys Lys Leu Met Gly Val Val Arg Met Xaa Arg
                    85                  90                  95

Pro Asp Xaa Val Ile Ser Leu Xaa Xaa Lys Met Glu Xaa Xaa Xaa Ile
            100                 105                 110

Xaa Cys Asp Xaa Tyr Ser Phe Asn Ile Leu Ile Lys Cys Phe Cys Ser
        115                 120                 125

Cys Ser Lys Leu Pro Phe Ala Leu Ser Thr Phe Gly Lys Xaa Thr Lys
    130                 135                 140

Leu Gly Leu His Pro Asp Val Xaa Thr Phe Xaa Thr Leu Leu His Gly
145                 150                 155                 160

Leu Cys Xaa Xaa Xaa Arg Xaa Ser Glu Ala Leu Xaa Xaa Phe His Gln
            165                 170                 175

Met Phe Glu Thr Thr Cys Arg Pro Asn Xaa Xaa Thr Phe Thr Thr Leu
                180                 185                 190

Met Asn Gly Leu Cys Xaa Glu Gly Arg Xaa Val Glu Ala Val Ala Leu
            195                 200                 205

Leu Asp Arg Met Xaa Glu Asp Gly Leu Gln Pro Xaa Gln Ile Thr Tyr
        210                 215                 220

Gly Thr Ile Val Asp Gly Met Cys Lys Xaa Gly Asp Thr Val Ser Ala
225                 230                 235                 240

Leu Asn Leu Leu Arg Lys Met Glu Glu Xaa Ser His Ile Xaa Pro Asn
```

```
                245                 250                 255
Val Val Ile Tyr Ser Ala Ile Ile Asp Ser Leu Cys Lys Asp Gly Arg
                260                 265                 270

His Ser Asp Xaa Gln Asn Leu Phe Thr Glu Met Gln Glu Lys Gly Ile
            275                 280                 285

Phe Pro Asp Leu Phe Thr Tyr Asn Xaa Met Ile Xaa Gly Phe Cys Ser
        290                 295                 300

Ser Gly Arg Trp Xaa Asp Ala Glu Gln Leu Leu Gln Glu Met Leu Glu
305                 310                 315                 320

Arg Lys Ile Ser Pro Asp Val Val Thr Tyr Asn Ala Leu Ile Asn Ala
                325                 330                 335

Phe Val Lys Glu Gly Lys Phe Phe Glu Ala Glu Leu Tyr Asp Glu
                340                 345                 350

Met Leu Pro Arg Gly Ile Ile Pro Asn Thr Ile Thr Tyr Ser Ser Met
                355                 360                 365

Ile Asp Gly Phe Cys Lys Gln Asn Arg Leu Asp Ala Ala Glu His Met
370                 375                 380

Phe Tyr Leu Met Xaa Thr Lys Gly Cys Ser Pro Xaa Xaa Xaa Thr Phe
385                 390                 395                 400

Asn Thr Leu Ile Asp Gly Tyr Xaa Gly Ala Lys Arg Ile Asp Asp Gly
                405                 410                 415

Met Glu Leu Leu His Glu Met Thr Glu Xaa Gly Leu Val Ala Xaa Thr
                420                 425                 430

Xaa Thr Tyr Asn Thr Leu Ile His Gly Phe Xaa Xaa Val Gly Asp Leu
                435                 440                 445

Xaa Ala Ala Leu Asp Leu Leu Xaa Glu Met Ile Ser Ser Gly Xaa Cys
        450                 455                 460

Pro Xaa Xaa Val Thr Cys Xaa Thr Leu Leu Asp Gly Leu Cys Asp Asn
465                 470                 475                 480

Gly Lys Leu Lys Asp Ala Xaa Glu Xaa Phe Lys Val Met Gln Lys Ser
                485                 490                 495

Lys Xaa Asp Leu Asp Ala Ser His Pro Phe Asn Gly Val Glu Pro Asp
        500                 505                 510

Val Gln Thr Tyr Asn Ile Leu Ile Ser Gly Leu Ile Asn Glu Gly Lys
                515                 520                 525

Phe Leu Glu Ala Glu Glu Leu Tyr Xaa Glu Met Pro His Arg Gly Ile
        530                 535                 540

Val Pro Asp Thr Ile Thr Tyr Ser Ser Met Ile Asp Gly Leu Cys Lys
545                 550                 555                 560

Gln Ser Arg Leu Asp Glu Ala Thr Gln Met Phe Asp Ser Met Gly Ser
                565                 570                 575

Lys Ser Phe Ser Pro Asn Val Val Thr Phe Thr Leu Ile Xaa Gly
            580                 585                 590

Tyr Cys Lys Ala Gly Arg Val Asp Asp Gly Leu Glu Leu Phe Cys Glu
            595                 600                 605

Met Gly Arg Arg Gly Ile Val Ala Asn Xaa Ile Thr Tyr Ile Thr Leu
        610                 615                 620

Ile Xaa Gly Phe Arg Xaa Val Gly Asn Ile Asn Gly Ala Leu Asp Ile
625                 630                 635                 640

Phe Gln Glu Met Ile Ser Ser Gly Val Tyr Pro Xaa Xaa Ile Thr Ile
                645                 650                 655

Arg Xaa Met Leu Thr Gly Leu Trp Ser Lys Glu Glu Leu Lys Arg Xaa
        660                 665                 670
```

```
Val Ala Met Leu Glu Xaa Leu Gln Met Ser Xaa Xaa Xaa Xaa Xaa Xaa
        675                 680                 685

Xaa Xaa
    690

<210> SEQ ID NO 27
<211> LENGTH: 690
<212> TYPE: PRT
<213> ORGANISM: Raphanus
<220> FEATURE:
<221> NAME/KEY: Xaa
<222> LOCATION: (16)..(16)
<223> OTHER INFORMATION: Glu or Val
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: Xaa
<222> LOCATION: (36)..(36)
<223> OTHER INFORMATION: Arg or none
<220> FEATURE:
<221> NAME/KEY: misc_feature
<222> LOCATION: (36)..(37)
<223> OTHER INFORMATION: Xaa can be any naturally occurring amino acid
<220> FEATURE:
<221> NAME/KEY: Xaa
<222> LOCATION: (37)..(37)
<223> OTHER INFORMATION: Asp or none
<220> FEATURE:
<221> NAME/KEY: Xaa
<222> LOCATION: (95)..(95)
<223> OTHER INFORMATION: Glu or Lys
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: Xaa
<222> LOCATION: (99)..(99)
<223> OTHER INFORMATION: Leu or Val
<220> FEATURE:
<221> NAME/KEY: misc_feature
<222> LOCATION: (99)..(99)
<223> OTHER INFORMATION: Xaa can be any naturally occurring amino acid
<220> FEATURE:
<221> NAME/KEY: Xaa
<222> LOCATION: (104)..(104)
<223> OTHER INFORMATION: Tyr or His
<220> FEATURE:
<221> NAME/KEY: misc_feature
<222> LOCATION: (104)..(105)
<223> OTHER INFORMATION: Xaa can be any naturally occurring amino acid
<220> FEATURE:
<221> NAME/KEY: Xaa
<222> LOCATION: (105)..(105)
<223> OTHER INFORMATION: Gln or Lys
<220> FEATURE:
<221> NAME/KEY: Xaa
<222> LOCATION: (109)..(109)
<223> OTHER INFORMATION: Arg or Met
<220> FEATURE:
<221> NAME/KEY: misc_feature
<222> LOCATION: (109)..(111)
<223> OTHER INFORMATION: Xaa can be any naturally occurring amino acid
<220> FEATURE:
<221> NAME/KEY: Xaa
<222> LOCATION: (110)..(110)
<223> OTHER INFORMATION: Lys or Arg
<220> FEATURE:
<221> NAME/KEY: Xaa
<222> LOCATION: (111)..(111)
<223> OTHER INFORMATION: Gln or Arg
<220> FEATURE:
<221> NAME/KEY: Xaa
<222> LOCATION: (113)..(113)
<223> OTHER INFORMATION: Arg or Pro
<220> FEATURE:
```

```
<221> NAME/KEY: misc_feature
<222> LOCATION: (113)..(113)
<223> OTHER INFORMATION: Xaa can be any naturally occurring amino acid
<220> FEATURE:
<221> NAME/KEY: Xaa
<222> LOCATION: (116)..(116)
<223> OTHER INFORMATION: Ile or Ala
<220> FEATURE:
<221> NAME/KEY: misc_feature
<222> LOCATION: (116)..(116)
<223> OTHER INFORMATION: Xaa can be any naturally occurring amino acid
<220> FEATURE:
<221> NAME/KEY: Xaa
<222> LOCATION: (142)..(142)
<223> OTHER INFORMATION: Leu or Ile
<220> FEATURE:
<221> NAME/KEY: misc_feature
<222> LOCATION: (142)..(142)
<223> OTHER INFORMATION: Xaa can be any naturally occurring amino acid
<220> FEATURE:
<221> NAME/KEY: Xaa
<222> LOCATION: (165)..(165)
<223> OTHER INFORMATION: Asp or Asn
<220> FEATURE:
<221> NAME/KEY: misc_feature
<222> LOCATION: (165)..(165)
<223> OTHER INFORMATION: Xaa can be any naturally occurring amino acid
<220> FEATURE:
<221> NAME/KEY: Xaa
<222> LOCATION: (167)..(167)
<223> OTHER INFORMATION: Val or Gly
<220> FEATURE:
<221> NAME/KEY: misc_feature
<222> LOCATION: (167)..(167)
<223> OTHER INFORMATION: Xaa can be any naturally occurring amino acid
<220> FEATURE:
<221> NAME/KEY: Xaa
<222> LOCATION: (172)..(172)
<223> OTHER INFORMATION: Asn or Asp
<220> FEATURE:
<221> NAME/KEY: misc_feature
<222> LOCATION: (172)..(173)
<223> OTHER INFORMATION: Xaa can be any naturally occurring amino acid
<220> FEATURE:
<221> NAME/KEY: Xaa
<222> LOCATION: (173)..(173)
<223> OTHER INFORMATION: Leu or Phe
<220> FEATURE:
<221> NAME/KEY: Xaa
<222> LOCATION: (276)..(276)
<223> OTHER INFORMATION: Ala or Ser
<220> FEATURE:
<221> NAME/KEY: misc_feature
<222> LOCATION: (276)..(276)
<223> OTHER INFORMATION: Xaa can be any naturally occurring amino acid
<220> FEATURE:
<221> NAME/KEY: Xaa
<222> LOCATION: (297)..(297)
<223> OTHER INFORMATION: Ser or Cys
<220> FEATURE:
<221> NAME/KEY: misc_feature
<222> LOCATION: (297)..(297)
<223> OTHER INFORMATION: Xaa can be any naturally occurring amino acid
<220> FEATURE:
<221> NAME/KEY: Xaa
<222> LOCATION: (300)..(300)
<223> OTHER INFORMATION: Val or Asn
<220> FEATURE:
<221> NAME/KEY: misc_feature
<222> LOCATION: (300)..(300)
<223> OTHER INFORMATION: Xaa can be any naturally occurring amino acid
<220> FEATURE:
<221> NAME/KEY: Xaa
<222> LOCATION: (309)..(309)
<223> OTHER INFORMATION: Ser or Ile
<220> FEATURE:
<221> NAME/KEY: misc_feature
<222> LOCATION: (309)..(309)
<223> OTHER INFORMATION: Xaa can be any naturally occurring amino acid
<220> FEATURE:
```

```
<221> NAME/KEY: Xaa
<222> LOCATION: (389)..(389)
<223> OTHER INFORMATION: Ala or Pro
<220> FEATURE:
<221> NAME/KEY: misc_feature
<222> LOCATION: (389)..(389)
<223> OTHER INFORMATION: Xaa can be any naturally occurring amino acid
<220> FEATURE:
<221> NAME/KEY: Xaa
<222> LOCATION: (396)..(396)
<223> OTHER INFORMATION: Asn or Asp
<220> FEATURE:
<221> NAME/KEY: misc_feature
<222> LOCATION: (396)..(398)
<223> OTHER INFORMATION: Xaa can be any naturally occurring amino acid
<220> FEATURE:
<221> NAME/KEY: Xaa
<222> LOCATION: (397)..(397)
<223> OTHER INFORMATION: Leu or Val
<220> FEATURE:
<221> NAME/KEY: Xaa
<222> LOCATION: (398)..(398)
<223> OTHER INFORMATION: Ile or Phe
<220> FEATURE:
<221> NAME/KEY: Xaa
<222> LOCATION: (408)..(408)
<223> OTHER INFORMATION: Cys or Arg
<220> FEATURE:
<221> NAME/KEY: misc_feature
<222> LOCATION: (408)..(408)
<223> OTHER INFORMATION: Xaa can be any naturally occurring amino acid
<220> FEATURE:
<221> NAME/KEY: Xaa
<222> LOCATION: (426)..(426)
<223> OTHER INFORMATION: Thr or Ala
<220> FEATURE:
<221> NAME/KEY: misc_feature
<222> LOCATION: (426)..(426)
<223> OTHER INFORMATION: Xaa can be any naturally occurring amino acid
<220> FEATURE:
<221> NAME/KEY: Xaa
<222> LOCATION: (431)..(431)
<223> OTHER INFORMATION: Asp or Asn
<220> FEATURE:
<221> NAME/KEY: misc_feature
<222> LOCATION: (431)..(431)
<223> OTHER INFORMATION: Xaa can be any naturally occurring amino acid
<220> FEATURE:
<221> NAME/KEY: Xaa
<222> LOCATION: (433)..(433)
<223> OTHER INFORMATION: Thr or Val
<220> FEATURE:
<221> NAME/KEY: misc_feature
<222> LOCATION: (433)..(433)
<223> OTHER INFORMATION: Xaa can be any naturally occurring amino acid
<220> FEATURE:
<221> NAME/KEY: Xaa
<222> LOCATION: (443)..(443)
<223> OTHER INFORMATION: Tyr or Cys
<220> FEATURE:
<221> NAME/KEY: misc_feature
<222> LOCATION: (443)..(444)
<223> OTHER INFORMATION: Xaa can be any naturally occurring amino acid
<220> FEATURE:
<221> NAME/KEY: Xaa
<222> LOCATION: (444)..(444)
<223> OTHER INFORMATION: Leu or Gln
<220> FEATURE:
<221> NAME/KEY: Xaa
<222> LOCATION: (449)..(449)
<223> OTHER INFORMATION: Asn or Thr
<220> FEATURE:
<221> NAME/KEY: misc_feature
<222> LOCATION: (449)..(449)
<223> OTHER INFORMATION: Xaa can be any naturally occurring amino acid
<220> FEATURE:
<221> NAME/KEY: Xaa
<222> LOCATION: (456)..(456)
<223> OTHER INFORMATION: Gln or His
<220> FEATURE:
```

```
<221> NAME/KEY: misc_feature
<222> LOCATION: (456)..(456)
<223> OTHER INFORMATION: Xaa can be any naturally occurring amino acid
<220> FEATURE:
<221> NAME/KEY: Xaa
<222> LOCATION: (463)..(463)
<223> OTHER INFORMATION: Leu or Val
<220> FEATURE:
<221> NAME/KEY: misc_feature
<222> LOCATION: (463)..(463)
<223> OTHER INFORMATION: Xaa can be any naturally occurring amino acid
<220> FEATURE:
<221> NAME/KEY: Xaa
<222> LOCATION: (466)..(466)
<223> OTHER INFORMATION: Asp or Asn
<220> FEATURE:
<221> NAME/KEY: misc_feature
<222> LOCATION: (466)..(467)
<223> OTHER INFORMATION: Xaa can be any naturally occurring amino acid
<220> FEATURE:
<221> NAME/KEY: Xaa
<222> LOCATION: (467)..(467)
<223> OTHER INFORMATION: Ile or Val
<220> FEATURE:
<221> NAME/KEY: Xaa
<222> LOCATION: (471)..(471)
<223> OTHER INFORMATION: Asp or Ser
<220> FEATURE:
<221> NAME/KEY: misc_feature
<222> LOCATION: (471)..(471)
<223> OTHER INFORMATION: Xaa can be any naturally occurring amino acid
<220> FEATURE:
<221> NAME/KEY: Xaa
<222> LOCATION: (487)..(487)
<223> OTHER INFORMATION: Leu or Trp
<220> FEATURE:
<221> NAME/KEY: misc_feature
<222> LOCATION: (487)..(487)
<223> OTHER INFORMATION: Xaa can be any naturally occurring amino acid
<220> FEATURE:
<221> NAME/KEY: Xaa
<222> LOCATION: (489)..(489)
<223> OTHER INFORMATION: Met or Leu
<220> FEATURE:
<221> NAME/KEY: misc_feature
<222> LOCATION: (489)..(489)
<223> OTHER INFORMATION: Xaa can be any naturally occurring amino acid
<220> FEATURE:
<221> NAME/KEY: Xaa
<222> LOCATION: (498)..(498)
<223> OTHER INFORMATION: Lys or Met
<220> FEATURE:
<221> NAME/KEY: misc_feature
<222> LOCATION: (498)..(498)
<223> OTHER INFORMATION: Xaa can be any naturally occurring amino acid
<220> FEATURE:
<221> NAME/KEY: Xaa
<222> LOCATION: (537)..(537)
<223> OTHER INFORMATION: Glu or Lys
<220> FEATURE:
<221> NAME/KEY: misc_feature
<222> LOCATION: (537)..(537)
<223> OTHER INFORMATION: Xaa can be any naturally occurring amino acid
<220> FEATURE:
<221> NAME/KEY: Xaa
<222> LOCATION: (591)..(591)
<223> OTHER INFORMATION: Asn or Asp
<220> FEATURE:
<221> NAME/KEY: misc_feature
<222> LOCATION: (591)..(591)
<223> OTHER INFORMATION: Xaa can be any naturally occurring amino acid
<220> FEATURE:
<221> NAME/KEY: Xaa
<222> LOCATION: (618)..(618)
<223> OTHER INFORMATION: Ala or Thr
<220> FEATURE:
<221> NAME/KEY: misc_feature
<222> LOCATION: (618)..(618)
<223> OTHER INFORMATION: Xaa can be any naturally occurring amino acid
<220> FEATURE:
```

```
<221> NAME/KEY: Xaa
<222> LOCATION: (626)..(626)
<223> OTHER INFORMATION: Cys or Arg
<220> FEATURE:
<221> NAME/KEY: misc_feature
<222> LOCATION: (626)..(626)
<223> OTHER INFORMATION: Xaa can be any naturally occurring amino acid
<220> FEATURE:
<221> NAME/KEY: Xaa
<222> LOCATION: (630)..(630)
<223> OTHER INFORMATION: Lys or Asn
<220> FEATURE:
<221> NAME/KEY: misc_feature
<222> LOCATION: (630)..(630)
<223> OTHER INFORMATION: Xaa can be any naturally occurring amino acid
<220> FEATURE:
<221> NAME/KEY: Xaa
<222> LOCATION: (652)..(652)
<223> OTHER INFORMATION: Asp or Gly
<220> FEATURE:
<221> NAME/KEY: misc_feature
<222> LOCATION: (652)..(653)
<223> OTHER INFORMATION: Xaa can be any naturally occurring amino acid
<220> FEATURE:
<221> NAME/KEY: Xaa
<222> LOCATION: (653)..(653)
<223> OTHER INFORMATION: Thr or Ile
<220> FEATURE:
<221> NAME/KEY: Xaa
<222> LOCATION: (658)..(658)
<223> OTHER INFORMATION: Asn or Ser
<220> FEATURE:
<221> NAME/KEY: misc_feature
<222> LOCATION: (658)..(658)
<223> OTHER INFORMATION: Xaa can be any naturally occurring amino acid
<220> FEATURE:
<221> NAME/KEY: Xaa
<222> LOCATION: (672)..(672)
<223> OTHER INFORMATION: Ala or Thr
<220> FEATURE:
<221> NAME/KEY: misc_feature
<222> LOCATION: (672)..(672)
<223> OTHER INFORMATION: Xaa can be any naturally occurring amino acid
<220> FEATURE:
<221> NAME/KEY: Xaa
<222> LOCATION: (678)..(678)
<223> OTHER INFORMATION: Lys or Glu
<220> FEATURE:
<221> NAME/KEY: misc_feature
<222> LOCATION: (678)..(678)
<223> OTHER INFORMATION: Xaa can be any naturally occurring amino acid
<220> FEATURE:
<221> NAME/KEY: Xaa
<222> LOCATION: (683)..(683)
<223> OTHER INFORMATION: Met or Val
<220> FEATURE:
<221> NAME/KEY: misc_feature
<222> LOCATION: (683)..(690)
<223> OTHER INFORMATION: Xaa can be any naturally occurring amino acid
<220> FEATURE:
<221> NAME/KEY: Xaa
<222> LOCATION: (684)..(684)
<223> OTHER INFORMATION: Asp or Gly
<220> FEATURE:
<221> NAME/KEY: Xaa
<222> LOCATION: (685)..(685)
<223> OTHER INFORMATION: Leu or Tyr
<220> FEATURE:
<221> NAME/KEY: Xaa
<222> LOCATION: (686)..(686)
<223> OTHER INFORMATION: Ser or Gln
<220> FEATURE:
<221> NAME/KEY: Xaa
<222> LOCATION: (687)..(687)
<223> OTHER INFORMATION: Phe or Leu
<220> FEATURE:
<221> NAME/KEY: Xaa
<222> LOCATION: (688)..(688)
<223> OTHER INFORMATION: Gly or Glu
<220> FEATURE:
```

```
<221> NAME/KEY: Xaa
<222> LOCATION: (689)..(689)
<223> OTHER INFORMATION: Gly or Asp
<220> FEATURE:
<221> NAME/KEY: Xaa
<222> LOCATION: (690)..(690)
<223> OTHER INFORMATION: Glu or none

<400> SEQUENCE: 27
```

| | | | | | | | | | | | | | | |
|---|---|---|---|---|---|---|---|---|---|---|---|---|---|---|
|Met|Leu|Ala|Arg|Val|Cys|Gly|Phe|Lys|Cys|Ser|Ser|Pro|Ala|Xaa|
|1| | | |5| | | | |10| | | | |15|

Ser Ala Ala Arg Leu Phe Cys Thr Arg Ser Ile Arg Asp Thr Leu Ala
          20                  25                  30

Lys Ala Ser Xaa Xaa Gly Glu Ser Cys Glu Ala Gly Phe Gly Gly Glu
              35                  40                  45

Ser Leu Lys Leu Gln Ser Gly Phe His Glu Ile Lys Gly Leu Glu Asp
 50                  55                  60

Ala Ile Asp Leu Phe Ser Asp Met Leu Arg Ser Arg Pro Leu Pro Ser
65                  70                  75                  80

Val Val Asp Phe Cys Lys Leu Met Gly Val Val Arg Met Xaa Arg
                  85                  90                  95

Pro Asp Xaa Val Ile Ser Leu Xaa Xaa Lys Met Glu Xaa Xaa Ile
          100                 105                 110

Xaa Cys Asp Xaa Tyr Ser Phe Asn Ile Leu Ile Lys Cys Phe Cys Ser
      115                 120                 125

Cys Ser Lys Leu Pro Phe Ala Leu Ser Thr Phe Gly Lys Xaa Thr Lys
 130                 135                 140

Leu Gly Leu His Pro Asp Val Val Thr Phe Thr Thr Leu Leu His Gly
145                 150                 155                 160

Leu Cys Val Glu Xaa Arg Xaa Ser Glu Ala Leu Xaa Xaa Phe His Gln
                  165                 170                 175

Met Phe Glu Thr Thr Cys Arg Pro Asn Val Val Thr Phe Thr Thr Leu
              180                 185                 190

Met Asn Gly Leu Cys Arg Glu Gly Arg Ile Val Glu Ala Val Ala Leu
              195                 200                 205

Leu Asp Arg Met Met Glu Asp Gly Leu Gln Pro Thr Gln Ile Thr Tyr
 210                 215                 220

Gly Thr Ile Val Asp Gly Met Cys Lys Lys Gly Asp Thr Val Ser Ala
225                 230                 235                 240

Leu Asn Leu Leu Arg Lys Met Glu Glu Val Ser His Ile Ile Pro Asn
              245                 250                 255

Val Val Ile Tyr Ser Ala Ile Ile Asp Ser Leu Cys Lys Asp Gly Arg
              260                 265                 270

His Ser Asp Xaa Gln Asn Leu Phe Thr Glu Met Gln Glu Lys Gly Ile
              275                 280                 285

Phe Pro Asp Leu Phe Thr Tyr Asn Xaa Met Ile Xaa Gly Phe Cys Ser
 290                 295                 300

Ser Gly Arg Trp Xaa Asp Ala Glu Gln Leu Leu Gln Glu Met Leu Glu
305                 310                 315                 320

Arg Lys Ile Ser Pro Asp Val Val Thr Tyr Asn Ala Leu Ile Asn Ala
              325                 330                 335

Phe Val Lys Glu Gly Lys Phe Phe Glu Ala Glu Leu Tyr Asp Glu
              340                 345                 350

Met Leu Pro Arg Gly Ile Ile Pro Asn Thr Ile Thr Tyr Ser Ser Met
 355                 360                 365

Ile Asp Gly Phe Cys Lys Gln Asn Arg Leu Asp Ala Ala Glu His Met

```
                370                 375                 380
Phe Tyr Leu Met Xaa Thr Lys Gly Cys Ser Pro Xaa Xaa Xaa Thr Phe
385                 390                 395                 400

Asn Thr Leu Ile Asp Gly Tyr Xaa Gly Ala Lys Arg Ile Asp Asp Gly
                405                 410                 415

Met Glu Leu Leu His Glu Met Thr Glu Xaa Gly Leu Val Ala Xaa Thr
                420                 425                 430

Xaa Thr Tyr Asn Thr Leu Ile His Gly Phe Xaa Xaa Val Gly Asp Leu
                435                 440                 445

Xaa Ala Ala Leu Asp Leu Leu Xaa Glu Met Ile Ser Ser Gly Xaa Cys
450                 455                 460

Pro Xaa Xaa Val Thr Cys Xaa Thr Leu Leu Asp Gly Leu Cys Asp Asn
465                 470                 475                 480

Gly Lys Leu Lys Asp Ala Xaa Glu Xaa Phe Lys Val Met Gln Lys Ser
                485                 490                 495

Lys Xaa Asp Leu Asp Ala Ser His Pro Phe Asn Gly Val Glu Pro Asp
                500                 505                 510

Val Gln Thr Tyr Asn Ile Leu Ile Ser Gly Leu Ile Asn Glu Gly Lys
                515                 520                 525

Phe Leu Glu Ala Glu Glu Leu Tyr Xaa Glu Met Pro His Arg Gly Ile
530                 535                 540

Val Pro Asp Thr Ile Thr Tyr Ser Ser Met Ile Asp Gly Leu Cys Lys
545                 550                 555                 560

Gln Ser Arg Leu Asp Glu Ala Thr Gln Met Phe Asp Ser Met Gly Ser
                565                 570                 575

Lys Ser Phe Ser Pro Asn Val Val Thr Phe Thr Thr Leu Ile Xaa Gly
                580                 585                 590

Tyr Cys Lys Ala Gly Arg Val Asp Asp Gly Leu Glu Leu Phe Cys Glu
                595                 600                 605

Met Gly Arg Arg Gly Ile Val Ala Asn Xaa Ile Thr Tyr Ile Thr Leu
                610                 615                 620

Ile Xaa Gly Phe Arg Xaa Val Gly Asn Ile Asn Gly Ala Leu Asp Ile
625                 630                 635                 640

Phe Gln Glu Met Ile Ser Ser Gly Val Tyr Pro Xaa Xaa Ile Thr Ile
                645                 650                 655

Arg Xaa Met Leu Thr Gly Leu Trp Ser Lys Glu Glu Leu Lys Arg Xaa
                660                 665                 670

Val Ala Met Leu Glu Xaa Leu Gln Met Ser Xaa Xaa Xaa Xaa Xaa
                675                 680                 685

Xaa Xaa
    690

<210> SEQ ID NO 28
<211> LENGTH: 687
<212> TYPE: PRT
<213> ORGANISM: Raphanus
<220> FEATURE:
<221> NAME/KEY: X
<222> LOCATION: (111)..(111)
<223> OTHER INFORMATION: Arg or Pro
<220> FEATURE:
<221> NAME/KEY: misc_feature
<222> LOCATION: (111)..(111)
<223> OTHER INFORMATION: Xaa can be any naturally occurring amino acid
<220> FEATURE:
<221> NAME/KEY: X
<222> LOCATION: (114)..(114)
<223> OTHER INFORMATION: Ile or Val
<220> FEATURE:
```

```
<221> NAME/KEY: misc_feature
<222> LOCATION: (114)..(114)
<223> OTHER INFORMATION: Xaa can be any naturally occurring amino acid
<220> FEATURE:
<221> NAME/KEY: X
<222> LOCATION: (140)..(140)
<223> OTHER INFORMATION: Leu or Ile
<220> FEATURE:
<221> NAME/KEY: misc_feature
<222> LOCATION: (140)..(140)
<223> OTHER INFORMATION: Xaa can be any naturally occurring amino acid
<220> FEATURE:
<221> NAME/KEY: X
<222> LOCATION: (150)..(150)
<223> OTHER INFORMATION: Val or Ala
<220> FEATURE:
<221> NAME/KEY: misc_feature
<222> LOCATION: (150)..(150)
<223> OTHER INFORMATION: Xaa can be any naturally occurring amino acid
<220> FEATURE:
<221> NAME/KEY: X
<222> LOCATION: (153)..(153)
<223> OTHER INFORMATION: Thr or Asn
<220> FEATURE:
<221> NAME/KEY: misc_feature
<222> LOCATION: (153)..(153)
<223> OTHER INFORMATION: Xaa can be any naturally occurring amino acid
<220> FEATURE:
<221> NAME/KEY: X
<222> LOCATION: (161)..(161)
<223> OTHER INFORMATION: Val or Leu
<220> FEATURE:
<221> NAME/KEY: misc_feature
<222> LOCATION: (161)..(163)
<223> OTHER INFORMATION: Xaa can be any naturally occurring amino acid
<220> FEATURE:
<221> NAME/KEY: X
<222> LOCATION: (162)..(162)
<223> OTHER INFORMATION: Glu or Asp
<220> FEATURE:
<221> NAME/KEY: X
<222> LOCATION: (163)..(163)
<223> OTHER INFORMATION: Asp or Lys
<220> FEATURE:
<221> NAME/KEY: X
<222> LOCATION: (170)..(170)
<223> OTHER INFORMATION: Asn or Asp
<220> FEATURE:
<221> NAME/KEY: misc_feature
<222> LOCATION: (170)..(171)
<223> OTHER INFORMATION: Xaa can be any naturally occurring amino acid
<220> FEATURE:
<221> NAME/KEY: X
<222> LOCATION: (171)..(171)
<223> OTHER INFORMATION: Leu or Phe
<220> FEATURE:
<221> NAME/KEY: X
<222> LOCATION: (184)..(184)
<223> OTHER INFORMATION: Val or Ile
<220> FEATURE:
<221> NAME/KEY: misc_feature
<222> LOCATION: (184)..(185)
<223> OTHER INFORMATION: Xaa can be any naturally occurring amino acid
<220> FEATURE:
<221> NAME/KEY: X
<222> LOCATION: (185)..(185)
<223> OTHER INFORMATION: Val or Ile
<220> FEATURE:
<221> NAME/KEY: X
<222> LOCATION: (196)..(196)
<223> OTHER INFORMATION: Arg or Tyr
<220> FEATURE:
<221> NAME/KEY: misc_feature
<222> LOCATION: (196)..(196)
<223> OTHER INFORMATION: Xaa can be any naturally occurring amino acid
<220> FEATURE:
<221> NAME/KEY: X
<222> LOCATION: (200)..(200)
<223> OTHER INFORMATION: Ile or Val
<220> FEATURE:
```

```
<221> NAME/KEY: misc_feature
<222> LOCATION: (200)..(200)
<223> OTHER INFORMATION: Xaa can be any naturally occurring amino acid
<220> FEATURE:
<221> NAME/KEY: X
<222> LOCATION: (211)..(211)
<223> OTHER INFORMATION: Met or Leu
<220> FEATURE:
<221> NAME/KEY: misc_feature
<222> LOCATION: (211)..(211)
<223> OTHER INFORMATION: Xaa can be any naturally occurring amino acid
<220> FEATURE:
<221> NAME/KEY: X
<222> LOCATION: (218)..(218)
<223> OTHER INFORMATION: Thr or Asp
<220> FEATURE:
<221> NAME/KEY: misc_feature
<222> LOCATION: (218)..(218)
<223> OTHER INFORMATION: Xaa can be any naturally occurring amino acid
<220> FEATURE:
<221> NAME/KEY: X
<222> LOCATION: (232)..(232)
<223> OTHER INFORMATION: Lys or Met
<220> FEATURE:
<221> NAME/KEY: misc_feature
<222> LOCATION: (232)..(232)
<223> OTHER INFORMATION: Xaa can be any naturally occurring amino acid
<220> FEATURE:
<221> NAME/KEY: X
<222> LOCATION: (248)..(248)
<223> OTHER INFORMATION: Val or Leu
<220> FEATURE:
<221> NAME/KEY: misc_feature
<222> LOCATION: (248)..(248)
<223> OTHER INFORMATION: Xaa can be any naturally occurring amino acid
<220> FEATURE:
<221> NAME/KEY: X
<222> LOCATION: (252)..(252)
<223> OTHER INFORMATION: Ile or Lys
<220> FEATURE:
<221> NAME/KEY: misc_feature
<222> LOCATION: (252)..(252)
<223> OTHER INFORMATION: Xaa can be any naturally occurring amino acid

<400> SEQUENCE: 28

Met Leu Ala Arg Val Cys Gly Phe Lys Cys Ser Ser Ser Pro Ala Glu
1               5                   10                  15

Ser Ala Ala Arg Leu Phe Cys Thr Arg Ser Ile Arg Asp Thr Leu Ala
                20                  25                  30

Lys Ala Ser Gly Glu Ser Cys Glu Ala Gly Phe Gly Gly Glu Ser Leu
            35                  40                  45

Lys Leu Gln Ser Gly Phe His Glu Ile Lys Gly Leu Glu Asp Ala Ile
        50                  55                  60

Asp Leu Phe Ser Asp Met Leu Arg Ser Arg Pro Leu Pro Ser Val Val
65                  70                  75                  80

Asp Phe Cys Lys Leu Met Gly Val Val Arg Met Glu Arg Pro Asp
                85                  90                  95

Leu Val Ile Ser Leu Tyr Gln Lys Met Glu Arg Lys Gln Ile Xaa Cys
                100                 105                 110

Asp Xaa Tyr Ser Phe Asn Ile Leu Ile Lys Cys Phe Cys Ser Cys Ser
            115                 120                 125

Lys Leu Pro Phe Ala Leu Ser Thr Phe Gly Lys Xaa Thr Lys Leu Gly
        130                 135                 140

Leu His Pro Asp Val Xaa Thr Phe Xaa Thr Leu Leu His Gly Leu Cys
145                 150                 155                 160

Xaa Xaa Xaa Arg Val Ser Glu Ala Leu Xaa Xaa Phe His Gln Met Phe
                165                 170                 175

Glu Thr Thr Cys Arg Pro Asn Xaa Xaa Thr Phe Thr Thr Leu Met Asn
```

```
                180                 185                 190
Gly Leu Cys Xaa Glu Gly Arg Xaa Val Glu Ala Val Ala Leu Leu Asp
            195                 200                 205
Arg Met Xaa Glu Asp Gly Leu Gln Pro Xaa Gln Ile Thr Tyr Gly Thr
        210                 215                 220
Ile Val Asp Gly Met Cys Lys Xaa Gly Asp Thr Val Ser Ala Leu Asn
225                 230                 235                 240
Leu Leu Arg Lys Met Glu Glu Xaa Ser His Ile Xaa Pro Asn Val Val
                245                 250                 255
Ile Tyr Ser Ala Ile Ile Asp Ser Leu Cys Lys Asp Gly Arg His Ser
            260                 265                 270
Asp Ala Gln Asn Leu Phe Thr Glu Met Gln Glu Lys Gly Ile Phe Pro
        275                 280                 285
Asp Leu Phe Thr Tyr Asn Ser Met Ile Val Gly Phe Cys Ser Ser Gly
        290                 295                 300
Arg Trp Ser Asp Ala Glu Gln Leu Leu Gln Glu Met Leu Glu Arg Lys
305                 310                 315                 320
Ile Ser Pro Asp Val Val Thr Tyr Asn Ala Leu Ile Asn Ala Phe Val
                325                 330                 335
Lys Glu Gly Lys Phe Phe Glu Ala Glu Leu Tyr Asp Glu Met Leu
            340                 345                 350
Pro Arg Gly Ile Ile Pro Asn Thr Ile Thr Tyr Ser Ser Met Ile Asp
            355                 360                 365
Gly Phe Cys Lys Gln Asn Arg Leu Asp Ala Ala Glu His Met Phe Tyr
        370                 375                 380
Leu Met Ala Thr Lys Gly Cys Ser Pro Asn Leu Ile Thr Phe Asn Thr
385                 390                 395                 400
Leu Ile Asp Gly Tyr Cys Gly Ala Lys Arg Ile Asp Asp Gly Met Glu
                405                 410                 415
Leu Leu His Glu Met Thr Glu Thr Gly Leu Val Ala Asp Thr Thr Thr
                420                 425                 430
Tyr Asn Thr Leu Ile His Gly Phe Tyr Leu Val Gly Asp Leu Asn Ala
            435                 440                 445
Ala Leu Asp Leu Leu Gln Glu Met Ile Ser Ser Gly Leu Cys Pro Asp
        450                 455                 460
Ile Val Thr Cys Asp Thr Leu Leu Asp Gly Leu Cys Asp Asn Gly Lys
465                 470                 475                 480
Leu Lys Asp Ala Leu Glu Met Phe Lys Val Met Gln Lys Ser Lys Lys
                485                 490                 495
Asp Leu Asp Ala Ser His Pro Phe Asn Gly Val Glu Pro Asp Val Gln
            500                 505                 510
Thr Tyr Asn Ile Leu Ile Ser Gly Leu Ile Asn Glu Gly Lys Phe Leu
        515                 520                 525
Glu Ala Glu Glu Leu Tyr Glu Glu Met Pro His Arg Gly Ile Val Pro
        530                 535                 540
Asp Thr Ile Thr Tyr Ser Ser Met Ile Asp Gly Leu Cys Lys Gln Ser
545                 550                 555                 560
Arg Leu Asp Glu Ala Thr Gln Met Phe Asp Ser Met Gly Ser Lys Ser
                565                 570                 575
Phe Ser Pro Asn Val Val Thr Phe Thr Thr Leu Ile Asn Gly Tyr Cys
            580                 585                 590
Lys Ala Gly Arg Val Asp Asp Gly Leu Glu Leu Phe Cys Glu Met Gly
        595                 600                 605
```

```
Arg Arg Gly Ile Val Ala Asn Ala Ile Thr Tyr Ile Thr Leu Ile Cys
        610                 615                 620

Gly Phe Arg Lys Val Gly Asn Ile Asn Gly Ala Leu Asp Ile Phe Gln
625                 630                 635                 640

Glu Met Ile Ser Ser Gly Val Tyr Pro Asp Thr Ile Thr Ile Arg Asn
                645                 650                 655

Met Leu Thr Gly Leu Trp Ser Lys Glu Leu Lys Arg Ala Val Ala
            660                 665                 670

Met Leu Glu Lys Leu Gln Met Ser Met Asp Leu Ser Phe Gly Gly
            675                 680                 685

<210> SEQ ID NO 29
<211> LENGTH: 687
<212> TYPE: PRT
<213> ORGANISM: Raphanus
<220> FEATURE:
<221> NAME/KEY: X
<222> LOCATION: (140)..(140)
<223> OTHER INFORMATION: Leu or Ile
<220> FEATURE:
<221> NAME/KEY: misc_feature
<222> LOCATION: (140)..(140)
<223> OTHER INFORMATION: Xaa can be any naturally occurring amino acid
<220> FEATURE:
<221> NAME/KEY: X
<222> LOCATION: (170)..(170)
<223> OTHER INFORMATION: Asn or Asp
<220> FEATURE:
<221> NAME/KEY: misc_feature
<222> LOCATION: (170)..(171)
<223> OTHER INFORMATION: Xaa can be any naturally occurring amino acid
<220> FEATURE:
<221> NAME/KEY: X
<222> LOCATION: (171)..(171)
<223> OTHER INFORMATION: Leu or Phe

<400> SEQUENCE: 29

Met Leu Ala Arg Val Cys Gly Phe Lys Cys Ser Ser Ser Pro Ala Glu
1               5                   10                  15

Ser Ala Ala Arg Leu Phe Cys Thr Arg Ser Ile Arg Asp Thr Leu Ala
            20                  25                  30

Lys Ala Ser Gly Glu Ser Cys Glu Ala Gly Phe Gly Gly Glu Ser Leu
        35                  40                  45

Lys Leu Gln Ser Gly Phe His Glu Ile Lys Gly Leu Glu Asp Ala Ile
50                  55                  60

Asp Leu Phe Ser Asp Met Leu Arg Ser Arg Pro Leu Pro Ser Val Val
65                  70                  75                  80

Asp Phe Cys Lys Leu Met Gly Val Val Arg Met Glu Arg Pro Asp
            85                  90                  95

Leu Val Ile Ser Leu Tyr Gln Lys Met Glu Arg Lys Gln Ile Arg Cys
                100                 105                 110

Asp Ile Tyr Ser Phe Asn Ile Leu Ile Lys Cys Phe Cys Ser Cys Ser
            115                 120                 125

Lys Leu Pro Phe Ala Leu Ser Thr Phe Gly Lys Xaa Thr Lys Leu Gly
        130                 135                 140

Leu His Pro Asp Val Val Thr Phe Thr Thr Leu Leu His Gly Leu Cys
145                 150                 155                 160

Val Glu Asp Arg Val Ser Glu Ala Leu Xaa Xaa Phe His Gln Met Phe
                165                 170                 175

Glu Thr Thr Cys Arg Pro Asn Val Val Thr Phe Thr Thr Leu Met Asn
            180                 185                 190

Gly Leu Cys Arg Glu Gly Arg Ile Val Glu Ala Val Ala Leu Leu Asp
```

```
                195                 200                 205
Arg Met Met Glu Asp Gly Leu Gln Pro Thr Gln Ile Thr Tyr Gly Thr
210                 215                 220

Ile Val Asp Gly Met Cys Lys Lys Gly Asp Thr Val Ser Ala Leu Asn
225                 230                 235                 240

Leu Leu Arg Lys Met Glu Val Ser His Ile Pro Asn Val Val
                245                 250                 255

Ile Tyr Ser Ala Ile Ile Asp Ser Leu Cys Lys Asp Gly Arg His Ser
            260                 265                 270

Asp Ala Gln Asn Leu Phe Thr Glu Met Gln Glu Lys Gly Ile Phe Pro
        275                 280                 285

Asp Leu Phe Thr Tyr Asn Ser Met Ile Val Gly Phe Cys Ser Ser Gly
        290                 295                 300

Arg Trp Ser Asp Ala Glu Gln Leu Leu Gln Glu Met Leu Glu Arg Lys
305                 310                 315                 320

Ile Ser Pro Asp Val Val Thr Tyr Asn Ala Leu Ile Asn Ala Phe Val
                325                 330                 335

Lys Glu Gly Lys Phe Phe Glu Ala Glu Glu Leu Tyr Asp Glu Met Leu
            340                 345                 350

Pro Arg Gly Ile Ile Pro Asn Thr Ile Thr Tyr Ser Ser Met Ile Asp
        355                 360                 365

Gly Phe Cys Lys Gln Asn Arg Leu Asp Ala Ala Glu His Met Phe Tyr
        370                 375                 380

Leu Met Ala Thr Lys Gly Cys Ser Pro Asn Leu Ile Thr Phe Asn Thr
385                 390                 395                 400

Leu Ile Asp Gly Tyr Cys Gly Ala Lys Arg Ile Asp Asp Gly Met Glu
                405                 410                 415

Leu Leu His Glu Met Thr Glu Thr Gly Leu Val Ala Asp Thr Thr Thr
            420                 425                 430

Tyr Asn Thr Leu Ile His Gly Phe Tyr Leu Val Gly Asp Leu Asn Ala
        435                 440                 445

Ala Leu Asp Leu Leu Gln Glu Met Ile Ser Ser Gly Leu Cys Pro Asp
450                 455                 460

Ile Val Thr Cys Asp Thr Leu Leu Asp Gly Leu Cys Asp Asn Gly Lys
465                 470                 475                 480

Leu Lys Asp Ala Leu Glu Met Phe Lys Val Met Gln Lys Ser Lys Lys
                485                 490                 495

Asp Leu Asp Ala Ser His Pro Phe Asn Gly Val Glu Pro Asp Val Gln
            500                 505                 510

Thr Tyr Asn Ile Leu Ile Ser Gly Leu Ile Asn Glu Gly Lys Phe Leu
        515                 520                 525

Glu Ala Glu Glu Leu Tyr Glu Met Pro His Arg Gly Ile Val Pro
        530                 535                 540

Asp Thr Ile Thr Tyr Ser Ser Met Ile Asp Gly Leu Cys Lys Gln Ser
545                 550                 555                 560

Arg Leu Asp Glu Ala Thr Gln Met Phe Asp Ser Met Gly Ser Lys Ser
                565                 570                 575

Phe Ser Pro Asn Val Val Thr Phe Thr Leu Ile Asn Gly Tyr Cys
            580                 585                 590

Lys Ala Gly Arg Val Asp Asp Gly Leu Glu Leu Phe Cys Glu Met Gly
        595                 600                 605

Arg Arg Gly Ile Val Ala Asn Ala Ile Thr Tyr Ile Thr Leu Ile Cys
610                 615                 620
```

-continued

```
Gly Phe Arg Lys Val Gly Asn Ile Asn Gly Ala Leu Asp Ile Phe Gln
625                 630                 635                 640

Glu Met Ile Ser Ser Gly Val Tyr Pro Asp Thr Ile Thr Ile Arg Asn
            645                 650                 655

Met Leu Thr Gly Leu Trp Ser Lys Glu Glu Leu Lys Arg Ala Val Ala
        660                 665                 670

Met Leu Glu Lys Leu Gln Met Ser Met Asp Leu Ser Phe Gly Gly
    675                 680                 685

<210> SEQ ID NO 30
<211> LENGTH: 33
<212> TYPE: DNA
<213> ORGANISM: Artificial
<220> FEATURE:
<223> OTHER INFORMATION: Probe

<400> SEQUENCE: 30
acataaaaat cactagatac ttgacatgga ggc                               33

<210> SEQ ID NO 31
<211> LENGTH: 25
<212> TYPE: DNA
<213> ORGANISM: Artificial
<220> FEATURE:
<223> OTHER INFORMATION: Probe

<400> SEQUENCE: 31
aagaggagga agatggcatc acagc                                        25

<210> SEQ ID NO 32
<211> LENGTH: 26
<212> TYPE: DNA
<213> ORGANISM: Artificial
<220> FEATURE:
<223> OTHER INFORMATION: Probe

<400> SEQUENCE: 32
tggagtaaag aggaactaaa aagggc                                       26

<210> SEQ ID NO 33
<211> LENGTH: 23
<212> TYPE: DNA
<213> ORGANISM: Artificial
<220> FEATURE:
<223> OTHER INFORMATION: Probe

<400> SEQUENCE: 33
cagacaatag acgcataaaa ggc                                          23

<210> SEQ ID NO 34
<211> LENGTH: 23
<212> TYPE: DNA
<213> ORGANISM: Artificial
<220> FEATURE:
<223> OTHER INFORMATION: Probe

<400> SEQUENCE: 34
gattcctttc tcttgcattt cag                                          23

<210> SEQ ID NO 35
<211> LENGTH: 23
<212> TYPE: DNA
<213> ORGANISM: Artificial
<220> FEATURE:
<223> OTHER INFORMATION: Probe
```

-continued

```
<400> SEQUENCE: 35
atctcgtcct ttaccttctg tgg                                              23

<210> SEQ ID NO 36
<211> LENGTH: 20
<212> TYPE: DNA
<213> ORGANISM: Artificial
<220> FEATURE:
<223> OTHER INFORMATION: Probe

<400> SEQUENCE: 36
gatccatgca tttgtcaagg                                                  20

<210> SEQ ID NO 37
<211> LENGTH: 22
<212> TYPE: DNA
<213> ORGANISM: Artificial
<220> FEATURE:
<223> OTHER INFORMATION: Probe

<400> SEQUENCE: 37
catttgtgta gcctcatcta gg                                               22

<210> SEQ ID NO 38
<211> LENGTH: 23
<212> TYPE: DNA
<213> ORGANISM: Artificial
<220> FEATURE:
<223> OTHER INFORMATION: Probe

<400> SEQUENCE: 38
gtccggagag cagcccttgg tag                                              23

<210> SEQ ID NO 39
<211> LENGTH: 23
<212> TYPE: DNA
<213> ORGANISM: Artificial
<220> FEATURE:
<223> OTHER INFORMATION: Probe

<400> SEQUENCE: 39
tcatcgtata attcttcagc ctc                                              23

<210> SEQ ID NO 40
<211> LENGTH: 22
<212> TYPE: DNA
<213> ORGANISM: Artificial
<220> FEATURE:
<223> OTHER INFORMATION: Probe

<400> SEQUENCE: 40
aaagacggac gtcataccga tg                                               22

<210> SEQ ID NO 41
<211> LENGTH: 21
<212> TYPE: DNA
<213> ORGANISM: Artificial
<220> FEATURE:
<223> OTHER INFORMATION: Probe

<400> SEQUENCE: 41
gacatgtagg cccaatgtcg t                                                21
```